(12) United States Patent
Littlefield et al.

(10) Patent No.: US 6,365,759 B1
(45) Date of Patent: Apr. 2, 2002

(54) INTERMEDIATE COMPOUNDS FOR PREPARING MACROCYLCIC ANALOGS

(75) Inventors: Bruce A. Littlefield, Andover, MA (US); Monica H. Palme, San Jose, CA (US); Boris M. Seletsky, Andover, MA (US); Murray J. Towle, Auburn, NH (US); Melvin J. Yu, Andover, MA (US); Wanjun Zheng, Londonderry, NH (US)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/677,485

(22) Filed: Oct. 2, 2000

Related U.S. Application Data

(63) Continuation of application No. 09/334,488, filed on Jun. 16, 1999.
(60) Provisional application No. 60/089,682, filed on Jun. 17, 1998.

(51) Int. Cl.[7] .................. C07D 407/00; C07D 311/00
(52) U.S. Cl. ........................ 549/414; 549/396
(58) Field of Search .................. 549/414, 396

(56) References Cited

U.S. PATENT DOCUMENTS

| | | | |
|---|---|---|---|
| 5,338,865 A | 8/1994 | Kishi et al. | 549/214 |
| 5,436,238 A | 7/1995 | Kishi et al. | 514/214 |

FOREIGN PATENT DOCUMENTS

| | | |
|---|---|---|
| EP | 0 572 109 A1 | 12/1993 |
| WO | WO 93/17690 | 9/1993 |

OTHER PUBLICATIONS

Aicher et al., "Total Synthetic of Halichondrin B and Norhalichondrin B," J. Am. Chem. Soc. 114:3162–3164 (1992).
Horita et al., "Synthesis Studies of Halichondrin B, and Antitumor Polyether Macrolide Isolated from a Marine Sponge. 8. Synthesis of the Lactone Part (C1–C36) via Horner–Emmons Coupling Between C1–C15 and C16–C36 Fragments and Yamaguchi Lactonization," Tetrahedron Letters 38:8965–8968 (1997).
Stamos et al., "New Synthetic Route to the C.14–C.38 Segment of Halichondrins," J. Org. Chem. 62:7552–7553 (1997).

*Primary Examiner*—Amelia Owens
(74) *Attorney, Agent, or Firm*—Clark & Elbing LLP

(57) ABSTRACT

Intermediate compounds of the formulas

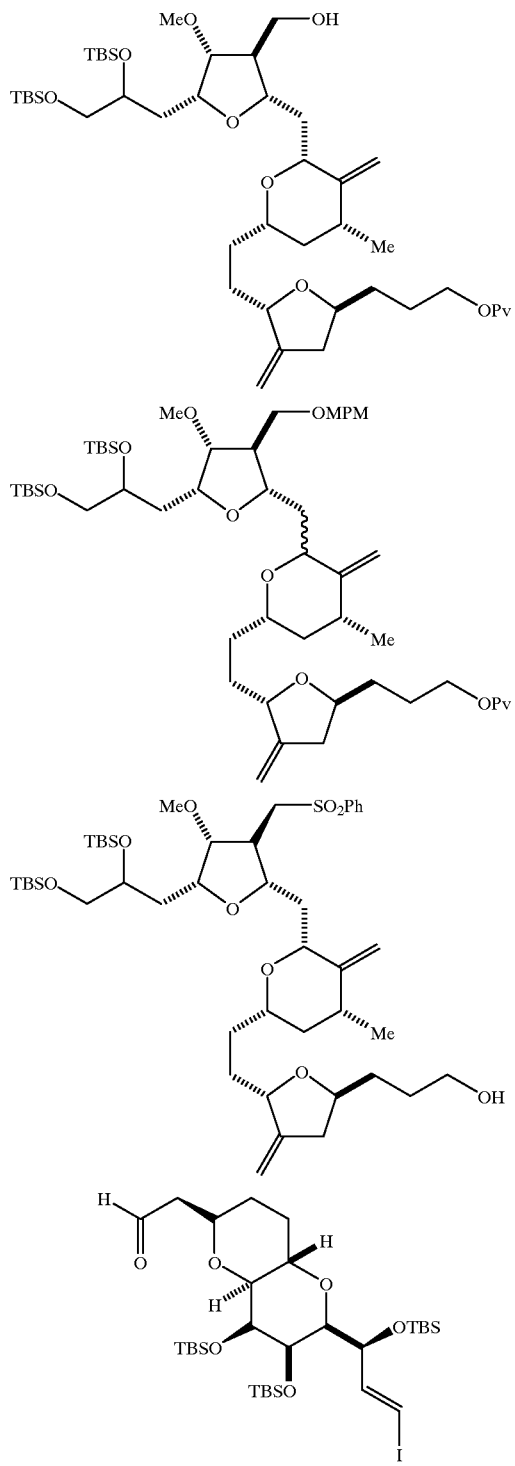

for use in the preparation of macrocyclic analogs.

4 Claims, 3 Drawing Sheets

INTERMEDIATE COMPOUNDS FOR PREPARING MACROCYLCIC ANALOGS

This application is a continuation of and claims priority from United States patent application 09/334,488, filed Jun. 16, 1999, which claims priority from United States provisional patent application 60/089,682, filed Jun. 17, 1998.

BACKGROUND

The invention relates to pharmaceutically active macrolides. Halichondrin B is a potent anticancer agent originally isolated from the marine sponge *Halichondria okadai*, and subsequently found in *Axinella* sp., *Phakellia carteri*, and *Lissondendryx* sp.

A total synthesis of Halichondrin B was published in 1992 (Aicher, T. D. et al., *J. Am. Chem. Soc.* 114:3162–3164). Halichondrin B has demonstrated in vitro inhibition of tubulin polymerization, microtubule assembly, beta$^S$-tubulin crosslinking, GTP and vinblastine binding to tubulin, and tubulin-dependent GTP hydrolysis and has shown in vitro and in vivo anti-cancer properties.

SUMMARY OF THE INVENTION

The invention provides halichondrin analogs having pharmaceutical activity, such as anticancer or antimitotic (mitosis-blocking) activity. These compounds are substantially smaller than halichondrin B. The invention features a compound having the formula (I):

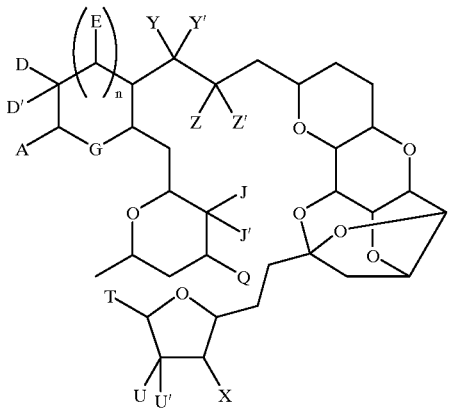

Formula (I)

In formula (I), A is a $C_{1-6}$ saturated or $C_{2-6}$ unsaturated hydrocarbon skeleton, the skeleton being unsubstituted or having between 1 and 13 substituents, preferably between 1 and 10 substituents, e.g., at least one substituent selected from cyano, halo, azido, $Q_1$, and oxo. Each $Q_1$ is independently selected from $OR_1$, $SR_1$, $SO_2R_1$, $OSO_2R_1$, $NR_2R_1$, $NR_2(CO)R_1$, $NR_2(CO)(CO)R_1$, $NR_4(CO)NR_2R_1$, $NR_2(CO)OR_1$, $(CO)OR_1$, $O(CO)R_1$, $(CO)NR_2R_1$, and $O(CO)NR_2R_1$. The number of substituents can be, for example, between 1 and 6, 1 and 8, 2 and 5, or 1 and 4. Throughout the disclosure, numerical ranges are understood to be inclusive.

Each of $R_1$, $R_2$, $R_4$, $R_5$, and $R_6$ is independently selected from H, $C_{1-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl (e.g., p-fluorophenyl or p-chlorophenyl), $C_{6-10}$ hydroxyaryl, $C_{1-4}$ alkoxy-$C_6$ aryl (e.g., p-methoxyphenyl, 3,4,5-trimethoxyphenyl, p-ethoxyphenyl, or 3,5-diethoxyphenyl), $C_{6-10}$ aryl-$C_{1-6}$ alkyl (e.g., benzyl or phenethyl), $C_{1-6}$ alkyl-$C_{6-10}$ aryl, $C_{6-10}$ haloaryl-$C_{6-10}$ alkyl, $C_{1-6}$ alkyl-$C_{6-10}$ haloaryl, ($C_{1-3}$ alkoxy-$C_6$ aryl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl. There may be more than one $R_1$, for example, if A is substituted with two different alkoxy ($OR_1$) groups such as butoxy and 2-aminoethyoxy.

Examples of A include 2,3-dihydroxypropyl, 2-hydroxyethyl, 3-hydroxy-4-perfluorobutyl, 2,4,5-trihydroxypentyl, 3-amino-2-hydroxypropyl, 1,2-dihydroxyethyl, 2,3-dihyroxy-4-perflurobutyl, 3-cyano-2-hydroxypropyl, 2-amino-1-hydroxy ethyl, 3-azido-2-hydroxypropyl, 3,3-difluoro-2,4-dihydroxybutyl, 2,4-dihydroxybutyl, 2-hydroxy-2(p-fluorophenyl)-ethyl, —$CH_2$(CO)(substituted or unsubstituted aryl), —$CH_2$(CO)(alkyl or substituted alkyl, such as haloalkyl or hydroxyalkyl) and 3,3-difluoro-2-hydroxypent-4-enyl.

Examples of $Q_1$ include —NH(CO)(CO)-(heterocyclic radical or heteroaryl), —$OSO_2$-(aryl or substituted aryl), —O(CO)NH-(aryl or substituted aryl), aminoalkyl, hydroxyalkyl, —NH(CO)(CO)-(aryl or substituted aryl), —NH(CO)(alkyl)(heteroaryl or heterocyclic radical), O(substituted or unsubstituted alkyl)(substituted or unsubstituted aryl), and —NH(CO)(alkyl)(aryl or substituted aryl).

Each of D and D' is independently selected from $R_3$ and $OR_3$, wherein $R_3$ is H, $C_{1-3}$ alkyl, or $C_{1-3}$ haloalkyl. Examples of D and D' are methoxy, methyl, ethoxy, and ethyl. In some embodiments, one of D and D' is H.

The value for n is 1 or preferably 0, thereby forming either a six-membered or five-membered ring. This ring can be unsubstituted or substituted, e.g., where E is $R_5$ or $OR_5$, and can be a heterocyclic radical or a cycloalkyl, e.g. where G is S, $CH_2$, $NR_6$, or preferably O.

Each of J and J' is independently H, $C_{1-6}$ alkoxy, or $C_{1-6}$ alkyl; or J and J' taken together are =$CH_2$ or —O-(straight or branched $C_{1-5}$ alkylene or alkylidene)-O-, such as exocyclic methylidene, isopropylidene, methylene, or ethylene. Q is $C_{1-3}$ alkyl, and is preferably methyl. T is ethylene or ethenylene, optionally substituted with (CO)$OR_7$, where $R_7$ is H or $C_{1-6}$ alkyl. Each of U and U' is independently H, $C_{1-6}$ alkoxy, or $C_{1-6}$ alkyl; or U and U' taken together are =$CH_2$ or —O-(straight or branched $C_{1-5}$ alkylene or alkylidene)-O-. X is H or $C_{1-6}$ alkoxy. Each of Y and Y' is independently H or $C_{1-6}$ alkoxy; or Y and Y' taken together are =O, =$CH_2$, or (straight or branched $C_{1-5}$ alkylene or alkylidene)-O-. Each of Z and Z' is independently H or $C_{1-6}$ alkoxy; or Z and Z' taken together are =O, =$CH_2$, or -(straight or branched $C_{1-5}$ alkylene or alkylidene)-O-.

The invention features compounds of sufficient stability to be suitable for pharmaceutical development. The invention also features pharmaceutically acceptable salts of disclosed compounds, disclosed novel synthetic intermediates, pharmaceutical compositions containing one or more disclosed compounds, methods of making the disclosed compounds or intermediates, and methods of using the disclosed compounds or compositions. Methods of use include methods for reversibly or irreversibly inhibiting mitosis in a cell, and for inhibiting cancer or tumor growth in vitro, in vivo, or in a patient. The invention also features methods for identifying an anti-mitotic or anti-cancer agent, such as a reversible or, preferably, an irreversible agent.

DETAILED DESCRIPTION OF THE INVENTION

Figure 1:
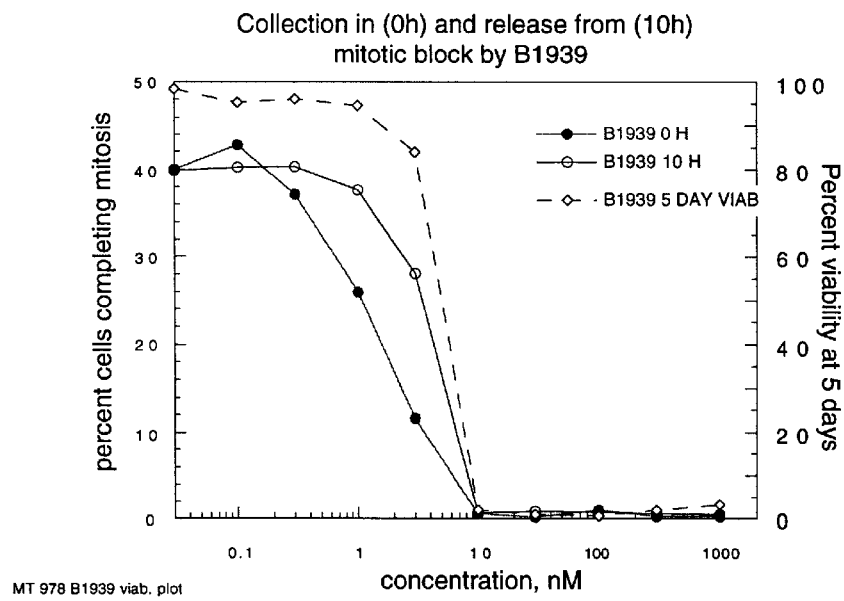
FIG. 1 is a graph showing the percentage of cells which have completed mitosis and returned to the $G_1$ phase as a function of concentration of compound B1939 in a mitotic block assay. The minimum concentration required for complete mitotic block at 0 hour is 10 nM. The minimum concentration required for complete mitotic block at 10 hour (after washout) is also 10 nM. The reversibility ratio is therefore 1 for B1939. Superimposed upon this graph is a curve showing the percentage of visible cells at 5 days as a function of concentration of compound B1939. Viability drops to very low levels at the same concentration as the 10 hour mitotic blcok.

A. Definitions
B. Halichondrin Analogs
C. Synthesis of Halichondrin Analogs
D. Pharmacological Activity
E. Uses A. Definitions The following terms are defined in part below and by their usage herein.

Hydrocarbon skeletons contain carbon and hydrogen atoms and may be linear, branched, or cyclic. Unsaturated hydrocarbons include one, two, three or more C—C double bonds ($sp^2$) or C—C triple bonds (sp). Examples of unsaturated hydrocarbon radicals include ethynyl, 2-propynyl, 1-propenyl, 2-butenyl, 1,3-butadienyl, 2-pentenyl, vinyl (ethenyl), allyl, and isopropenyl. Examples of bivalent unsaturated hydrocarbon radicals include alkenylenes and alkylidenes such as methylidyne, ethylidene, ethylidyne, vinylidene, and isopropylidene. In general, compounds of the invention have hydrocarbon skeletons ("A" in formula (I)) that are substituted, e.g., with hydroxy, amino, cyano, azido, heteroaryl, aryl, and other moieties described herein. Hydrocarbon skeletons may have two geminal hydrogen atoms replaced with oxo, a bivalent carbonyl oxygen atom (=O), or a ring-forming substituent, such as -O-(straight or branched alkylene or alkylidene)-O- to form an acetal or ketal.

$C_{1-6}$ alkyl includes linear, branched, and cyclic hydrocarbons, such as methyl, ethyl, propyl, isopropyl, butyl, isobutyl, sec-butyl, tert-butyl, pentyl, isopentyl, sec-pentyl, neo-pentyl, tert-pentyl, cyclopentyl, hexyl, isohexyl, sec-hexyl, cyclohexyl, 2-methylpentyl, tert-hexyl, 2,3-dimethylbutyl, 3,3-dimethylbutyl, 1,3-dimethylbutyl, and 2,3-dimethyl but-2-yl. Alkoxy (—OR), alkylthio (—SR), and other alkyl-derived moieties (substituted, unsaturated, or bivalent) are analogous to alkyl groups (R). Alkyl groups, and alkyl-derived groups such as the representative alkoxy, haloalkyl, hydroxyalkyl, alkenyl, alkylidene, and alkylene groups, can be $C_{2-6}$, $C_{3-6}$, $C_{1-3}$, or $C_{2-4}$.

Alkyls substituted with halo, hydroxy, amino, cyano, azido, and so on can have 1, 2, 3, 4, 5 or more substituents, which are independently selected (may or may not be the same) and may or may not be on the same carbon atom. For example, haloalkyls are alkyl groups with at least one substituent selected from fluoro, chloro, bromo, and iodo. Haloalkyls may have two or more halo substituents which may or may not be the same halogen and may or may not be on the same carbon atom. Examples include chloromethyl, periodomethyl, 3,3-dichloropropyl, 1,3-difluorobutyl, and 1-bromo-2-chloropropyl.

Heterocyclic radicals and heteroaryls include furyl, pyranyl, isobenzofuranyl, chromenyl, xanthenyl, phenoxathienyl, 2H-pyrrolyl, pyrrolyl, imidazolyl (e.g., 1-, 2- or 4- imidazolyl), pyrazolyl, isothiazolyl, isoxazolyl, pyridyl (e.g., 1-, 2-, or 3- pyridyl), pyrazinyl, pyrimidinyl, pyridazinyl, indolizinyl, isoindolyl, 3H-indolyl, indolyl (e.g., 1-, 2-, or 3-indolyl), indazolyl, purinyl, 4H-quinolixinyl, isoquinolyl, quinolyl, phthalazinyl, naphthyridinyl, quinoxalinyl, quinazolyinyl, cinnolinyl, pteridinyl, pyrrolinyl, pyrrolidinyl, imidazolidinyl, pyrazolidinyl, pyrazolinyl, piperidyl, piperazinyl, indolinyl, isoindolinyl, and morpholinyl. Heterocyclic radicals and heteroaryls may be linked to the rest of the molecule at any position along the ring. Heterocyclic radicals and heteroaryls can be $C_{2-9}$, or smaller, such as $C_{3-6}$, $C_{2-5}$, or $C_{3-7}$.

Aryl groups include phenyl, benzyl, naphthyl, tolyl, mesityl, xylyl, and cumenyl.

It is understood that "heterocyclic radical", "aryl", and "heteroaryl" include those having 1, 2, 3, 4, or more substituents independently selected from lower alkyl, lower alkoxy, amino, halo, cyano, nitro, azido, and hydroxyl. Heterocyclic radicals, heteroaryls, and aryls may also be bivalent substituents of hydrocarbon skeleton "A" in formula (I).

B. Halichondrin Analogs

Referring to formula (I) in the Summary section, embodiments of the invention include compounds wherein n is 0; wherein each of D and D' is independently selected from $R_3$, $C_{1-3}$ alkoxy, and $C_{1-3}$ haloalkyloxy; wherein $R_5$ is selected from H, $C_{2-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl, $C_{6-10}$ hydroxyaryl, $C_{1-3}$ alkoxy-$C_6$ aryl, $C_{6-10}$ aryl-$C_{1-6}$ alkyl, $C_{1-6}$ alkyl-$C_{6-10}$ aryl, $C_{6-10}$ haloaryl-$C_{1-6}$ alkyl, $C_{1-6}$ alkyl-$C_{6-10}$ haloaryl, ($C_{1-3}$ alkoxy-$C_6$ aryl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl; and combinations thereof.

Other embodiment includes compounds having one or more of the following characteristics: (a) wherein A is a $C_{1-6}$ saturated or $C_{2-6}$ unsaturated hydrocarbon skeleton, the skeleton having at least one substituent selected from cyano, halo, azido, $Q_1$, and oxo; (b) each $Q_1$ is independently selected from $OR_1$, $SR_1$, $SO_2R_2$, $OSO_2R_2$, $NR_2R_1$, $NR_2(CO)R_1$, $NR_2(CO)R_1$, and $O(CO)NR_2R_1$; (c) Z and Z' taken together are =O or =CH$_2$; (d) wherein each $Q_1$ is independently selected from $OR_1$, $SR_1$, $SO_2R_1$, $OSO_2R_1$, $NH(CO)R_1$, $NH(CO)(CO)R_1$, and $O(CO)NHR_1$; (e) each $R_1$ is independently selected from $C_{1-6}$ alkyl, $C_{1-6}$ haloalkyl, $C_6$ aryl, $C_6$ haloaryl, $C_{1-3}$ alkoxy-$C_6$ aryl, $C_6$ aryl-$C_{1-3}$ alkyl, $C_{1-3}$ alkyl-$C_6$ aryl, $C_6$ haloaryl-$C_{1-3}$ alkyl, $C_{1-3}$ alkyl-$C_6$ haloaryl, ($C_{1-3}$ alkoxy-$C_6$ aryl)-$C_{1-3}$ alkyl, $C_{2-9}$ heterocyclic radical, $C_{2-9}$ heteroaryl, and $C_{2-9}$ heteroaryl-$C_{1-6}$ alkyl; (f) one of D and D' is methyl or methoxy and the other is H; (g) n is 0; (h) G is O; (i) J and J' taken together are $=CH_2$; () Q is methyl; (k) T is ethylene; (l) U and U' taken together are $=CH_2$; (m) X is H; (n) each of Y and Y' is H; and (o) Z and Z' taken together are $=O$. Examples of combinations are the combination of (h)–(m), the combination of (a) and (b), the combination of (f) and (h), and the combination of (h) and where one of D and D' is methyl and the other is H. Two particularly preferred compounds are B1793 and B1939.

Another embodiment includes compounds wherein Q, is independently selected from $OR_1$, $SR_1$, $SO_2R_1$, and $OSO_2R_1$; and each $R_1$ is independently selected from $C_{1-6}$ alkyl, $C_{1-6}$ haloalkyl, $C_6$ aryl, $C_6$ haloaryl, $C_{1-3}$ alkoxy-$C_6$ aryl, $C_6$ aryl-$C_{1-3}$ alkyl, $C_{1-3}$ alkyl-$C_6$ aryl, $C_6$ haloaryl-$C_{1-3}$ alkyl, $C_{1-3}$ alkyl-$C_6$ haloaryl, and ($C_{1-3}$ alkoxy-$C_6$ aryl)-$C_{1-3}$ alkyl. Other embodiments include compounds wherein: one of D and D' is alkyl or alkoxy, where n is 1; (f) as above, where n is 1; E is alkoxy, where n is 1; n is 0, where one of D and D' is hydroxy and the other is H; and (f) as above, where n is 1 and E is methyl.

The invention also features compounds wherein: (1) A has at least one substituent selected from hydroxyl, amino, azido, halo, and oxo; (2) A is a saturated hydrocarbon skeleton having at least one substituent selected from bydroxyl, amino, and azido (e.g., B1793, B1939, B2042, B1794, and B1922);(3) A has at least two substituents independently selected from hydroxyl, amino, and azido (e.g., B2090 and B2136); (4) A has at least two substituents independently selected from hydroxyl and amino (e.g., B2042 and B2090); (5) A has at least one hydroxyl substituent and at least one amino substituent (e.g., B1939 and B2136); (6) A has at least two hydroxyl substituents (e.g., B1793 and B1794); (7) A is a $C_{2-4}$ hydrocarbon skeleton that is substituted (e.g., B2004, B2037, B1920, B2039, B2070, B2090, and B2043); (8) A is a $C_3$ hydrocarbon skeleton that is substituted (e.g., B1793, B1920,B1984, B1988, B1939, B1940, B2014); (9) A has an (S)-hydroxyl alpha to the carbon atom linking A to the ring containing G (e.g., B1793, B1939 or B1920) or an (R)-hydroxyl (e.g. B2102, B2013, B2042); and (10) A is a $C_{1-6}$ saturated hydrocarbon skeleton having at least one substituent selected from hydroxyl and cyano (e.g., B2013, B2037, B2102, B2086, and B2091). By (S)-hydroxyl is meant the configuration of the carbon atom having the hydroxyl group is (S). Embodiments of the invention also include compounds which have at least two substituents on the carbon atoms (1) alpha and gamma, (2) beta and gamma, or preferably (3) alpha and beta to the carbon atom linking A to the ring containing G. The alpha, beta, and gamma carbon atoms can have an (R) or (S) configuration The invention further provides preferred compounds having the formula (1)-A, shown below, wherein the substituents are identical to those defined above.

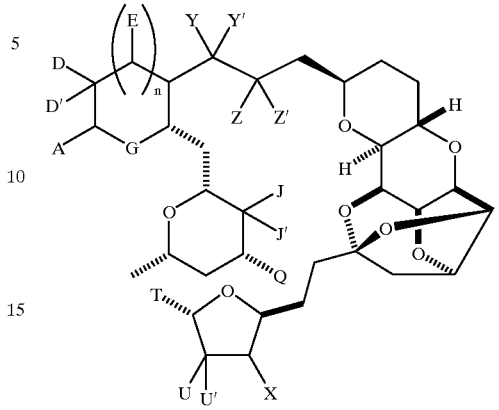

Formula 1-A

The invention further features the following monosaccharide intermediate having formula (II)

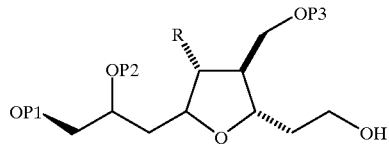

Formula (II)

wherein R is methyl or methoxy, and each of P1, P2, and P3 is independently selected from H and primary alcohol protecting groups. Preferably, the diol sidechain is below the plane of the page and OP2 is above the plane of the page. Primary alcohol protecting groups include esters, ethers, silyl ethers, alkyl ethers, and alkoxyalkyl ethers.

Examples of esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate, crotonate, 4-methoxy-crotonate, benzoate, p-pbenylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl) ethyl, vinyl, allyl, and p-nitrobenzyl.

Examples of silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of benzyl ethers include p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl. Preferably, each of P1 and P2 are TBS and P3 is MPM (see alcohol 19 below). In one aspect, formula (II) can be modified so the hydroxyethyl sidechain can also be a protected hydroxyl, —$CH_2CH_2O$-P4, wherein P4 is independently selected from values for P1. A related intermediate is alcohol 17, where the hydroxyethyl sidechain is a hydroxymethyl sidechain. A corresponding hydroxypropyl sidechain, or aminoalkyl side chain, can be similarly prepared.

P1 and P2, taken together, can be a diol protecting group, such as cyclic acetals and ketals (methylene, ethylidene, benzylidenes, isopropylidene, cyclohexylidene, and cyclopentylidene), silylene derivatives such as di-t-butylsilylene and 1,1,3,3-tetraisopropylidisiloxanylidene derivatives, cyclic carbonates, and cyclic boronates. Methods of adding and removing such hydroxyl protecting groups, and additional protecting groups, are well-known in the art and available, for example, in P. J. Kocienski, *Protecting Groups*, Thieme, 1994, and in T. W. Greene and P. G. M. Wuts, *Protective Groups in Organic Synthesis*, $2^{nd}$ edition, John Wiley & Sons, 1992.

The following section provides representative syntheses of intermediates of formula (II) and halichondrin analogs of formula (I).

C. Synthesis of Halichondrin Analogs

An overview is provided below, followed by synthetic schemes 1–16, and several detailed protocols.

Compounds of general formula 4 can be prepared by the route outlined in Scheme 1. Key fragment F-2 exemplified by vinyl iodide compound X2 can be prepared according to the procedure of Kishi, et al. (Total synthesis of halichondrin B and norhalichondrin B. Aicher, T. D.; Buszek, K. R.; Fang, F. G.; Forsyth, C. J.; Jung, S. H.; Kishi, Y.; Matelich, M. C.; Scola,. M.; Spero, D. M.; Yoon, S. K *J. Am. Chem. Soc.* 1992, 114, 3162–4).

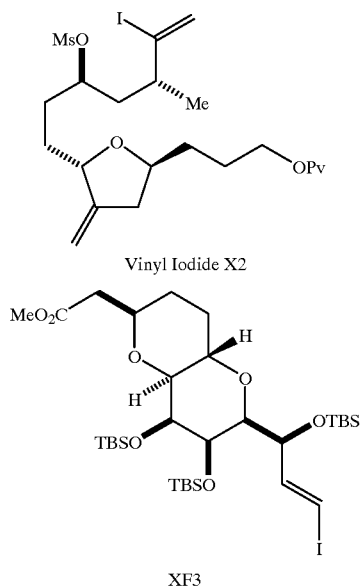

Key fragment F-3 can be obtained by DIBALH reduction of the corresponding methyl ester, XF3, prepared according to the procedure of Stamos, et al (Scheme 2). [Synthetic studies on halichondrins: a practical synthesis of the C.1–C.13 segment. Stamos, D. P.; Kishi, Y. *Tetrahedron Lett.* 1996, 37, 8643–8646]. Synthesis of key fragment F-1 exemplified by compound 20 can be synthesized as described in Scheme 3 or Scheme 4.

Using B1793 as a representative example, coupling of the three key fragments proceeded as outlined in Scheme 5: Nozaki-Hiyama-Kishi coupling of fragments 20 and X2 followed by intramolecular Williamson ether formation furnished tetrahydropyran B2318. Protecting group modification as described in Scheme 5 or alternatively in Scheme 6 afforded primary iodide B2313. Halogen-metal exchange reaction and coupling with key fragment F-3 furnished a mixture of diastereomeric alcohols B2308. Additional protecting group manipulation and oxidation followed by an intramolecular Nozaki-Hiyama-Kishi reaction afforded an intermediate, which when oxidized and treated with TBAF underwent intramolecular hetero-Michael ring closure. PPTs mediated acetal formation furnished B1793.

Aryl groups can be incorporated into the C32 sidechain (e.g. B2043) as exemplified in Scheme 7. Intermediate B2318 was deprotected and the resulting diol oxidatively cleaved to the corresponding aldehyde. Treatment with a Grignard reagent (e.g. p-F-PhMgBr), separation of the resulting diastereomers and silylation furnished 204, which was converted to final product in a manner similar to that described in Scheme 6.

Ether analogs can be prepared from B1793 by treatment with an appropriate alkylating agent (e.g. Scheme 8). Similarly, sulfonates, esters, carbamates, etc. can be prepared from B1793 by treatment with an activated carbonyl component. Oxidative diol cleavage and reduction or selective hydroxyl group oxidation could furnish derivatives such as B2037 and B1934, respectively.

Alternatively, one or more hydroxyl groups could be converted to the corresponding amino groups with subsequent coupling with an activated carbonyl component (Scheme 9). Displacement of the sulfonyl intermediate (e.g. B1920) by carbon or heteroatom nucleophiles could also be readily accomplished (Scheme 10).

C31 methyl analogs can be prepared as outlined in Scheme 11. Indium mediated coupling of an allyl bromide ester with 2,3-O-(3-isopropylidine)-D-glyceraldehyde furnished lactone 103. Hetero Michael addition, lactone reduction, Wittig coupling and intramolecular Michael addition furnished tetrahydrofuran 107. Pummerer rearrangement, protecting group adjustment and DIBALH reduction furnished key fragment 1 (e.g., 114), which was converted to final compound in a manner analogous to that described in Scheme 6.

Fluorine atoms could be introduced as described in Schemes 12–14. Beginning with the appropriate tetrahydrofuran intermediate, fluorinated key fragment 1 was obtained and carried to final compound in a manner analogous to that illustrated in Scheme 6.

Triol derivatives could be similarly prepared from the tetrahydrofuran intermediate. For example, as outlined in Scheme 15 allyltributylstannane addition to aldehyde X32 furnished homoallylic alcohol 33 that was carried to final compound in a similar manner to that described in Scheme 6. These triols could be further modified as exemplified in Scheme 6.

The 1,3 diol derivatives could be prepared from intermediates previously described. For example, B2086 could be oxidatively cleaved and reduced to afford 1,3-diol B2091 (Scheme 16).

Scheme 1
F-1 ──┐
      ├──→ 4
F-2 ──┴── F-3
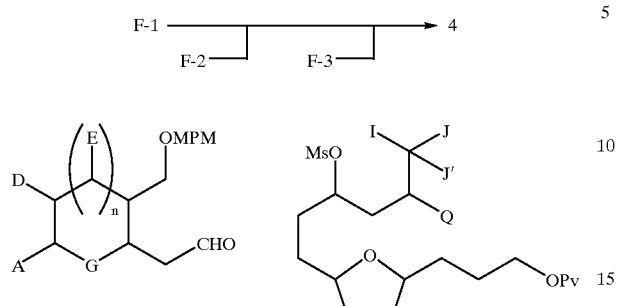
F-1        F-2
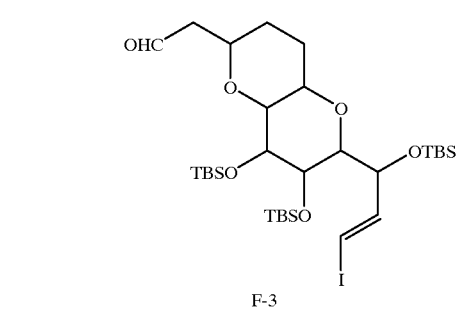
F-3
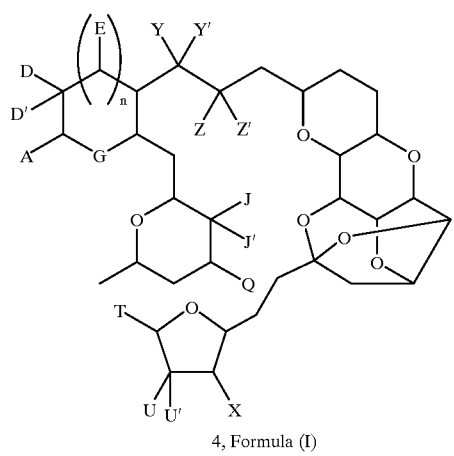
4, Formula (I)
Scheme 2
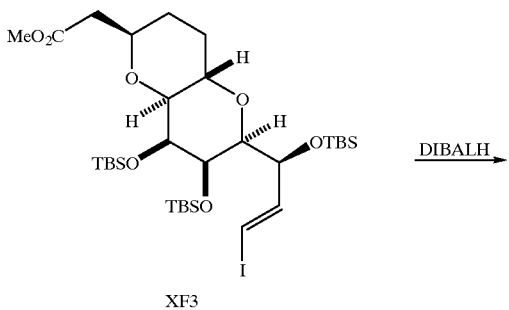
XF3   —DIBALH→
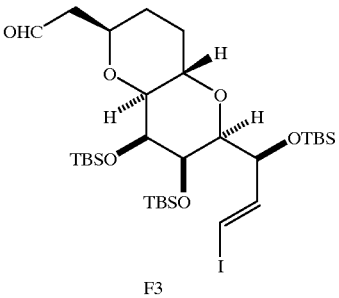
F3
Scheme 3
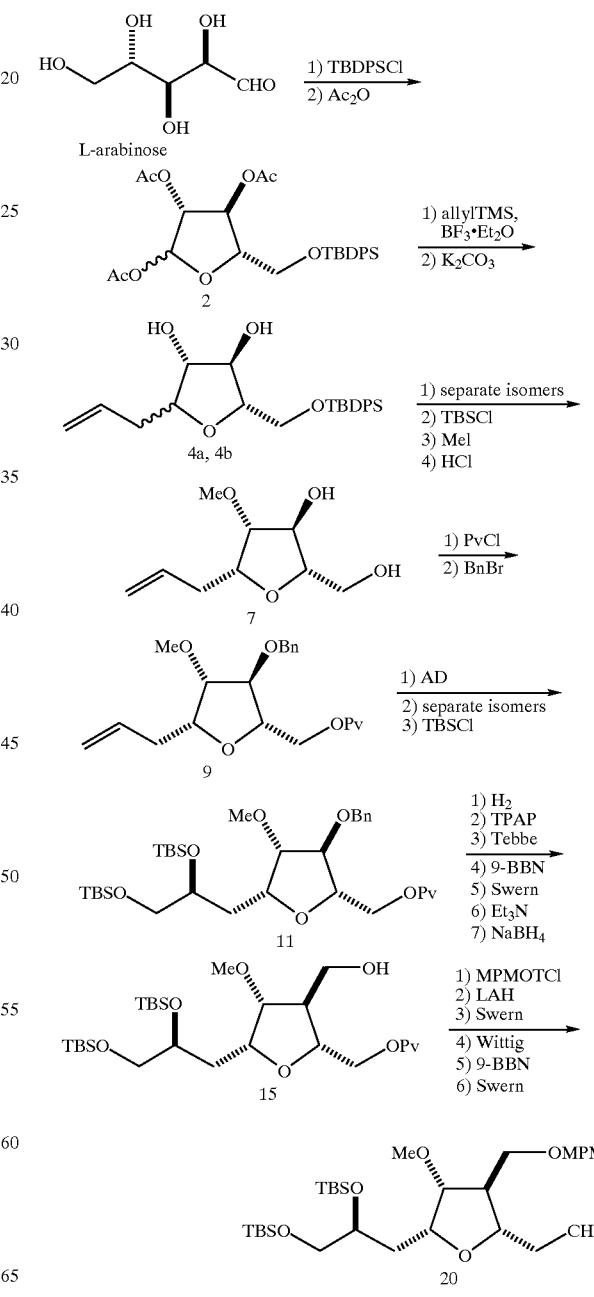

Scheme 4
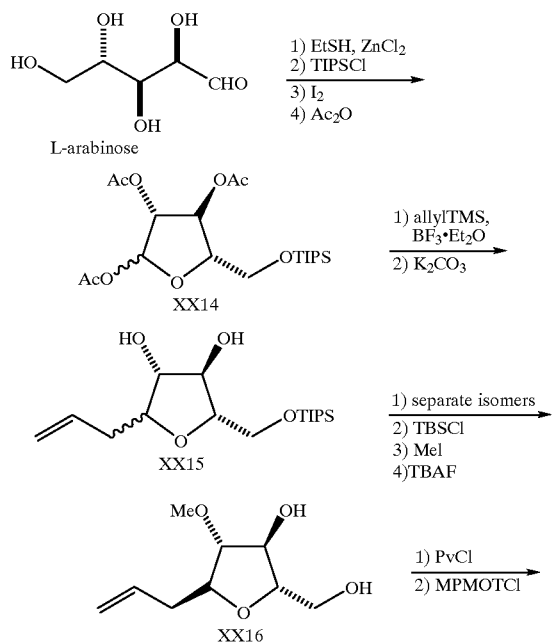
-continued
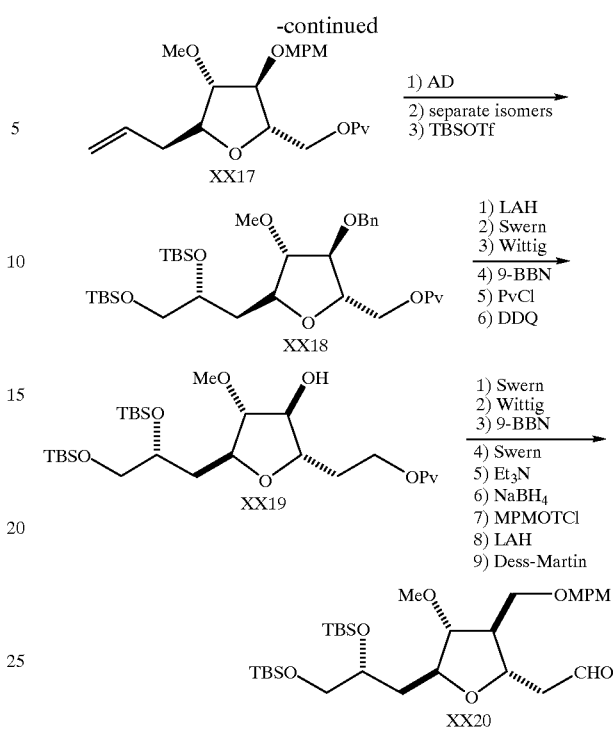
Scheme 5
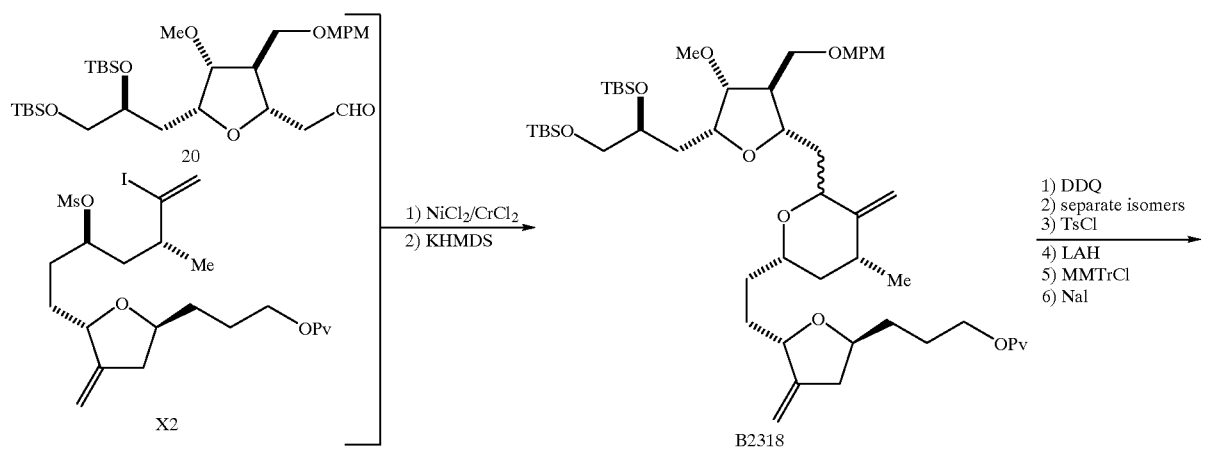

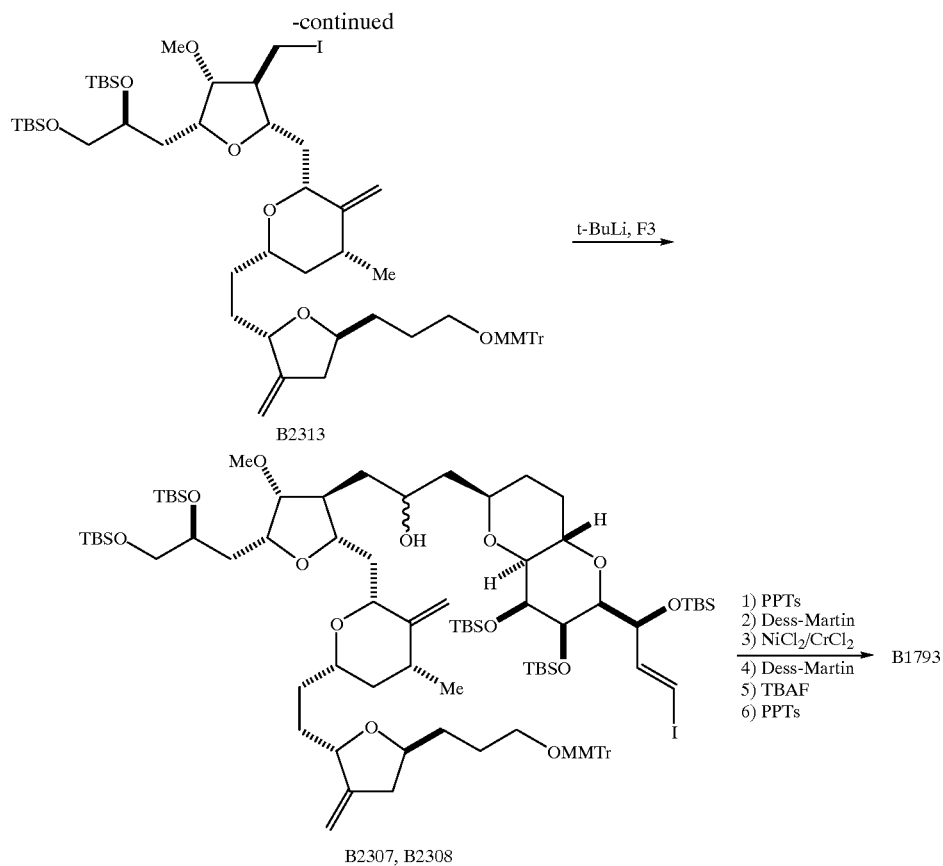
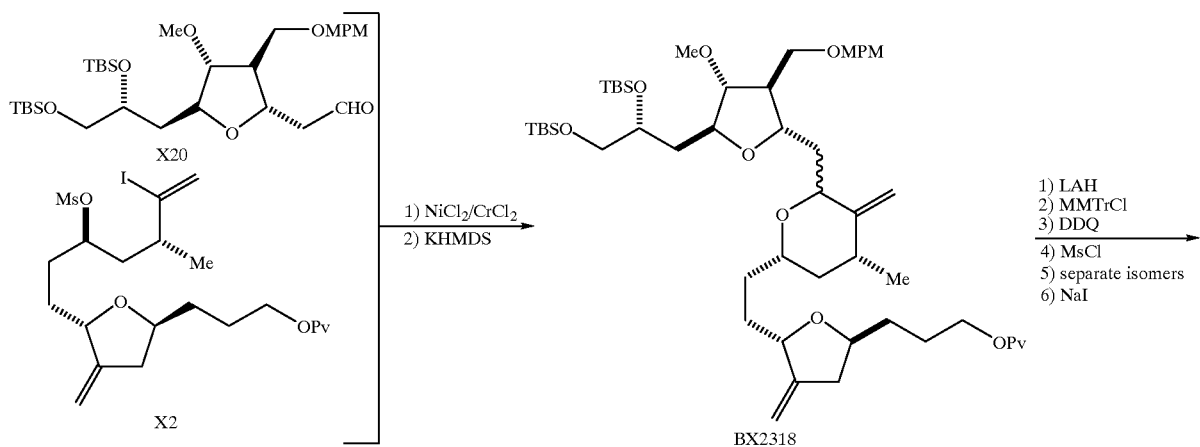
Scheme 6

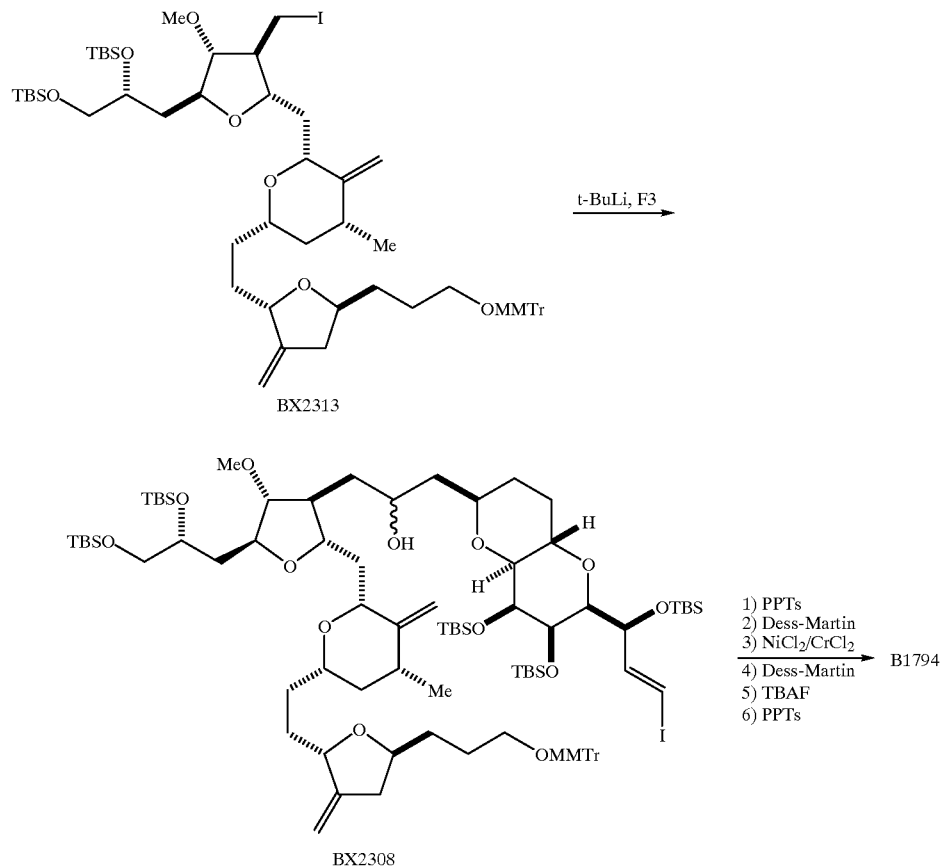
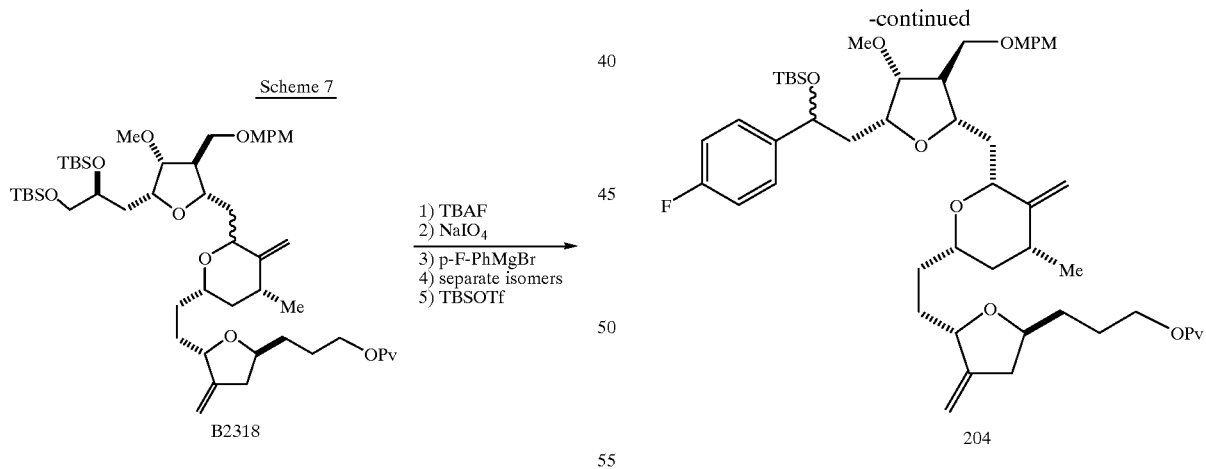
Scheme 7

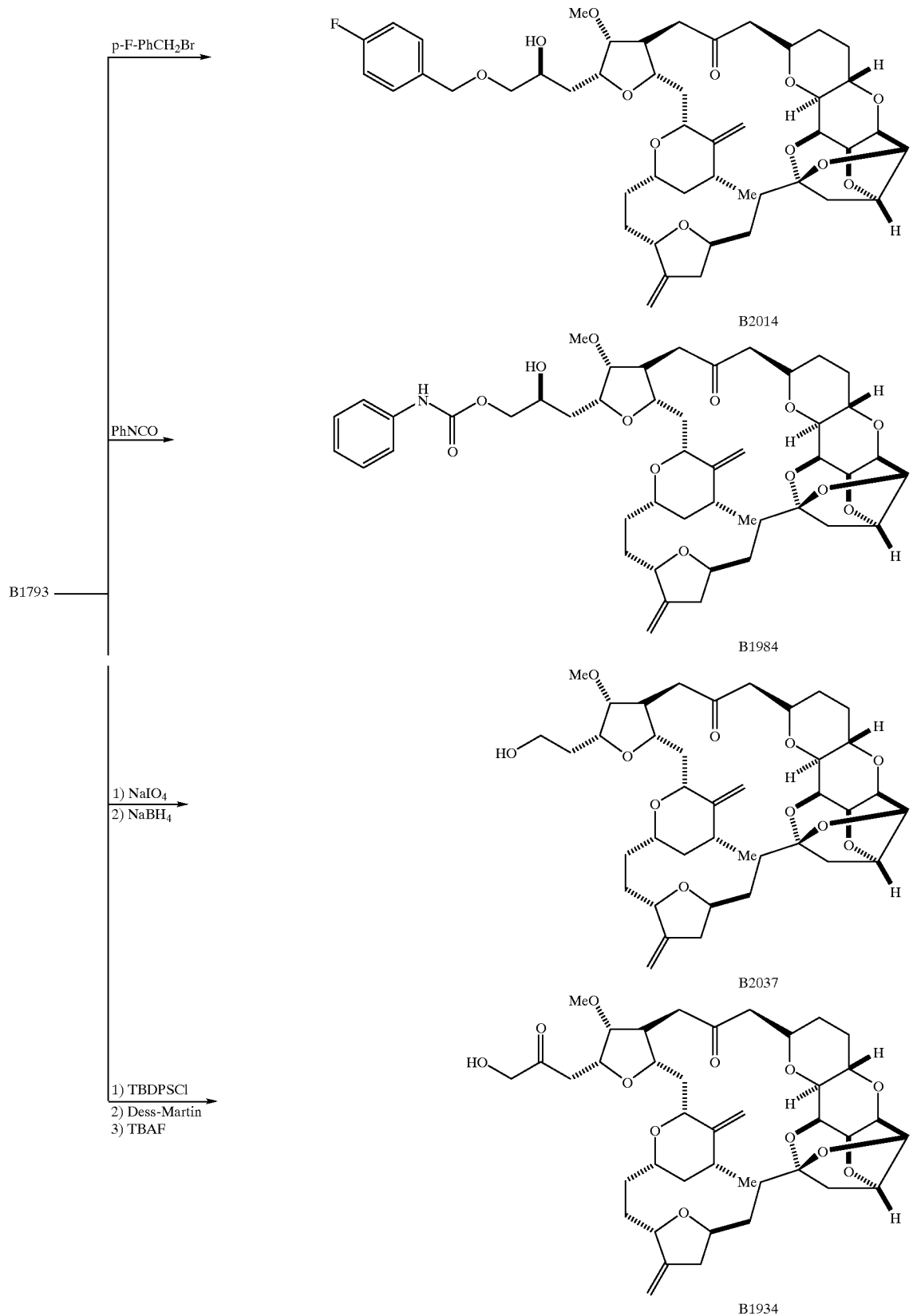

Scheme 9
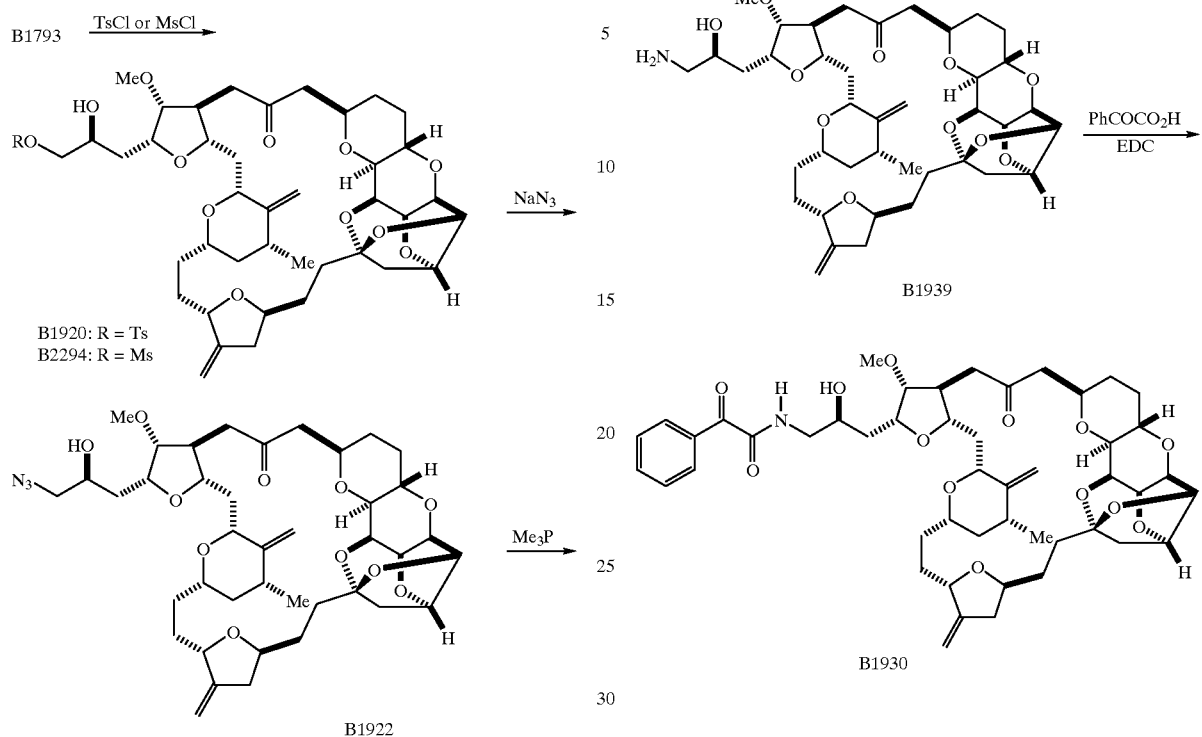
Scheme 10
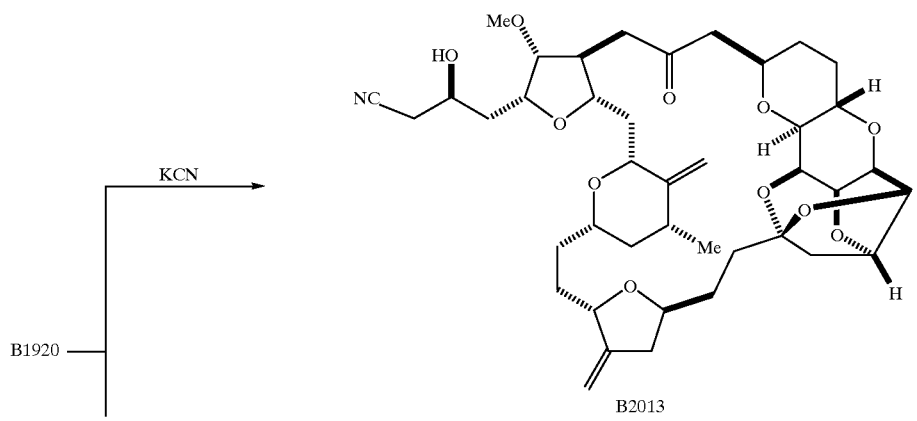

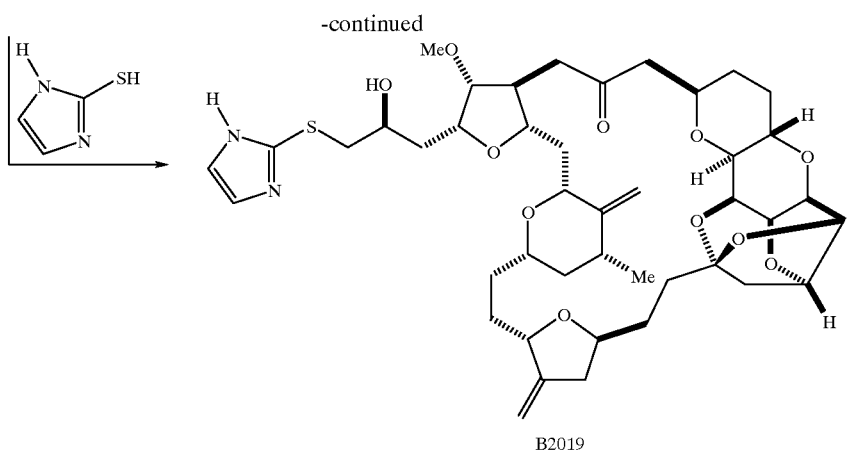
B2019
Scheme 11
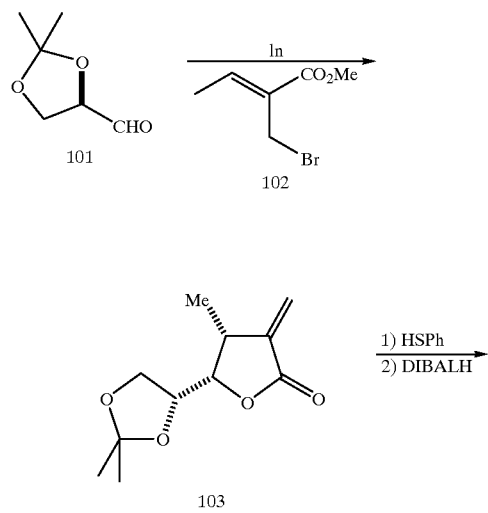
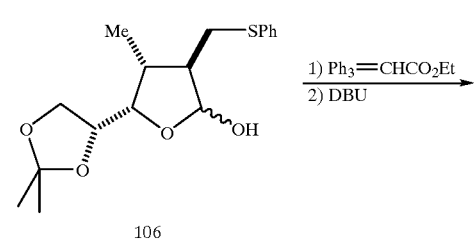
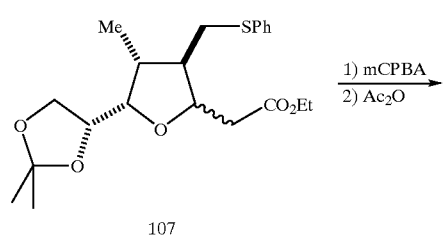
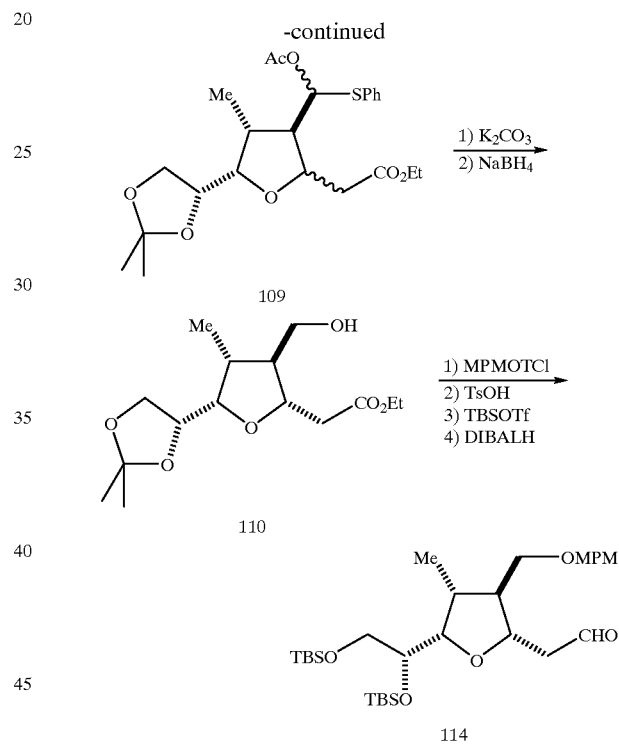
Scheme 12
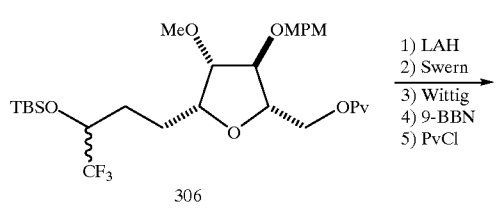

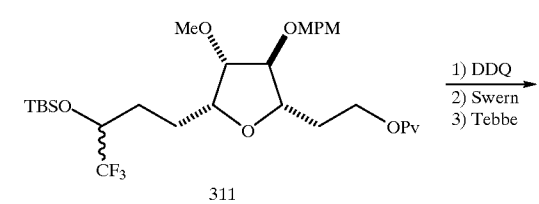
311
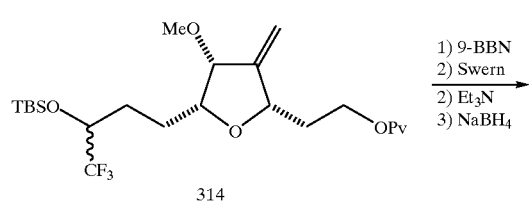
314
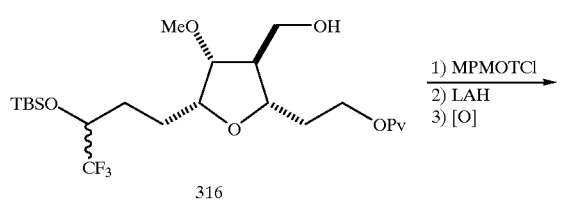
316
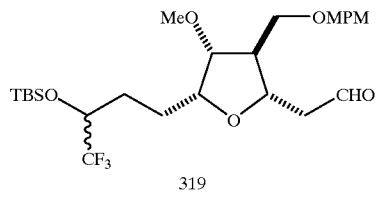
319
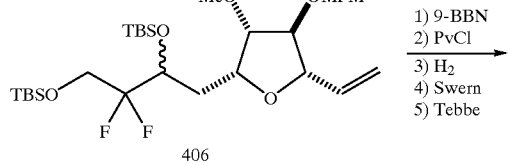
406
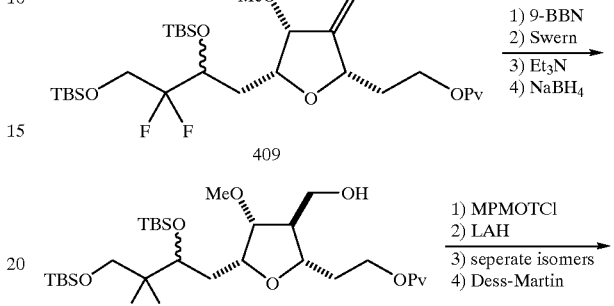
409
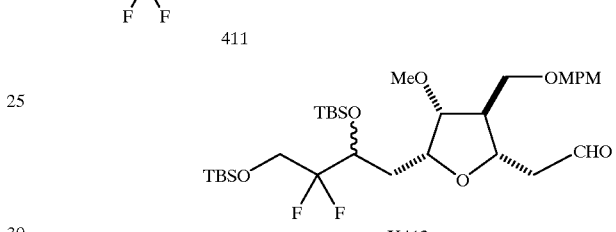
411
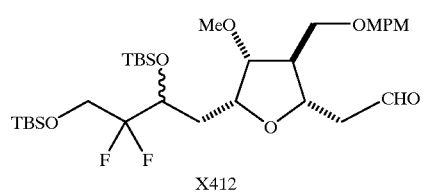
X412
Scheme 13
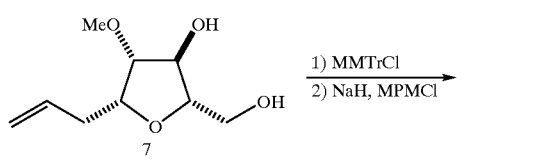
7
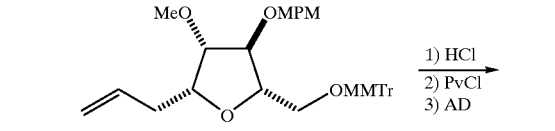
X399
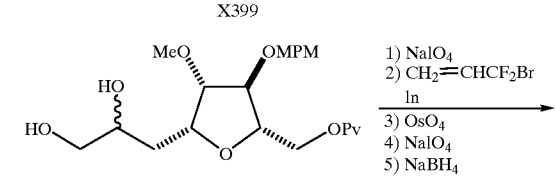
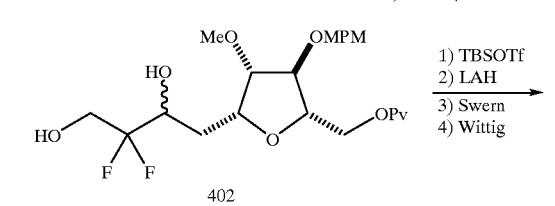
402
Scheme 14
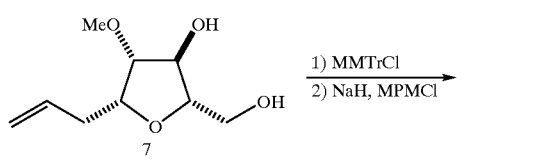
10
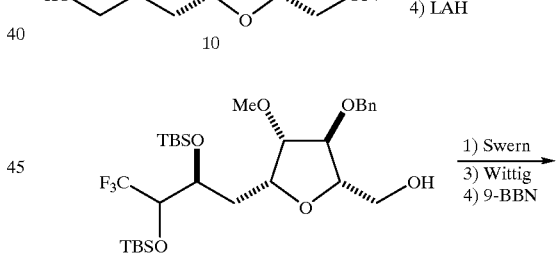
EX11
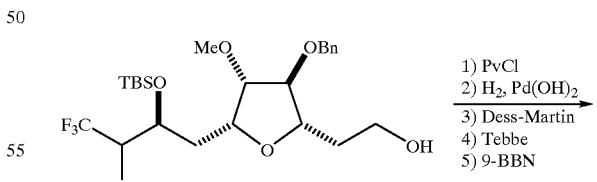
EX12
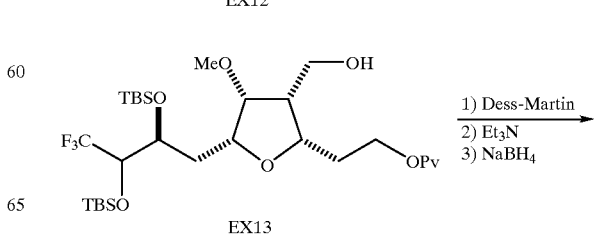
EX13

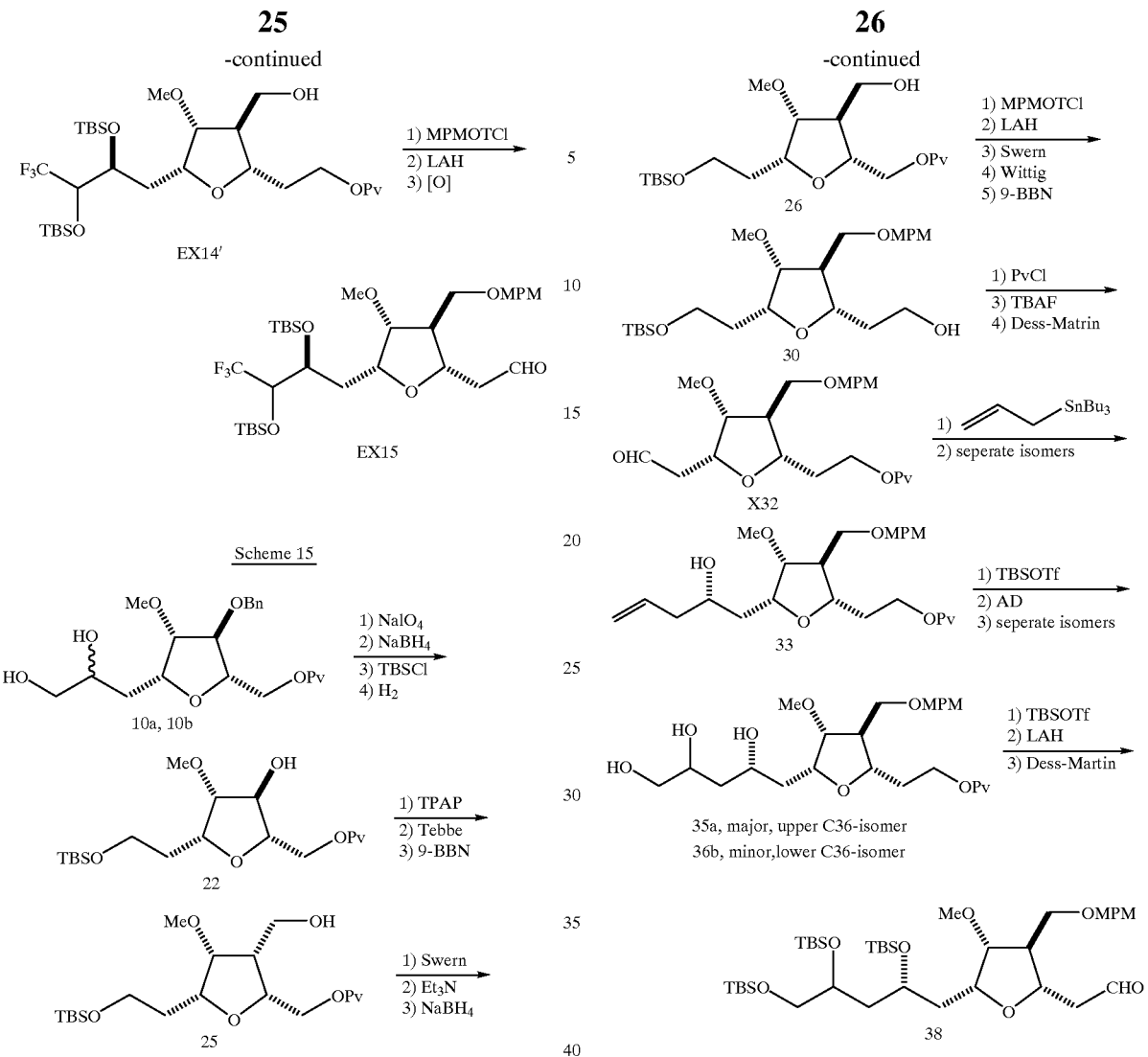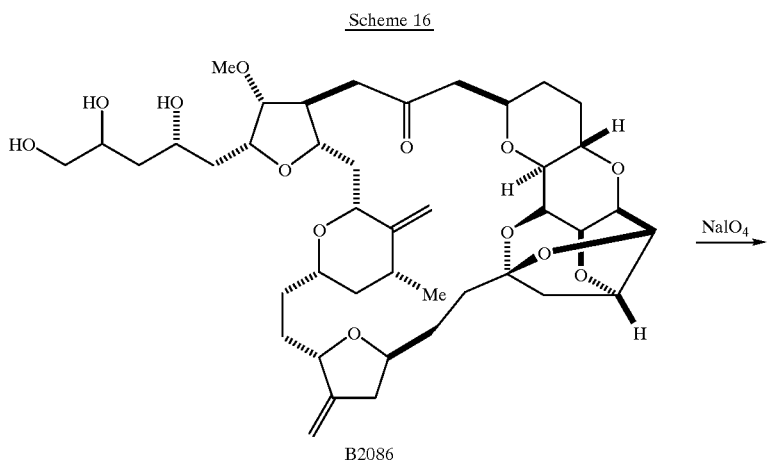

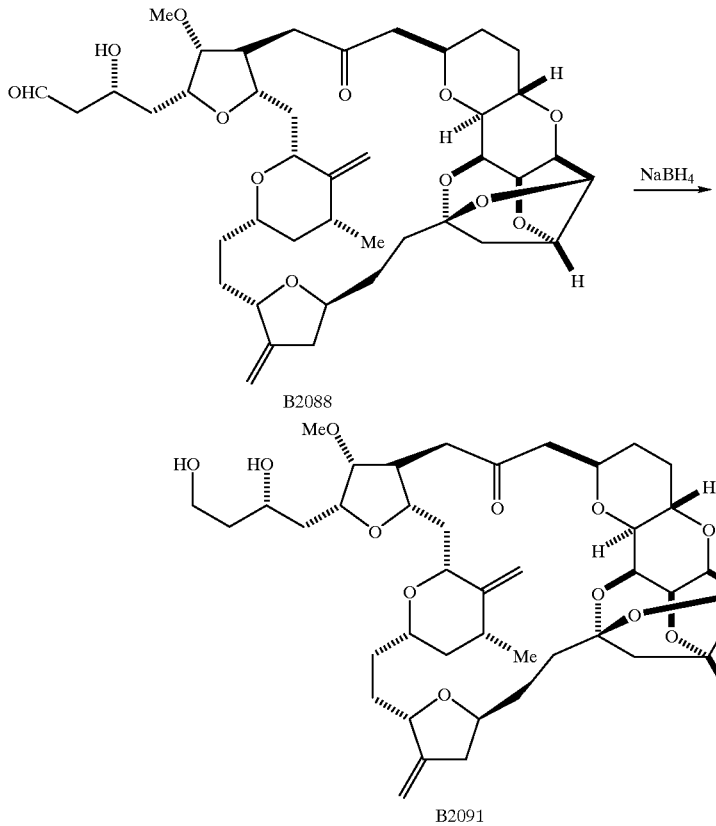

EXPERIMENTAL SECTION
Synthesis of Key Fragment F-3:

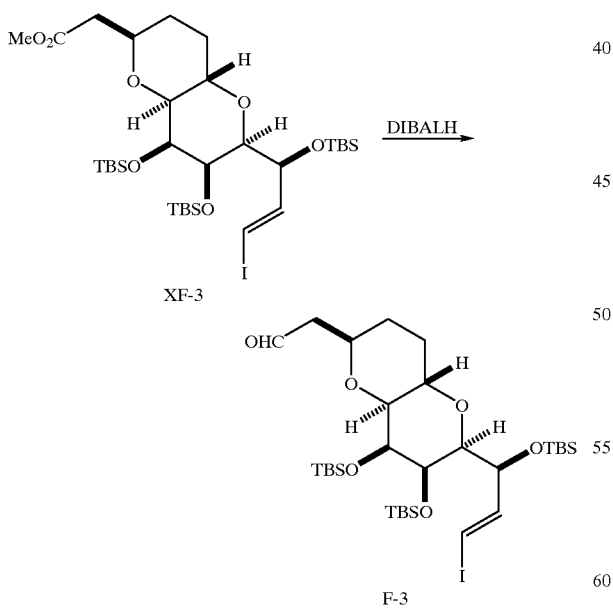

Key Fragment F-3. DIBALH (1 M in toluene, 3.86 mL) was added to a solution of XF-3 (1,46 g, 1.93 mmol) in toluene (37 mL) at −78° C. After stirring for 10 min, the reaction was quenched by careful addition of MeOH (0.46 mL) and H$_2$O (0.21 mL), warmed to rt and stirred for 15 min. The white suspension was filtered through Celite with 1:1 CH$_2$Cl$_2$/Et$_2$O. The filtrate was concentrated and purified by column chromatography (10% EtOAc-hexanes) to give key fragment F-3 (1.34 g, 96%) as an oil.

Synthesis of B1793:

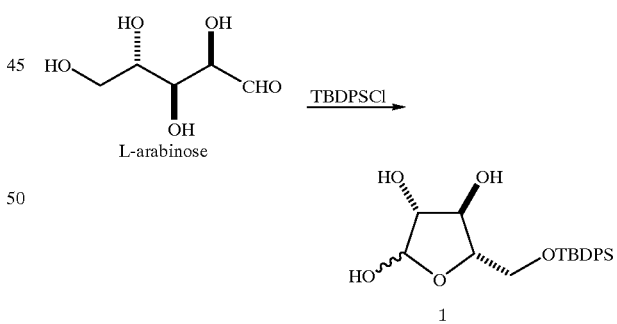

Triol 1 A solution of TBDPSCl (444 mL, 1.7 mol) in DMF (0.5 L) was added in three portions to a suspension of L-arabinose (250.0 g, 1.66 mol), imidazole (231.4 g, 3.40 mol) and DMF (2.5 L). The addition of each portion took 1.5 h with a 30 min and a 15 h interval separating the second and third portions, respectively. The resulting solution was stirred for 3 h, concentrated and purified by flash chromatography (5% to 33% EtOAc-hexanes) to provide triol 1 (394 g, 61%).

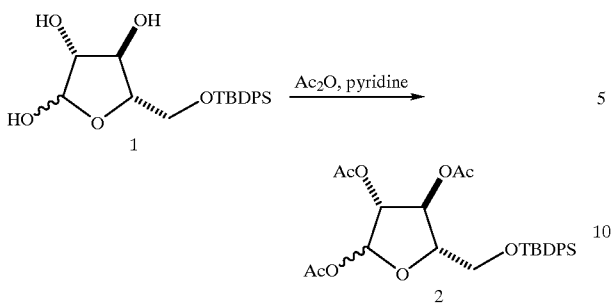

Triacetate 2 Acetic anhydride (6.06 mol) was added over 1.5 h to triol 1 (1.01 mol) in pyridine (1.0 L) at 15° C. The solution was stirred for 1 h, concentrated and purified by flash chromatography (15% to 25% EtOAc-hexanes) to afford triacetate 2 (518 g, 97%).

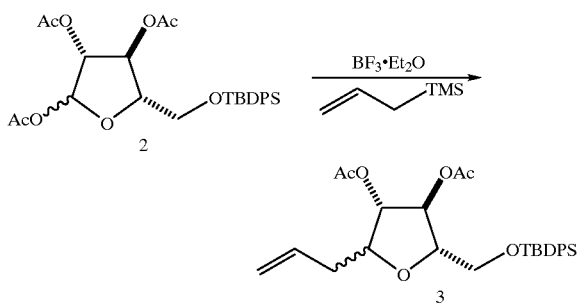

Diacetates 3 Allyltrimethylsilane (1.11 mol) followed by $BF_3 \cdot OEt_2$ (1.11 mmol) was added over 1.5 h to triacetate 2 (164 g, 0.32 mol) in toluene (1.5 L) at 0° C. The orange solution was stirred for 1 h at 0° C. and for 2 h at rt. The mixture was slowly poured into saturated aqueous $NaHCO_3$ (1.7 L) at 0° C. and stirred for 30 min. The separated aqueous layer was extracted with EtOAc (3×600 mL) and the combined organic layers were dried over $Na_2SO_4$, concentrated and purified by flash chromatography (5% to 10% EtOAc-hexanes) to furnish a mixture of diacetates 3 (108 g, 69%).

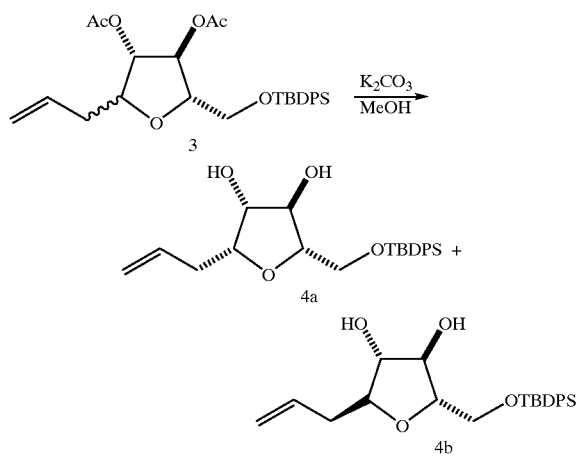

Diol 4a Solid $K_2CO_3$ (72 mmol) was added to diacetates 3 (108 g, 218 mmol) in MeOH (0.5 L) at rt. The suspension was stirred for 2.5 h and then concentrated. The orange residue was suspended in saturated aqueous $NH_4Cl$ (150 mL), extracted with EtOAc (3×150 mL) and the combined organic layers were dried over $Na_2SO_4$, concentrated and purified by flash chromatography (15% to 50% EtOAc-hexanes) to afford alpha-isomer 4a (33.86 g, 37%), and beta-isomer 4b (58 g, 63%).

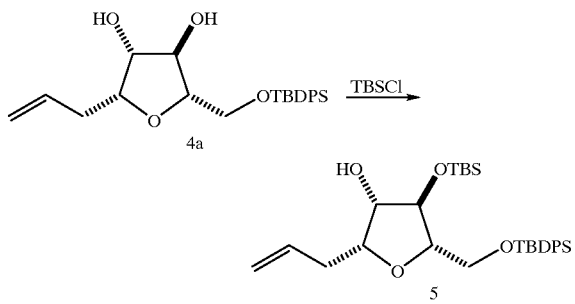

Alcohol 5 Imidazole (16.75 g, 246 mmol) and TBSCl (16.08 g, 107 mmol) were added to a solution of diol 4a (33.86 g, 82 mmol) in $CH_2Cl_2$ (250 mL) at 0° C. After 18 h at 0° C. and 5 h at rt, the reaction mixture was diluted with saturated aqueous $NaHCO_3$ (250 mL), stirred for 30 min and the layers were allowed to separate. The aqueous layer was extracted with EtOAc (3×250 mL) and the combined organic layers were dried over $Na_2SO_4$, concentrated and purified by flash chromatography (2% to 50% EtOAc-hexanes) to furnish alcohol 5 (36.0 g, 83%).

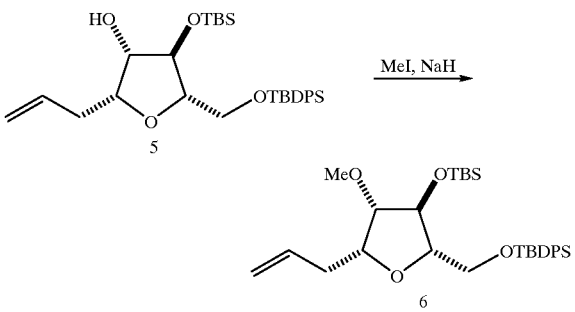

Methyl ether 6 Iodomethane (16.5 mL, 265 mmol) and NaH (60% in mineral oil, 5.28 g, 132 mmol) were added to a solution of alcohol 5 (34.93 g, 66 mmol), THF (320 mL) and DMF (80 mL) at 0° C. After 19 h at 0° C., the reaction was quenched with saturated aqueous $NH_4Cl$ and saturated aqueous $Na_2S_2O_3$. The resulting mixture was stirred for 20 min and the layers were allowed to separate. The aqueous phase was extracted with EtOAc (3×200 mL) and the combined organic layers were dried over $Na_2SO_4$, concentrated and purified by flash chromatography (3% EtOAc-hexanes) to afford methyl ether 6 (34.23 g, 96%).

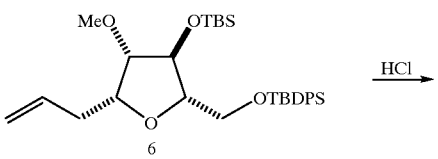

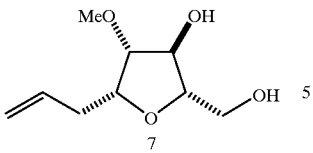

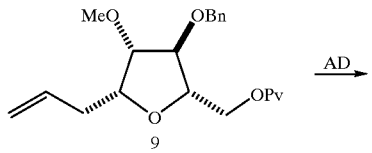

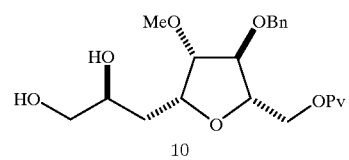

Diol 7 HCl (37% aqueous solution, 12.75 mL, 153 mmol) was added to a solution of methyl ether 6 (32.93 g, 61 mmol) in MeOH (110 mL) at rt. After 17 h, NaHCO₃ (17 g) was added to the reaction mixture. The mixture was stirred for 30 min, concentrated, suspended in EtOAc and filtered. The filtrate was concentrated and purified by flash chromatography (50% EtOAc-hexanes to EtOAc) to give diol 7 (10.0 g, 87%).

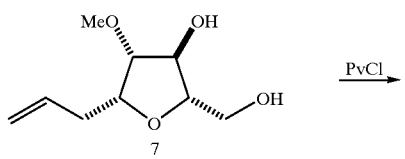

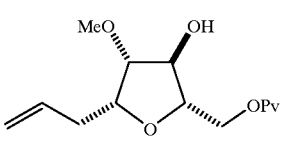

Alcohol 8 A solution of pivaloyl chloride (8.4 mL, 67 mmol) in pyridine (50 mL) was added over 1.5 h to a solution of diol 7 (12.24 g, 65 mmol) in pyridine (100 mL) at 0° C. After 1 h at 0° C. and 18 h at rt, the mixture was diluted with saturated aqueous NH₄Cl and extracted with EtOAc (3×800 mL). The combined organic layers were dried over Na₂SO₄, concentrated and purified by flash chromatography (50% EtOAc-hexanes) to furnish alcohol 8 (16.9 g, 96%).

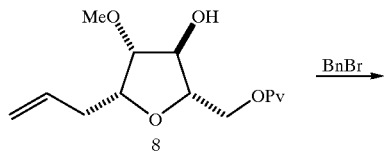

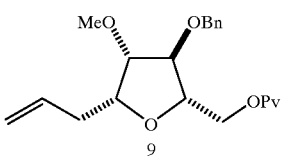

Olefin 9 Benzyl bromide (62 mL, 521 mmol) and Bu₄NHSO₄ (10.6 g, 31 mmol) were added to a solution of alcohol 8 (16.9 g, 62 mmol) in CH₂Cl₂ (100 mL) at 0° C. A solution of NaOH (9.95 g, 248 mmol) in H₂O (10 mL) was added to the reaction mixture over 15 min. After 30 min at 0° C. and 18 h at rt, the reaction mixture was diluted with saturated aqueous NH₄Cl and extracted with CH₂Cl₂ (3×100 mL). The combined organic layers were dried over Na₂SO₄, concentrated and purified by flash chromatography (hexanes to 30% EtOAc-hexanes) to afford olefin 9 (22.1 g, 98%).

Diol 10 OsO₄ (0.1 M solution in toluene, 7.3 mL, 0.73 mmol) and a solution of olefin 9 (24.9 g, 69 mmol) in t-BuOH (165 mL) were added to a solution of K₂CO₃ (31.2 g, 161 mmol), K₃Fe(CN)₆ (74.4 g, 161 mmol), (DHQ)₂PYR (1.33 g, 1.50 mmol), H₂O (500 mL) and t-BuOH (330 mL) at 0° C. After 3 h at 0° C., Na₂S₂O₅·5 H₂O (37.3 g, 150 mmol) was added. The reaction mixture was warmed to rt, stirred for 1 h and extracted with EtOAc (3×300 mL). The combined organic layers were dried over Na₂SO₄, concentrated and purified by flash chromatography (5% isopropanol-CH₂Cl₂) to provide diol 10 (17.98 g, 75%).

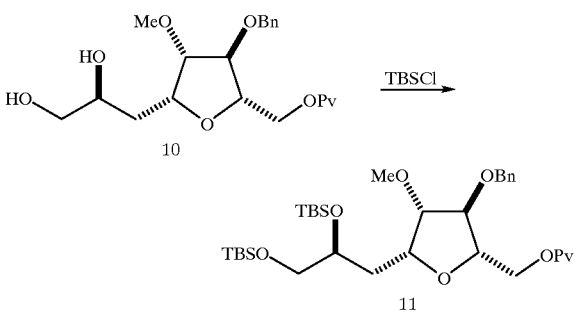

Silyl ether 11 Imidazole (21 g, 308 mmol) and TBSCl (26.5 g, 176 mmol) were added to a solution of (17.4 g, 44 mmol) in DMF (90 mL) at rt. After 18 h, the reaction mixture was diluted aqueous NaHCO₃ (250 mL), stirred for 1 h and extracted with CH₂Cl₂ (3×100 mL). The combined organic layers were dried over Na₂SO₄, concentrated and purified by flash chromatography (5% EtOAc-hexanes) to afford silyl ether 11 (25.7 g, 94%).

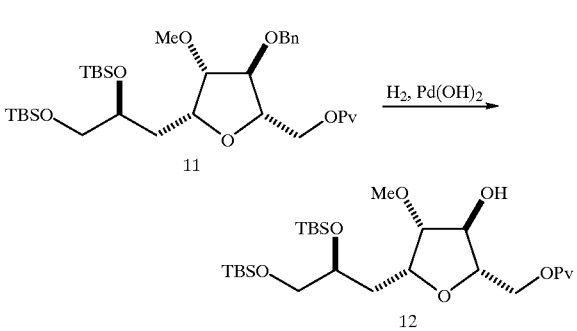

Alcohol 12 A mixture of silyl ether 11 (21.2 g, 33.8 mmol), Pd(OH)₂ (20%, 4.7 g, 33.8 mmol) and EtOAc (200 mL) was stirred at rt under 1 atm H₂ for 3 h. The mixture was filtered through Celite, concentrated and purified by flash chromatography (10% to 20% EtOAc-hexanes) to afford alcohol 12 (17.4 g, 96%).

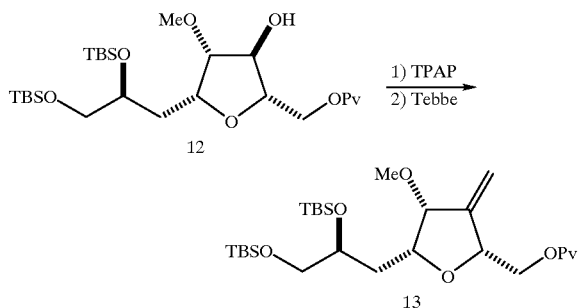

Olefin 13 4-Methyhmorpholine N-oxide (7.66 g, 65 mmol) and TPAP (1.15 g, 3.26 mmol) was added in four portions over 20 min to a solution of alcohol 12 (17.4 g, 32.5 mmol) in $CH_2Cl_2$ (145 mL) at 0° C. After 20 min, the reaction mixture was diluted with $Et_2O$ (50 mL) and saturated aqueous $Na_2S_2O_5$ (50 mL) and filtered through Celite. The organic layer was separated, washed sequentially with saturated aqueous $CuSO_4$-brine (1:1) and brine, dried over $Na_2SO_4$, filtered through Celite, and concentrated to afford the desired crude ketone.

Tebbe reagent was prepared by stilling bis (cyclopentadienyl)titanium (11.36 g, 45.6 mmol) and $Me_3Al$ (2.0 M in toluene, 45.6 mL, 91.2 mmol) for 4 days at rt. This material was cooled to −25° C. and a solution of crude ketone in THF (150 mL) was added. The reaction mixture was warmed to 0° C., stirred for 30 min, quenched by slow addition of 0.1 N NaOH (3.5 mL), and then stirred for an additional 20 min at rt. The mixture was diluted with $Et_2O$, filtered through Celite and concentrated. The residue was dissolved in $CH_2Cl_2$, filtered through basic $Al_2O_3$, concentrated and purified by flash chromatography (5% EtOAc-hexanes) to give olefin 13 (12.8 g, 74% for two steps).

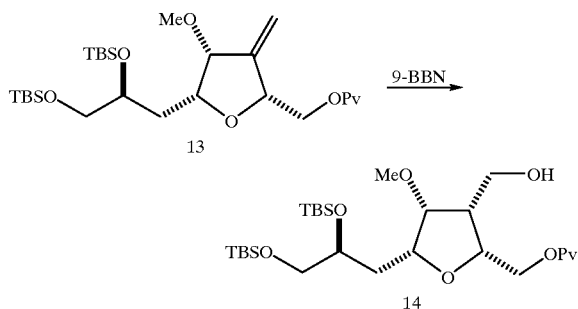

Alcohol 14 9-BBN (0.5 M in THF, 165 mL, 83 mmol) was added to a solution of olefin 13 (12.78 g, 24 mmol) in THF (280 mL) at 0° C. After stirring for 5 h at rt, the reaction mixture was recooled to 0° C. at which time $H_2$) (200 mL), THF (100 mL) and $NaBO_3.4 H_2O$ (75 g) were added. The mixture was warmed to rt, stirred for 16 h and then concentrated. The aqueous residue was extracted with EtOAc (4×300 mL) and the combined organic layers were dried over $Na_2SO_4$. Concentration and purification by flash chromatography (20% to 35% EtOAc-hexanes) afforded alcohol 14 (12.05 g, 91%).

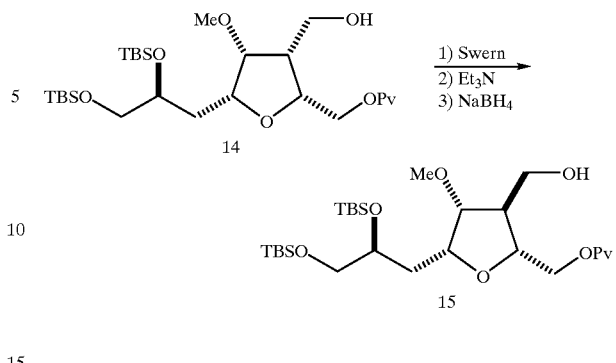

Alcohol 15 DMSO (9 mL, 127 mmol) was added to a solution of oxalyl chloride (5.6 mL, 64 mmol) in $CH_2Cl_2$ (350 mL) at −78° C. After stirring for 15 min, a solution of alcohol 14 (11.7 g, 0.021 mmol) in $CH_2Cl_2$ (50 mL) was added and stirring was continued for 1 h, after which $Et_3N$ (26.7 mL, 192 mmol) was added. The reaction mixture was warmed to 0° C., stirred for 15 min, diluted with saturated aqueous $NH_4Cl$, and extracted with $CH_2Cl_2$ (3×200 mL). The combined organic layers were dried over $Na_2SO_4$ and concentrated to furnish the desired crude aldehyde.

This material was dissolved in $CH_2Cl_2$ (200 mL) and treated with $Et_3N$ (20 mL) at rt. After stirring overnight, the reaction mixture was diluted with saturated aqueous $NH_4Cl$ and extracted with $CH_2Cl_2$ (3×200 mL). The combined organic layers were dried over $Na_2SO_4$, concentrated and filtered through a short $SiO_2$ column (20% EtOAc-hexanes) to afford the crude epimerized product.

The aldehyde was dissolved in $Et_2O$-EtOH (1:1, 100 mL), cooled to 0° C. and treated with sodium borohydride (1.21 g, 32 mmol). The mixture was stirred for 20 min, carefully diluted with saturated aqueous $NH_4Cl$, stirred for 30 min at rt and extracted with $CH_2Cl_2$ (3×150 mL). The combined extracts were dried over $Na_2SO_4$, concentrated and purified by flash chromatography (20% EtOAc-hexanes) to afford alcohol 15 (9.95 g, 85% for three steps).

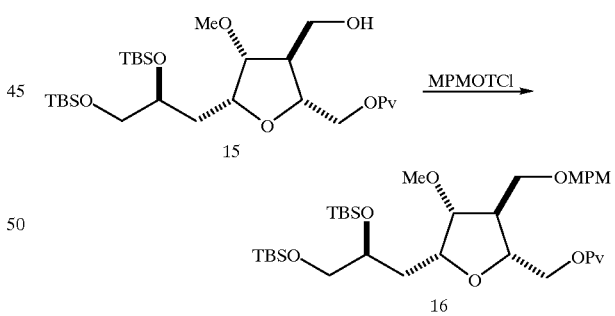

MPM-ether 16 $BF_3.OEt_2$ (0.1 M in $CH_2Cl_2$, 1.8 mL, 0.18 mmol) was added to a solution of alcohol 15 (9.87 g, 18 mmol), MPM-trichloroimidate (4.9 mL, 27 mmol) and $CH_2Cl_2$ (175 mL) at 0° C. After 40 min, a second portion of $BF_3$-$OEt_2$ (0.1 M in $CH_2Cl_2$, 0.9 mL, 0.09 mmol) was added to the reaction mixture. After 20 min, the reaction was quenched with saturated aqueous $NH_4Cl$, stirred for 1 h at rt and diluted with $Et_2O$ (600 mL). The organic layer was separated and the aqueous layer was extracted with $Et_2O$ (150 mL). The combined organic extracts were washed sequentially with 0.1 N aqueous NaOH, saturated aqueous $NaHCO_3$, brine, dried over $Na_2SO_4$, concentrated and purified by flash chromatography (20% EtOAc-hexanes) to give MPM-ether 16 (10.20 g, 85%).

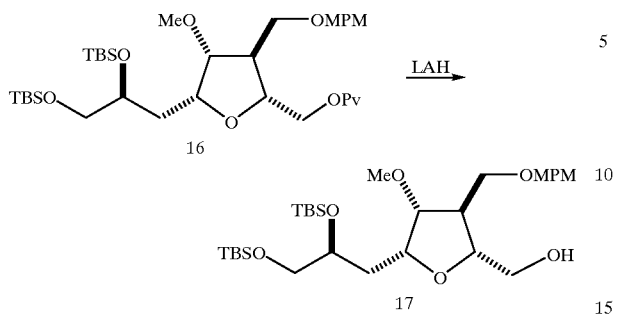

Alcohol 17 LAH (1 M in THF, 22.5 mL, 22.5 mmol) was added to a solution of MPM-ether 16 (10.05 g, 15 mmol) in Et$_2$O (1.0 L) at 0° C. After 30 min, the reaction was cautiously quenched with H$_2$O (1.3 mL), and 1 N aqueous NaOH (1.3 mL). After stirring for 1 h at rt, the suspension was filtered through Celite, concentrated and purified by flash chromatography (20% EtOAc-hexanes) to afford alcohol 17 (8.18 g, 93%).

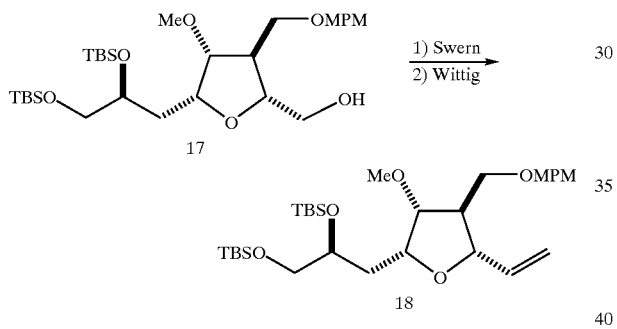

Olefin 18 DMSO (5.8 mL, 82.4 mmol) was added to a solution of oxalyl chloride (3.6 mL, 41.2 mmol) in CH$_2$Cl$_2$ (100 mL) at −78° C. After 15 min, a solution of alcohol 17 (7.94 g, 13.5 mmol) in CH$_2$Cl$_2$ (35 mL) was added to the reaction mixture. After stirring for 1 h, Et$_3$N (17 mL, 122 mmol) was added, the mixture was warmed to 0° C., stirred for 20 min, diluted with saturated aqueous NH$_4$Cl and then extracted with CH$_2$Cl$_2$ (3×100 mL). The combined organic extracts were dried over Na$_2$SO$_4$, concentrated and filtered through a short SiO$_2$ column (20% EtOAc-hexanes) to furnish the desired crude aldehyde.

n-BuLi (1.6 M, 20 mL, 30 mmol) was added dropwise to a solution of CH$_3$PPh$_3$Br (10.1 g, 30 mmol) in THF (350 mL) and DMSO (100 mL) at 0° C. After 1 h, a solution of the crude aldehyde in THF (50 mL) was added. The reaction mixture was warmed to rt and stirred for 3 h. Saturated aqueous NH$_4$Cl was added and the mixture was extracted with EtOAc (3×500 mL). The combined extracts were washed with brine, dried over Na$_2$SO$_4$, concentrated and purified by flash chromatography (7% EtOAc-hexanes) to afford olefin 18 (5.57 g, 71% yield for 2 steps).

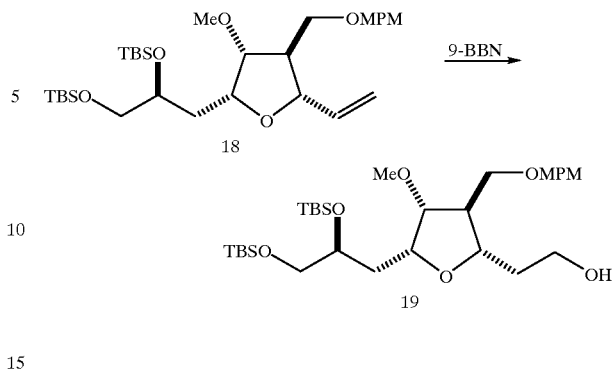

Alcohol 19 9-BBN (0.5 M in THF, 65 mL, 33 mmol) was added to a solution of olefin 18 (5.56 g, 9.6 mmol) in THF (85 mL) at 0° C. The mixture was stirred for 5 h at rt and then recooled to 0° C. H$_2$O (200 mL), THF (100 mL), and NaBO$_3$.4 H$_2$O (30 g) were sequentially added. After stirring overnight at rt, the organic volatiles were removed under reduced pressure. The aqueous residue was extracted with EtOAc (3×200 mL) and the combined organic layers were dried over Na$_2$SO$_4$. Concentration and purification by flash chromatography (30% EtOAc-hexanes) afforded alcohol 19 (12.05 g, 92%).

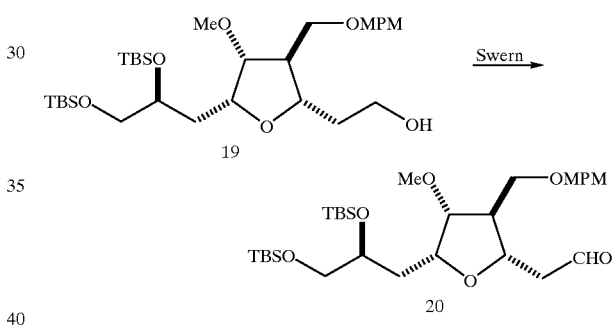

Aldehyde 20 DMSO (1.36 mL, 19.2 mmol) was added dropwise over 4 min to a solution of oxalyl chloride (1.26 mL, 14.4 mmol) in CH$_2$Cl$_2$ (120 mL) at −78° C. After stirring for 10 min, a solution of alcohol 19 (5.76 g, 9.61 mmol) in CH$_2$Cl$_2$ (20 mL) was added via cannula. The transfer was completed by rinsing with additional CH$_2$Cl$_2$ (2×5 mL). After stirring for 20 min, the mixture was treated with Et$_3$N (5.36 mL, 38.4 mmol) and stirred for 10 min at −78° C., 30 min at 0° C. and 10 min at rt. The reaction mixture was poured into saturated aqueous NaHCO$_3$ (200 mL) and the separated aqueous layer was extracted with CH$_2$Cl$_2$ (3×) followed by EtOAc (100 mL). The combined organic phases were dried over Na$_2$SO$_4$, concentrated and purified by column chromatography (10% to 20% EtOAc-hexanes) to furnish aldehyde compound 20 (5.28 g, 92%) as an oil.

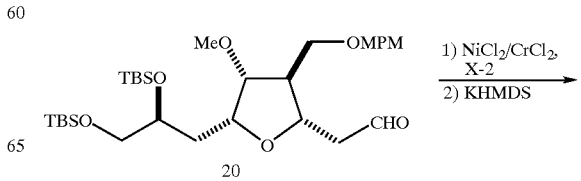

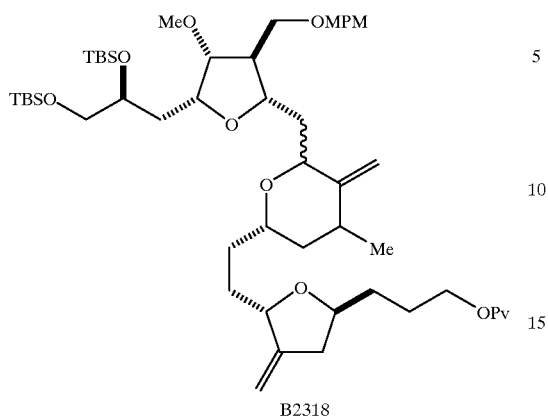

B2318

B2318 0.1% NiCl$_2$/CrCl$_2$ (w/w, 3.21 g) and 1% NiCl$_2$/CrCl$_2$ (w/w, 4.31 g) was added to a solution of aldehyde 20 (3.73 g, 6.25 mmol), key fragment F-2 exemplified by vinyl iodide X2. (5.10 g, 9.16 mmol), THF (85 mL) and DMF (21 mL) at rt in a glove box. The reaction mixture was stirred for 24 h, removed from the glove box, cooled to 0° C., diluted with EtOAc (100 mL), quenched with saturated NH$_4$Cl (200 mL) and stirred for 30 min. The separated aqueous phase was extracted with EtOAc (6×) and the combined organic layers were dried over Na$_2$SO$_4$ concentrated and purified by column chromatography (20% to 30%) to give B2318 (~3 g) contaminated with close running impurities and the uncyclized intermediate (4.61 g). The latter (4.61 g, 4.48 mmol,) was dissolved in THF (150 mL), cooled to 0° C. and treated with KHMDS (0.5 M in toluene, 14 mL, 7.0 mmol) over a 2 min period. After stirring at 0° C. for 15 min, the reaction was quenched with saturated aqueous NH$_4$Cl (150 mL) and warmed to rt. The separated aqueous layer was extracted with EtOAc (3×) and the combined organic phases were dried over Na$_2$SO$_4$, concentrated and combined with the partially purified product obtained above. Column chromatography (10% EtOAc-hexanes) afforded B2318 (3.17 g, 55%) as an inseparable ~3:1 mixture of C27 diastereomers.

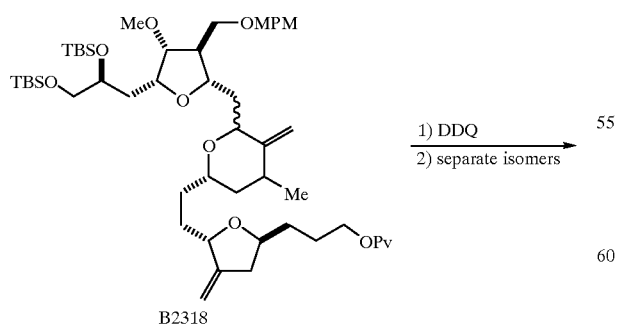

B2318

1) DDQ
2) separate isomers

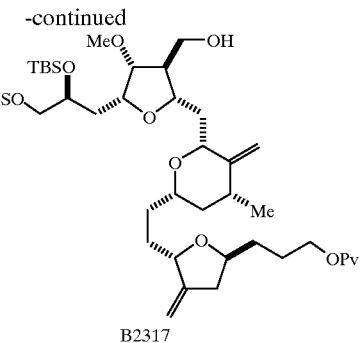

B2317

B2317 DDQ (1.45 g, 6.42 mmol) was added portion-wise over 30 min to a stirred solution of B2318 (3.12 g, 3.35 mmol) in CH$_2$Cl$_2$ (50 mL) and pH 7 phosphate buffer (5 mL) at rt. The reaction was quenched with saturated aqueous NaHCO$_3$ (50 mL), stirred for 5 min, diluted with additional saturated aqueous NaHCO$_3$ (100 mL), H$_2$O (200 mL) and extracted with Et$_2$O (5×). The combined organic phases were dried over Na$_2$SO$_4$, concentrated and purified by column chromatography (15% to 30% EtOAc-hexanes) to give recovered B2318 (1.40 g) and a mixture of the C27 isomeric products. The recovered B2318 was resubmitted to the reaction conditions described above to afford additional product. Recovered starting material was again cycled through the deprotection conditions. All of the desired material was combined and separated by MPLC to afford B2317 (1.65 g, 61%).

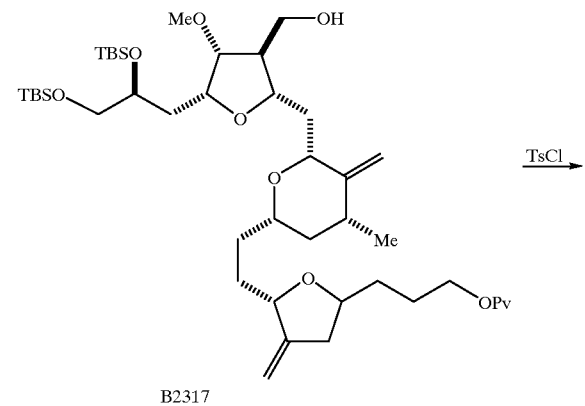

B2317

TsCl →

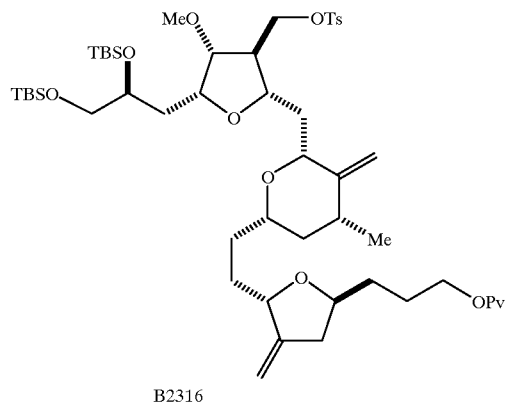

B2316

B2316 TsCl (0.63 g, 3.30 mmol) was added to a solution of B2317 (1.60 g, 1.97 mmol) in CH$_2$Cl$_2$ (8 mL) and pyridine (2 mL) at rt. After stirring for 29 h, the reaction was quenched with saturated aqueous NaHCO$_3$ (30 mL) and H$_2$O (10 mL). The separated aqueous layer was extracted with Et$_2$O and the combined organic layers were dried over Na$_2$SO$_4$, concentrated and purified by column chromatography (15% to 30% EtOAc-hexanes) to give B2316 (2.01 g, 92%) as an oil along with recovered B2317 (92 mg, 5.8%).

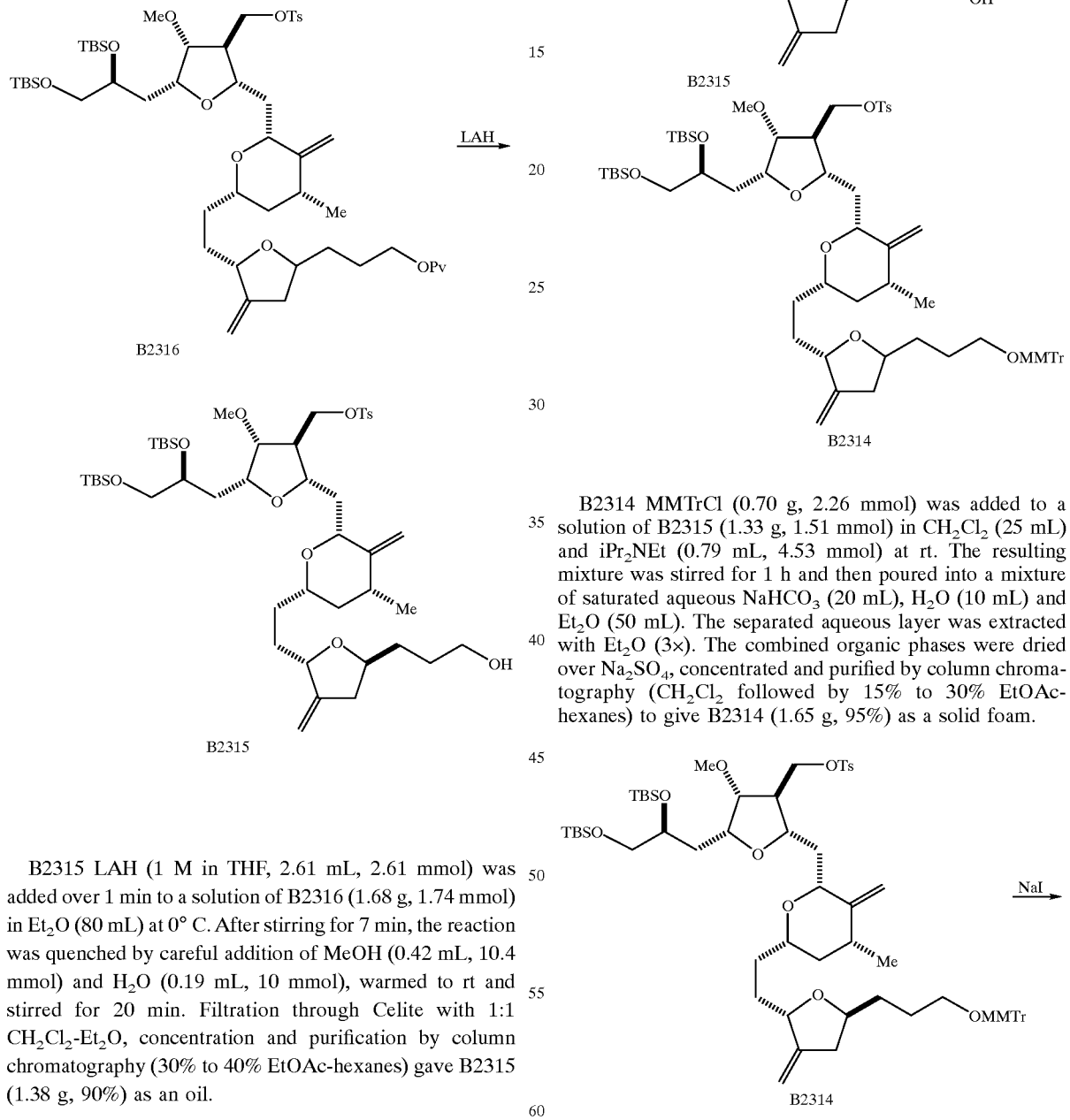

B2315 LAH (1 M in THF, 2.61 mL, 2.61 mmol) was added over 1 min to a solution of B2316 (1.68 g, 1.74 mmol) in Et$_2$O (80 mL) at 0° C. After stirring for 7 min, the reaction was quenched by careful addition of MeOH (0.42 mL, 10.4 mmol) and H$_2$O (0.19 mL, 10 mmol), warmed to rt and stirred for 20 min. Filtration through Celite with 1:1 CH$_2$Cl$_2$-Et$_2$O, concentration and purification by column chromatography (30% to 40% EtOAc-hexanes) gave B2315 (1.38 g, 90%) as an oil.

B2314 MMTrCl (0.70 g, 2.26 mmol) was added to a solution of B2315 (1.33 g, 1.51 mmol) in CH$_2$Cl$_2$ (25 mL) and iPr$_2$NEt (0.79 mL, 4.53 mmol) at rt. The resulting mixture was stirred for 1 h and then poured into a mixture of saturated aqueous NaHCO$_3$ (20 mL), H$_2$O (10 mL) and Et$_2$O (50 mL). The separated aqueous layer was extracted with Et$_2$O (3×). The combined organic phases were dried over Na$_2$SO$_4$, concentrated and purified by column chromatography (CH$_2$Cl$_2$ followed by 15% to 30% EtOAc-hexanes) to give B2314 (1.65 g, 95%) as a solid foam.

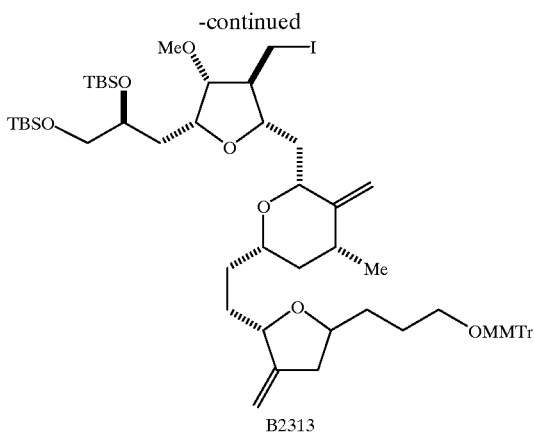

B2313

B2313 A mixture of B2314 (1.60 g, 1.39 mmol) and NaI (3.10 g, 20.8 mmol) in acetone (50 mL) was heated under reflux for 13 h. After cooling to rt, the reaction mixture was diluted with EtOAc, and concentrated. H$_2$O (5 mL), brine (20 mL) and Na$_2$S$_2$O$_3$ (200 mg) were added and the resulting mixture was extracted with Et$_2$O (4×). The combined extracts were dried over Na$_2$SO$_4$, concentrated and purified by column chromatography (10% EtOAc-hexanes) to give B2313 (1.50 g, 97%) as an oil.

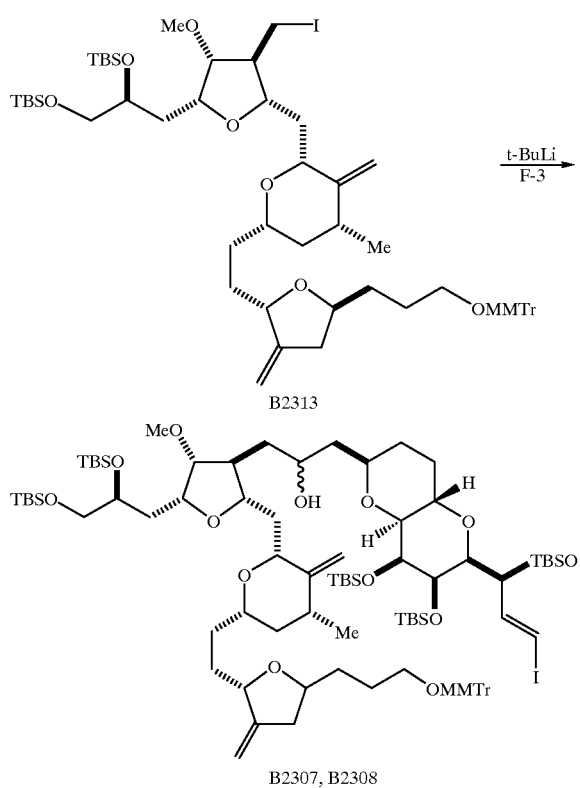

B2313

B2307, B2308

B2308 Tert-BuLi (1.7 M in pentane, 1.00 mL, 1.7 mmol) was added over 1 min to a solution of B2313 (0.90 g, 0.81 mmol) in Et$_2$O (14 mL) at −78° C. After stirring for 9 min, the mixture was transferred via cannula over 4 min to a solution of key fragment F-3 (0.83 g, 1.14 mol) in Et$_2$O (4 mL) at −78° C. The transfer was completed by rinsing with additional Et$_2$O (2 mL). The resultant mixture was stirred at −78° C. for 5 min and then at 0° C. for 10 min, quenched with saturated aqueous NaHCO$_3$ (30 mL) and warmed to rt. The separated aqueous layer was extracted with Et$_2$O (3×) and the combined organic phases were dried over Na$_2$SO$_4$ and concentrated. The residue was combined with those of other two batches (corresponding to 0.11 g and 0.44 g of B2313) and purified by column chromatography (10% to 20% EtOAc-hexanes) to give a mixture of B2307 and B2308 (1.86 g, 83%) as a solid foam. Although the isomers could be separated by prep TLC (20% EtOAc-hexanes), they were carried forward as a mixture.

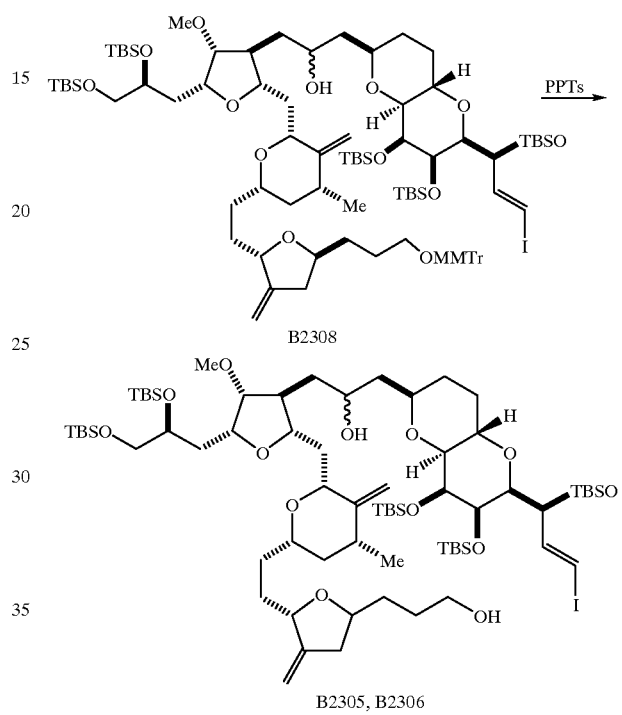

B2308

B2305, B2306

B2305 and B2306 The mixture of B2307/B2308 (1.80 g, 1.05 mmol) was dissolved in EtOH (20 mL), treated with PPTS (10.0 mg, 0.04 mmol), stirred at rt for 11 h and then quenched with NaHCO$_3$ (20.0 mg, 0.24 mmol). After stirring for 15 min, the mixture was concentrated, azeotroped with toluene (15 mL), and purified by column chromatography (20% to 30% EtOAc-hexanes) to give a mixture of B2305 and B2306 (1.22 g, 81%) as a solid foam. Although the isomers could be separated by prep TLC (30% EtOAc-hexanes), they were carried forward as a mixture.

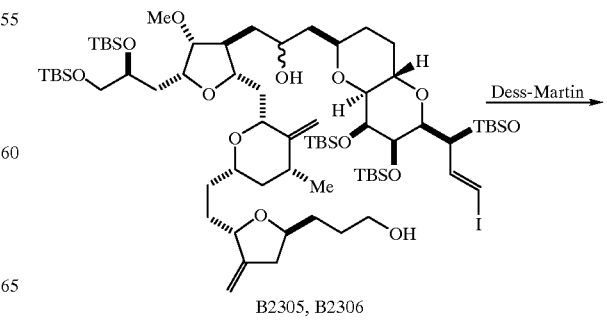

B2305, B2306

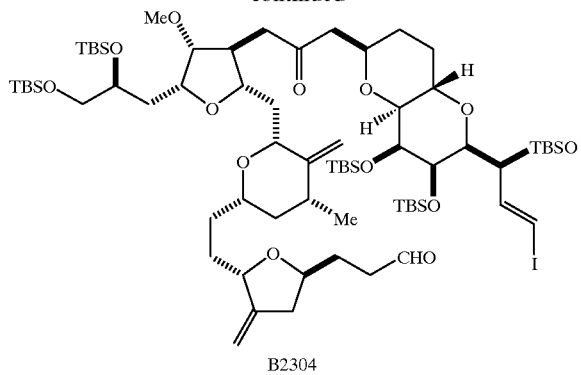

B2304

B2304 A mixture of B2305/B2306 (1.16 g, 0.68 mmol), and Dess-Martin periodinane (0.61 g, 1.44 mmol) in $CH_2Cl_2$ (35 mL) was stirred at rt for 1 h. Additional Dess-Martin periodinane (0.54 g, 1.27 mmol) was added to the mixture and stirring was continued for an additional 1 h. The mixture was diluted with $Et_2O$ (100 mL), stirred for 20 min and filtered through Celite with $Et_2O$. The colorless filtrate was washed with saturated aqueous $NaHCO_3$ (100 mL) and the separated aqueous layer was extracted with $Et_2O$ (3×). The combined organic phases were dried over $Na_2SO_4$, concentrated and purified by column chromatography (10% to 15% EtOAc-hexanes) to give B2304 (0.98 g, 84%) as a solid foam.

Alternatively, B2304 may be prepared as follows and in fact the synthesis described below is superior to that given above.

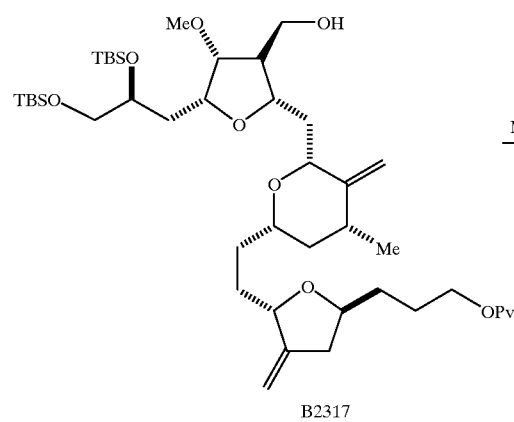

B2317

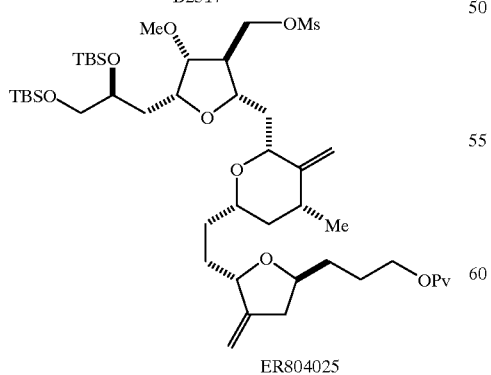

ER804025

To a solution of the alcohol, 2.4 g mg, in methylene chloride, 29 mL, was added triflic anhydride, 770 mg. The mixture was stirred for 15 minutes, extracted with saturated sodium bicarbonate, dried and chromatrographed to give 2.737 g, 100%.

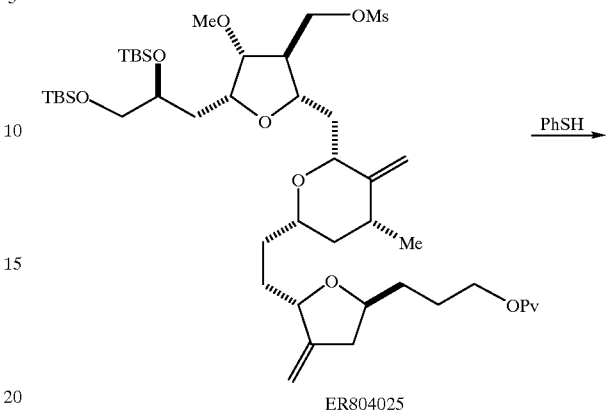

ER804025

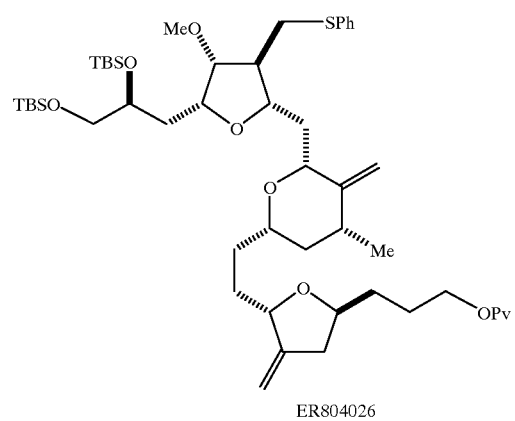

ER804026

To a solution of the mesylate, 405 mg, in DMF, 0.06 mL, was added diisopropylethylamine, 0.130 mL, followed by benzenethiol, 0.061 mL. After 4 hours and after 22 hours, additional amine, 0.03 mL, and benzenethiol, 0.015 mL, were added. After 24 hours, the mixture was diluted with 5% ethyl acetate/hexane, I mL and chromatographed to give 409 mg.

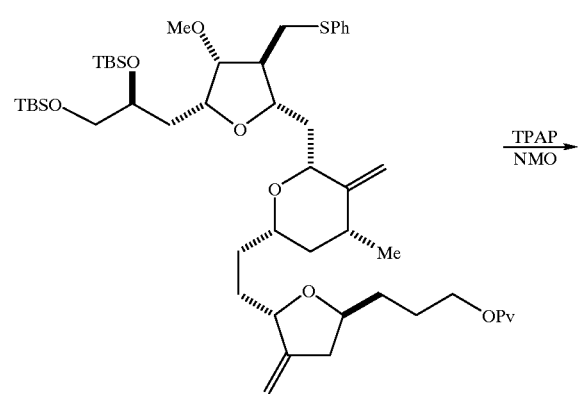

ER804026

-continued

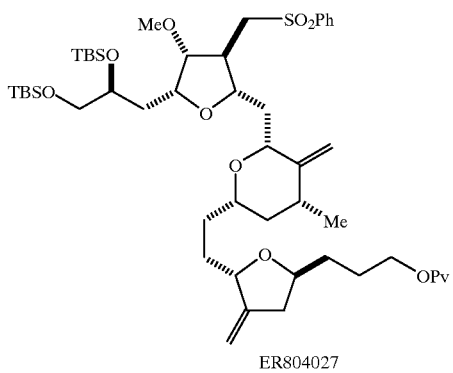
ER804027

To a solution of the sulfide, 1.97 g, in acetonitrile, 16 mL, was added N-methylmorpholine oxide (NMO), and then a solution of 1.02 g, tetrapropylammonium perruthenate(VII), (TPAP), 38 mg, in acetonitrile, 1 mL. After 3.5 hours at room temperature, the mixture was heated to 40° C. for 1 hour. The mixture was cooled and aqueous satd. Sodium thiosulfate was added and the mixture partitioned between water and ethyl acetate. The usual work-up gave 1.567 g of a brown oil.

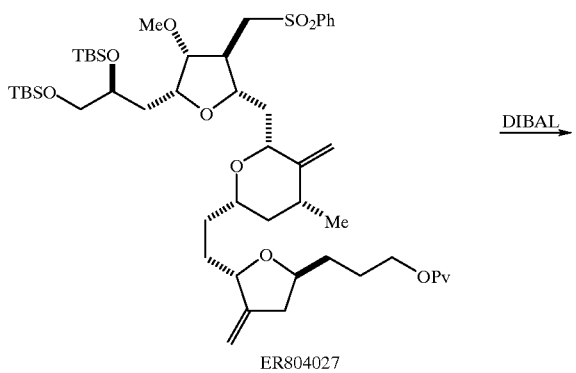
ER804027

To a solution of the pivaloate ester, 1.567 g, in methylene chloride, 11.2 mL, at −78° C. in was added DIBAL, 2.5 mL of a 1 M solution in toluene. After 15 minutes, additional DIBAL, 0.8 mL, was added. After an additional 5 minutes, methanol, 0.46 mL, was slowly added followed by water, 0.2 mL. The mixture was filtered through Celite and chromatographed to give 1.386 g of an oil.

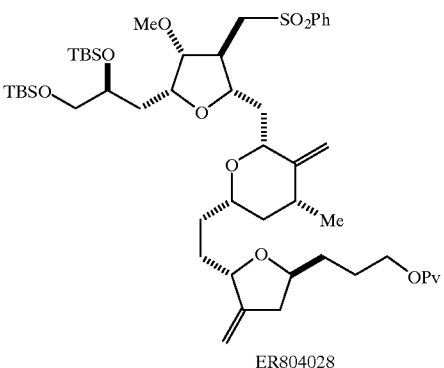
ER804028

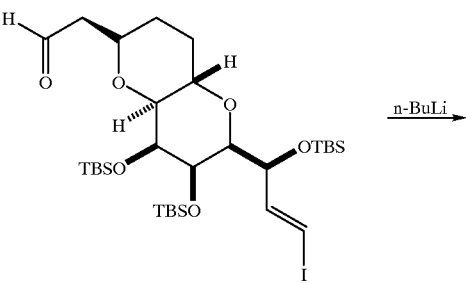
F-3

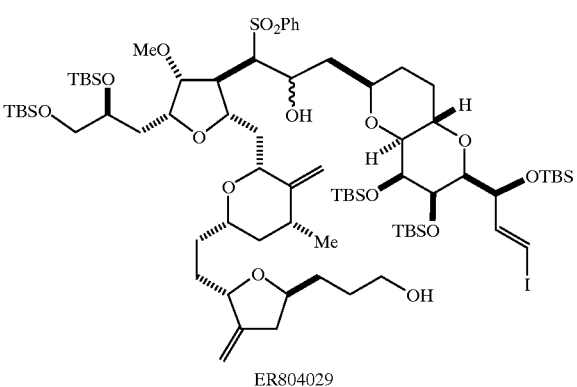
ER804029

To a solution of the sulfone, 36 mg, in DME, 1 mL, at −40° C. was added n-butyllithium, 2.8 equivalents. After 35 minutes, a solution of the aldehyde, 42 mg, in DME, 0.5 mL) was added. After 40 minutes, saturated aqueous ammonium chloride was added and the mixture extracted with ethyl acetate. The usual work-up, followed by chromatography gave 52 mg of an oil.

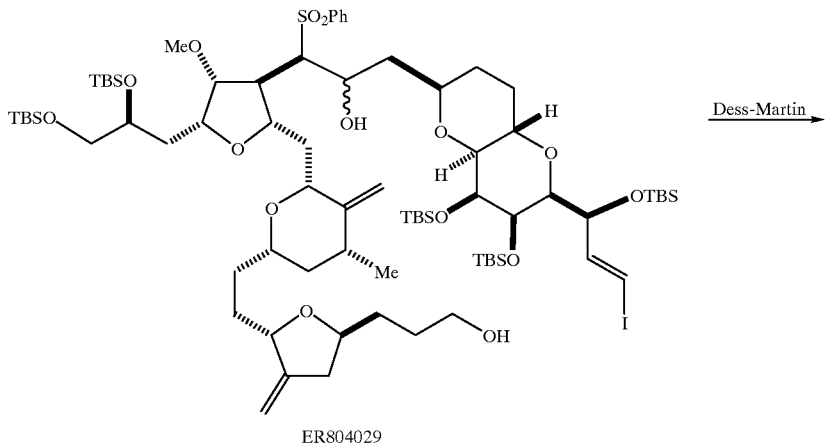

ER804029

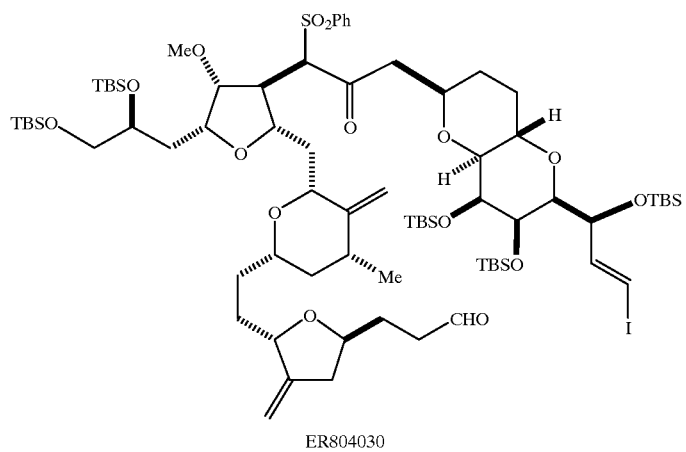

ER804030

To a solution of the alcohol, 42 mg, in methylene chloride, 2 mL, was added the Dess Martin reagent, 36.4 mg. The mixture was stirred for 30 minutes and ether was added. The mixture was filtered through Celite, washed with saturated sodium bicarbonate, with saturated sodium thiosulfate, worked up in the usual way and chromatographed to give 38 mg of an oil.

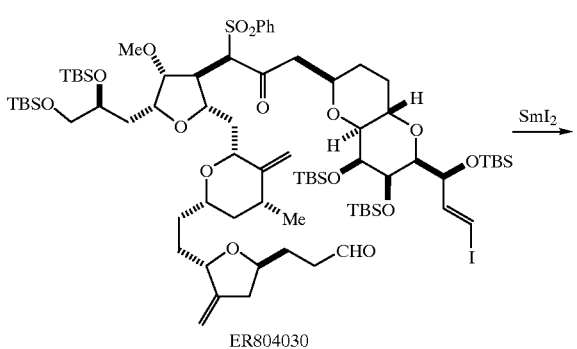

ER804030

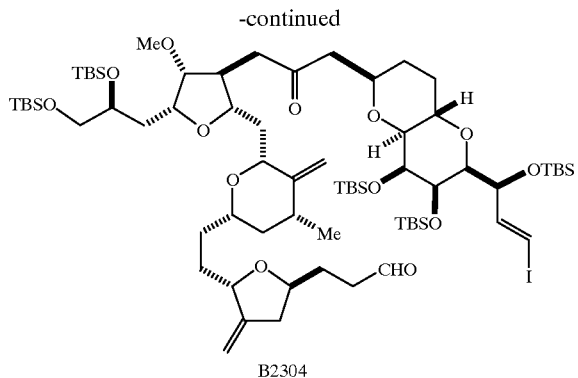

B2304

Preparation of $SmI_2$ Solution

A solution of 1,2-diiodoethane in 10 mL of THF was added to a suspension of Sm, 0.16 g, in THF, 1 mL. The mixture was stirred for 1 hour.

An aliquot of this solution, 0.03 mL, was added to a solution of the sulfone in THF at −78° C. After 5 minutes, additional SmI reagent, 0.05 mL, as added. After a few additional minutes, more reagent, 0.25 mL, was added. The cooling bath was removed and saturated aqueous sodium bicarbonate, 3 mL, was added. The mixture was partitioned between ether and water and the usual work-up gave 9.1 mg, 81%, of an oil.

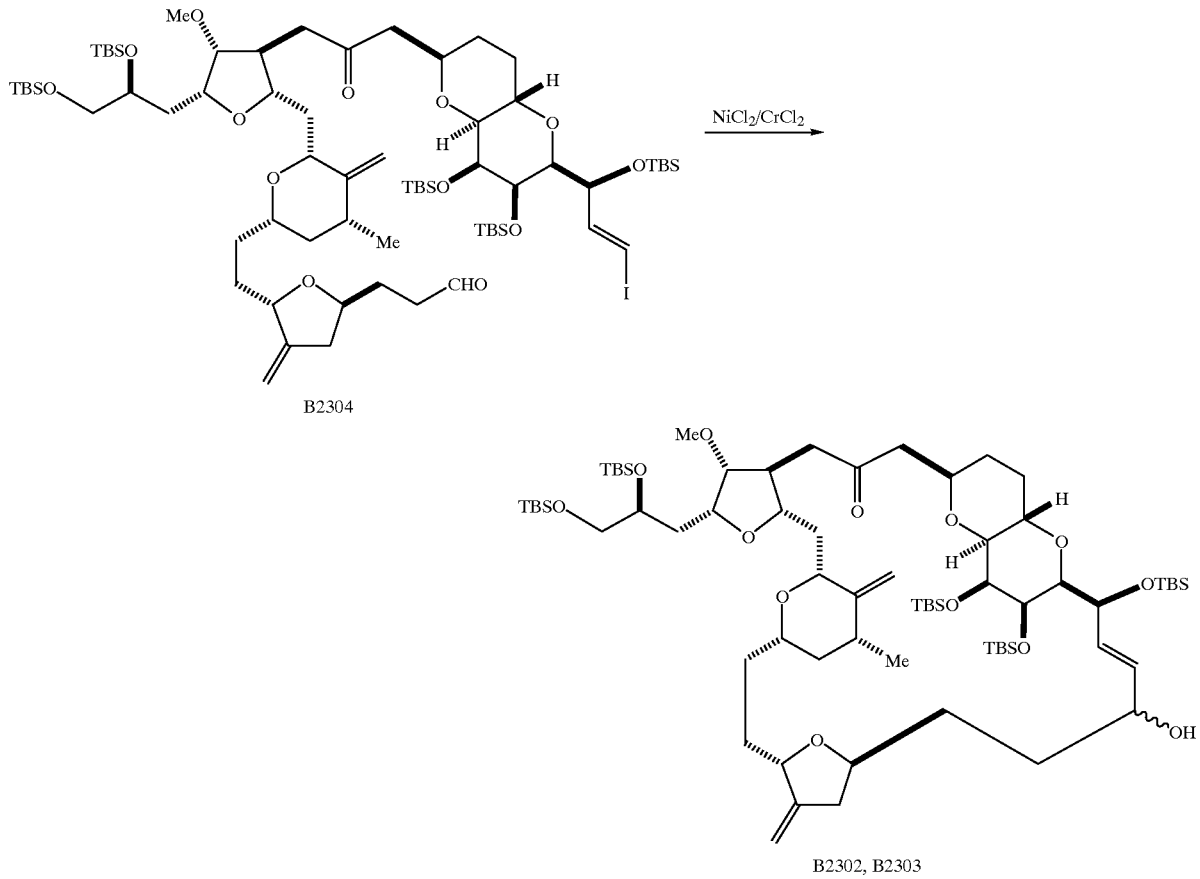

B2302 and B2303 In a glove box, NiCl$_2$/CrCl$_2$ (1% w/w, 1.09 g, 8.86 mmol) was added to a solution of B2304 (1.01 g, 0.70 mmol) in THF (600 mL) and DMF (150 mL) at rt. After stirring for 2 days the reaction mixture was taken out of the glove box, cooled to 0° C., quenched with saturated aqueous NH$_4$Cl (300 mL) and stirred at 0° C. for 20 min. After addition of H$_2$O (100 mL), the two layers were separated and the aqueous layer was extracted with EtOAc (5×). The combined organic phases were washed with brine, dried over Na$_2$SO$_4$, concentrated and purified by column chromatography (15% EtOAc-hexanes) to furnish a mixture of B2302 and B2303 (0.84 g, 92%) as a solid foam. Although the isomers could be separated by prep TLC (20% EtOAc-hexanes), they were carried forward as a mixture.

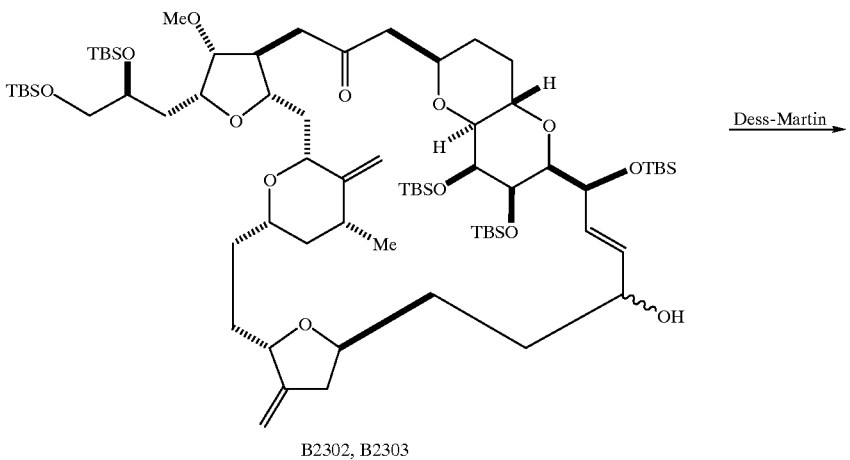

-continued

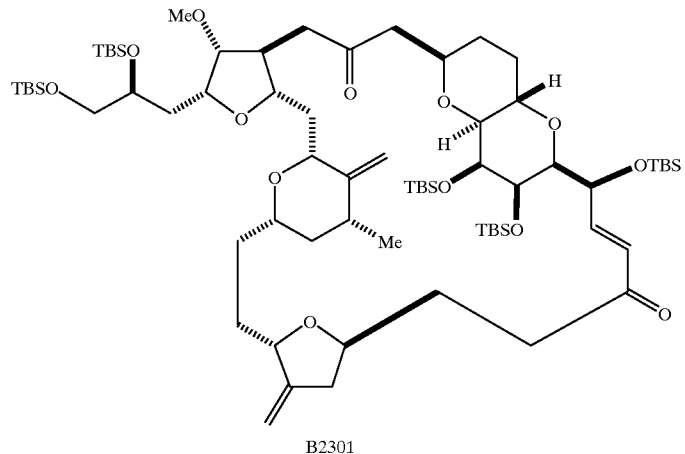
B2301

B2301 A mixture of B2302/B2303 (0.79 g, 0.60 mmol) and Dess-Martin periodinane (0.26 g, 0.60 mmol) in CH$_2$Cl$_2$ (30 mL) at rt was stirred for 30 min. Additional Dess-Martin periodinane (0.26 g, 0.60 mmol) was added to the mixture and stirring was continued for additional 1.5 h. The mixture was then diluted with Et$_2$O (100 mL), stirred for 15 min and filtered through Celite. The filtrate was washed with saturated aqueous NaHCO$_3$ (100 mL) and the separated aqueous layer was extracted with Et$_2$O (3×). The combined organic phases were dried over Na$_2$SO$_4$, concentrated and purified by column chromatography (10% to 15% EtOAc-hexanes) to give B2301 (0.67 g, 85%) as an oil.

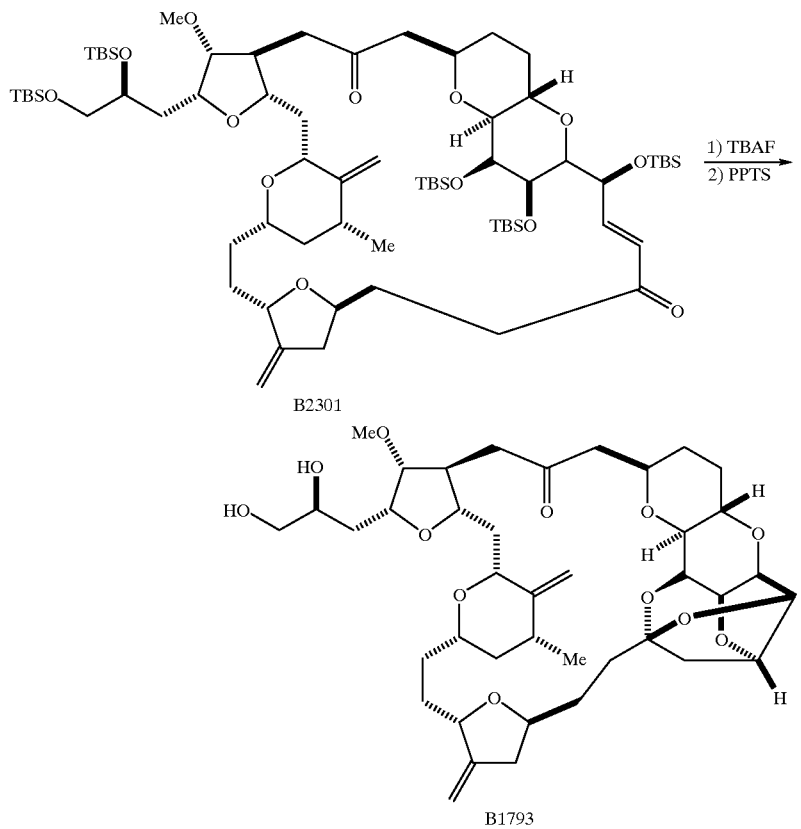

B1793 TBAF (1 M in THF containing 0.5M imidazole HCl, 4.60 mL, 4.60 mmol) was added over 2 min to a solution of B2301 (0.62 g, 0.48 mmol,) in THF (29 mL) at rt and the resulting mixture was stirred for 18 h. After dilution with hexanes (10 mL), the reaction mixture was directly loaded onto a SiO$_2$ column packed with 50% EtOAc-hexanes and eluted with 50% EtOAc-hexanes (1 L) followed by 10% MeOH/EtOAc to collect a mixture of intermediates. After solvent removal, the residue was dissolved in CH$_2$Cl$_2$ (15 mL) and treated with PPTS (645 mg). After stirring for 1 h at rt, additional PPTS (414 mg) was added and the resulting white suspension was stirred for 4.5 h. The reaction mixture was then directly loaded onto a SiO$_2$ column packed with 70% EtOAc-hexanes and eluted with 70% EtOAc/hexanes (0.5 L), EtOAc (1 L). Elution with 5% to 10% MeOH/EtOAc furnished pure B1793 (181 mg) and elution with 15% MeOH-EtOAc gave additional semi-pure product, which after purification by preparative TLC (10% MeOH-EtOAc) provided additional pure B1793 (42 mg). B1793 (total 223 mg, 64%) was obtained as a white solid. HRMS: calcd for C$_{40}$H$_{58}$O$_{12}$+Na 753.3826. Found: 753.3808.

Synthesis of B1794:

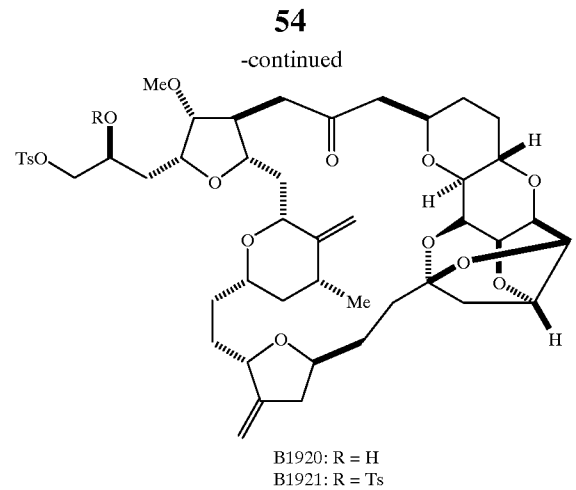

B1920: R = H
B1921: R = Ts

B1920 and B1921 TsCl (9.9 mg, 0.052 mmol) was added to a solution of diol B1793 (7.6 mg, 0.010 mmol) in CH$_2$Cl$_2$ (1 mL) and pyridine (0.1 mL) at rt. After 48 h, the reaction was quenched with a 1:4 mixture of saturated aqueous NaHCO$_3$-brine and extracted with CH$_2$Cl$_2$ (4×). The combined extracts were dried over Na$_2$SO$_4$ and concentrated. Purification by preparative TLC (80% EtOAc-hexanes) afforded monotosylate B1920 (6.0 mg, 67%), and ditosylate B1921 (1.8 mg, 18%).

B1794 Except for stereochemical and protecting group differences (Schemes 3 and 5), arabinose was converted to B1794 in a manner similar to that described for B1793 (see schemes 4 and 5). HRMS: calcd for C$_{40}$H$_{58}$O$_{12}$+Na 753.3826. Found: 753.3856.

Synthesis of Representative B17 Analogs:

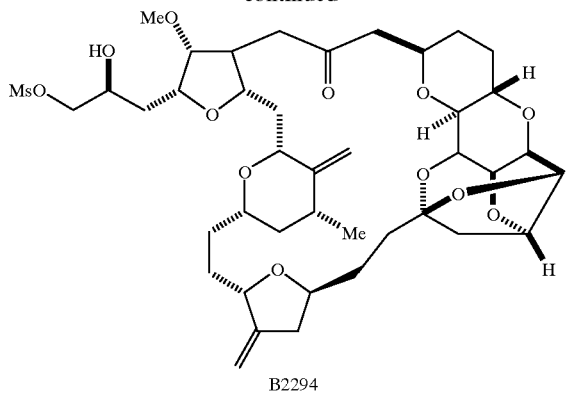

B2294

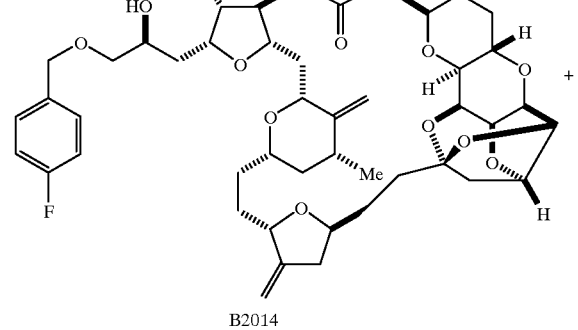

B2014

B2294 MsCl (0.3 M in $CH_2Cl_2$, 98 μL, 0.030 mmol) was added dropwise over 40 min to a mixture of collidine (7 μL, 0.054 mmol), B1793 (20.8 mg, 0.028 mmol) and $CH_2Cl_2$ (1 mL) at 0° C. After 76 h at 4° C., the reaction was quenched with a 1:4 mixture of saturated aqueous $NaHCO_3$-brine and extracted with $CH_2Cl_2$ (4×). The combined extracts were dried over $Na_2SO_4$ and concentrated. The crude product was dissolved in toluene (3 mL) concentrated and purified by preparative TLC (1.5% MeOH-EtOAc) to afford mesylate B2294 (21.4 mg, 95%).

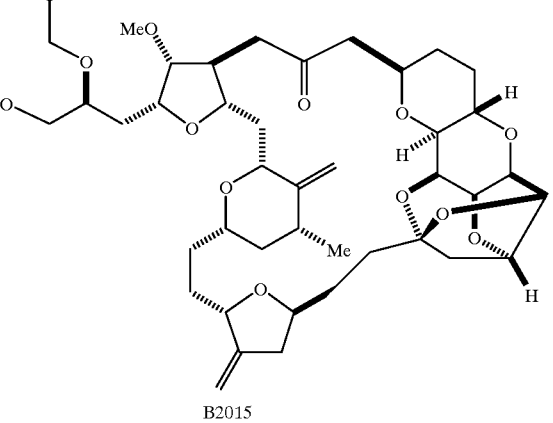

B2015

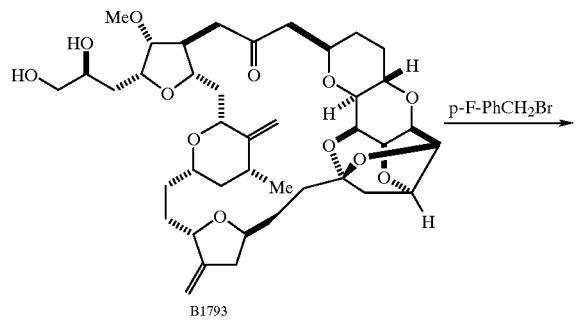

B1793 p-F-PhCH$_2$Br →

B2014 and B2015 A 0.016 solution of 4-fluorobenzyl bromide in $Et_2O$ (800 μL, 13 μmol) and $Ag_2O$ (10 mg, 43 μmol) were each added in three portions at 1 h intervals to a rt solution of B1793 (1.7 mg, 2.3 μmol) in $Et_2O$ (1.2 mL). The mixture was protected from light, stirred for 7 h and then filtered through Celite. Concentration and purification by preparative TLC (EtOAc) afforded primary ether B2014 (1.1 mg, 56%), and secondary ether B2015 (0.6 mg, 31%). HRMS (FAB): calcd for $C_{47}H_{63}FO_{12}$+Na 861.4201. Found: for B2014 861.4178, for B2015 861.4160.

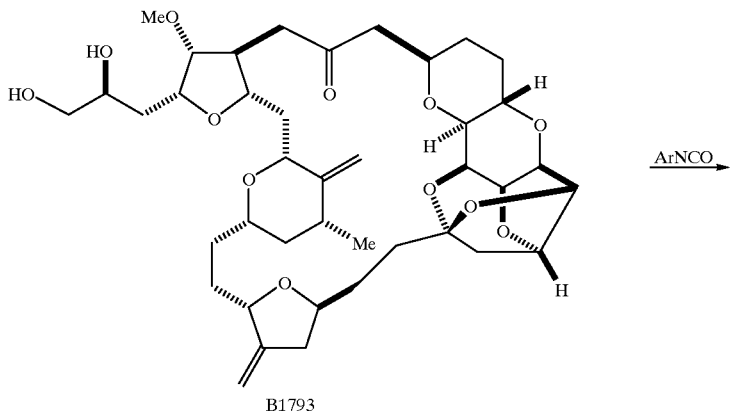

B1793

ArNCO →

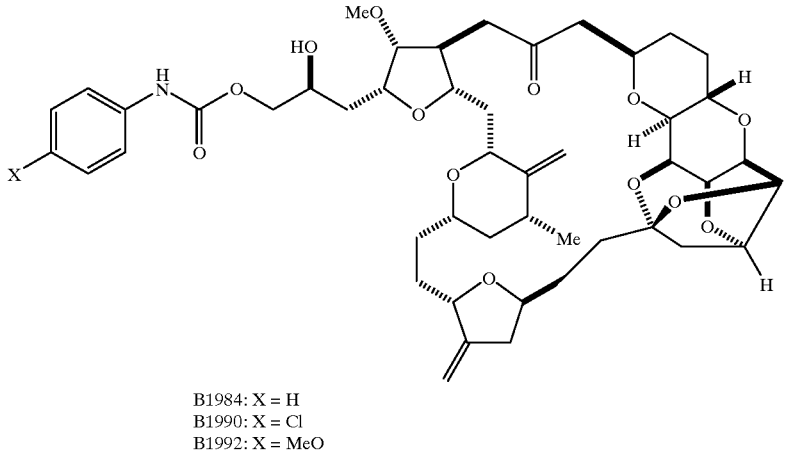

B1984: X = H
B1990: X = Cl
B1992: X = MeO

General A mixture of B1793 (1 mg, 1.37 micromol), Et₃N (10 microL, 72 micromol) and ArNCO (2 to 4 equiv.) in CH₂Cl₂ (0.2 mL) was stirred at rt for 4 h to overnight until the reaction was judged to be complete by TLC. The reaction mixture was diluted with saturated NaHCO₃ (3 mL), extracted with CH₂Cl₂ (3×) and EtOAc (2×), dried over Na₂SO₄ and purified by preparative TLC (5% MeOH—CH₂Cl₂) to afford the products:

B1984 (1.0 mg, 86%) HRMS (FAB): calcd for $C_{47}H_{63}NO_{13}$+Na 872.4197. Found: 872.4214.

B1990 (1.1 mg, 92%) HRMS (FAB): calcd for $C_{47}H_{62}ClNO_{13}$+Na 906.3807. Found: 906.3826.

B1992 (1.0 mg, 83%) HRMS (FAB): calcd for $C_{48}H_{65}NO_{14}$+Na 902.4303. Found: 902.4269.

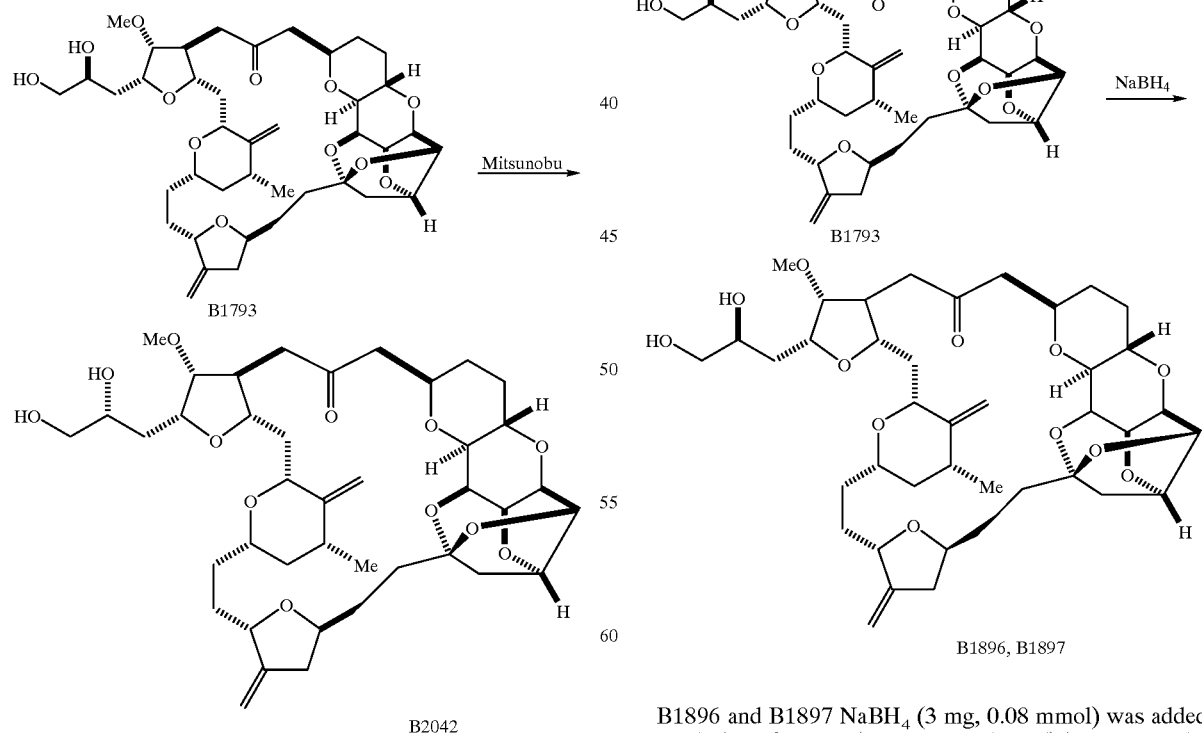

B2042 DEAD (0.4 M in ether, 50 μL, 19 μmol) was added to a solution of B1793 (2.0 mg, 2.7 μmol), triphenylphosphine (5 mg, 19 μmol), 4-nitrobenzoic acid (3. 2 mg, 19 μmol) and Et₂O (500 μL) at rt. After 22 h, the reaction mixture was loaded directly onto a preparative TLC plate and eluted with 60% EtOAc-hexanes to give the intermediate diester (3.0 mg). This material was taken up in MeOH (300 μL) and treated with K₂CO₃ (approximately 1 mg). After stirring at rt for 30 min, the reaction mixture was diluted with brine and extracted with CH₂Cl₂ (5×). The combined extracts were dried over Na₂SO₄, concentrated and purified by preparative TLC (5% MeOH-EtOAc) to afford B2042 (1.2 mg, 60% for two steps). HRMS (FAB): calcd for $C_{40}H_{58}O_{12}$+Na 753.3826. Found: 753.3810.

B1896 and B1897 NaBH₄ (3 mg, 0.08 mmol) was added to a solution of B1793 (2.30 mg, 3.15 μmol) in 1:1 CH₂Cl₂-MeOH (0.2 mL) at rt. Concentration of the reaction mixture and purification by preparative TLC (8% MeOH-EtOAc) provided B1896 (0.80 mg, 35%) and B1897 (2:1 mixture, 0.15 mg, 6.5%). HRMS (FAB) for B1896: calcd for $C_{40}H_{60}O_{12}$+Na 755.3983. Found: 753.3969.

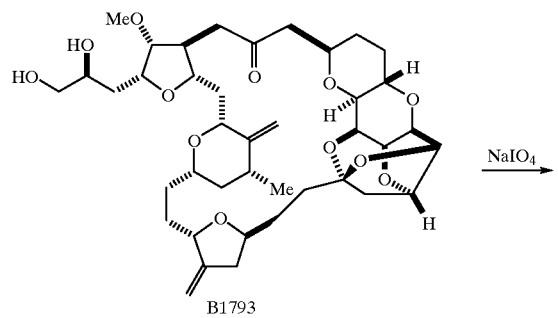

B1793

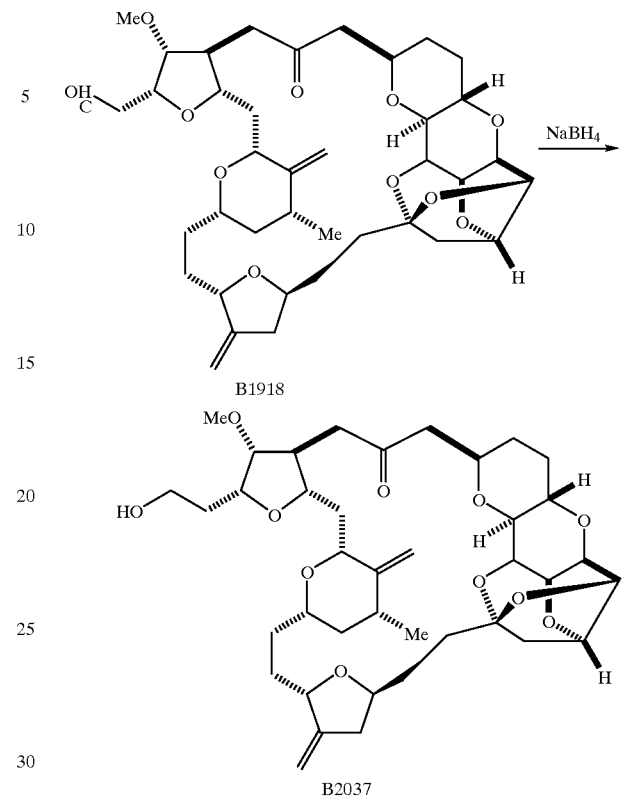

B1918

B2037

B1918 A mixture of B1793 (2.0 mg, 2.74 μmol), NaIO$_4$ (35 mg, 0.16 mmol), MeOH (0.8 mL) and H$_2$O (0.2 mL) was stirred at it for 40 min. The reaction mixture was diluted with H$_2$O (1 mL), extracted with CH$_2$Cl$_2$ (6×), dried over Na$_2$SO$_4$, concentrated and purified by column chromatography (5% MeOH—CH$_2$Cl$_2$) to give B1918 (1.9 mg, 100%).

B2037 A 0.034 M solution of NaBH$_4$ (0.1 mL, 3.4 μmol) in EtOH was added portionwise to a solution of B1918 (1.9 mg, 2.72 μmol) in MeOH (0.8 mL) and CH$_2$Cl$_2$ (0.2 mL) at −78° C. to rt until the reaction was judged to be complete by TLC. The reaction was quenched with saturated aqueous NH$_4$Cl (2 mL) at −78° C., warmed to rt, extracted with CH$_2$Cl$_2$ (6×), dried over Na$_2$SO$_4$ and purified by preparative TLC (5% MeOH—CH$_2$Cl$_2$) to afford B2037 (1.7 mg, 89%). HRMS (FAB): calcd for $C_{39}H_{56}O_{11}$+Na 723.3720. Found: 723.3749.

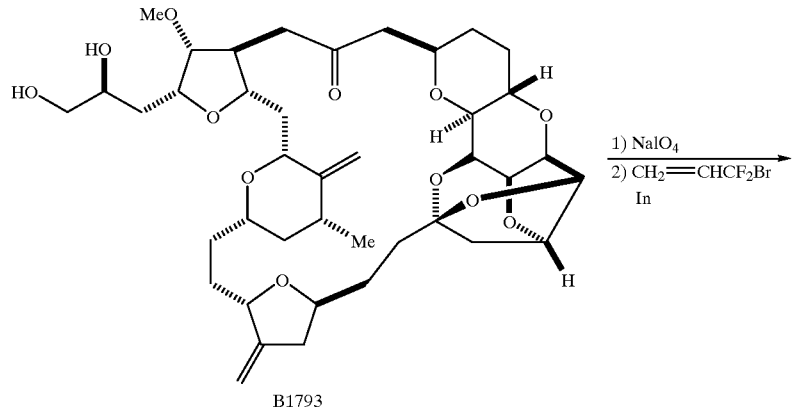

B1793

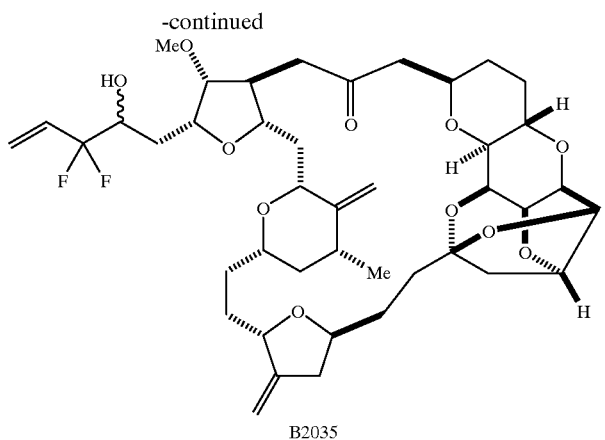

B2035

B2035 NaIO$_4$ (35 mg, 0.16 mmol) was added to a solution of B1793 (1.7 mg, 0.0023 mmol), MeOH (800 μL) and H$_2$O (200 μL) and after 15 min, the mixture was diluted with H$_2$O and extracted with CH$_2$Cl$_2$ (5×). The organic extracts were dried over Na$_2$SO$_4$, concentrated and the intermediate aldehyde was immediately dissolved in DMF (300 μL). 3-Bromo-3,3-difluoropropene (3 μL, 0.023 mmol) and indium powder (3 mg, 0.23 mmol) were added and after 24 h additional 3-bromo-3,3-difluoropropene (1 μL, 0.008 mmol) was added. After 18 h, H$_2$O was added the mixture was extracted with EtOAc (3×). The combined organic extracts were washed successively with H$_2$O and brine, dried over Na$_2$SO$_4$, concentrated and purified by preparative TLC (80% EtOAc-hexanes) to provide B2035 (0.74 mg, 41% for 2 steps) as a mixture of isomers. HRMS (FAB): calcd for C$_{42}$H$_{58}$F$_2$O$_{11}$+Na 799.3845. Found: 799.3883.

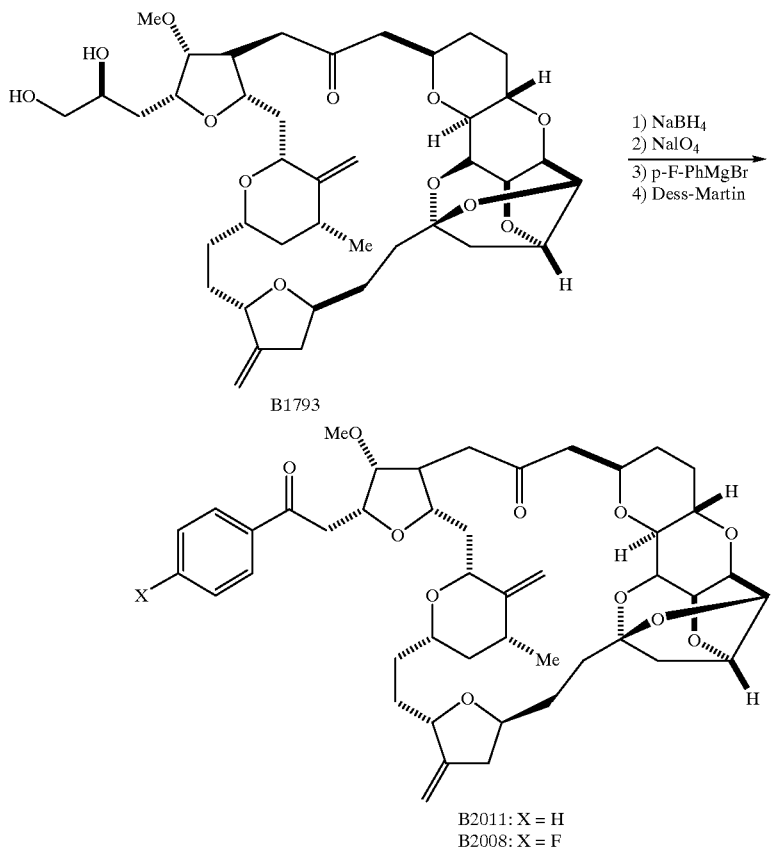

B1793

1) NaBH$_4$
2) NaIO$_4$
3) p-F-PhMgBr
4) Dess-Martin

B2011: X = H
B2008: X = F

B2008, B2011 NaBH$_4$ (2 mg, 0.05 mmol) was added to a solution of B1793 (2.2 mg, 0.003 mmol) in 1:1 CH$_2$Cl$_2$—MeOH (200 μL) at rt. After 15 min saturated aqueous NH$_4$Cl and H$_2$O were added, and the mixture was extracted with CH$_2$Cl$_2$ (6×) and EtOAc (2×). The combined organic extracts were dried over Na$_2$SO$_4$, concentrated and purified by column chromatography (10% MeOH-EtOAc) to provide an intermediate triol, which was dissolved in MeOH (800 μL) and H$_2$O (200 μL). NaIO$_4$ (35 mg, 0.16 mmol) was added and after 20 min, the mixture was diluted with H$_2$O and extracted with CH$_2$Cl$_2$ (6×). The organic extracts were dried over Na$_2$SO$_4$, concentrated and the intermediate aldehyde was immediately dissolved in THF (500 μL). 4-Fluorophenylmagnesium bromide (2M in Et$_2$O, 12 μL, 0.024 mmol) was added and after 20 min the reaction was quenched with saturated aqueous NH$_4$Cl. The mixture was extracted with CH$_2$Cl$_2$ (6×) and the combined organic extracts were dried over Na$_2$SO$_4$ and concentrated. Purification by preparative TLC (EtOAc) provided the desired product as a mixture of 4 isomers (1.32 mg, 55% for 3 steps).

Dess-Martin periodinane (~3 mg, 0.007 mmol) was added to a solution of the above product (0.95 mg, 0.0012 mmol) in CH$_2$Cl$_2$ (300 μL) and the mixture was stirred at rt for 20 min. Additional Dess-Martin periodinane (~3 mg, 0.007 mmol) and CH$_2$Cl$_2$ (300 μL) were added and after another 40 min Et$_2$O, saturated aqueous NaHCO$_3$ (4 mL) and saturated aqueous Na$_2$S$_2$O$_3$ (1 mL) were added. The mixture was extracted with Et$_2$O(3×) and the combined extracts were washed with brine, dried over Na$_2$SO$_4$, concentrated and purified by column chromatography (20% EtOAc-hexanes) to provide B2008 (0.58 mg, 61%). HRMS (FAB): calcd for C$_{45}$H$_{57}$FO$_{11}$+Na 815.3783. Found: 815.3758.

B2011 In an analogous manner, B1793 (1.9 mg, 0.003 mmol) was converted to B2011 (0.87 mg, 42% for 4 steps). HRMS (FAB): calcd for C$_{45}$H$_{58}$O$_{11}$+Na 797.3877. Found: 797.3877.

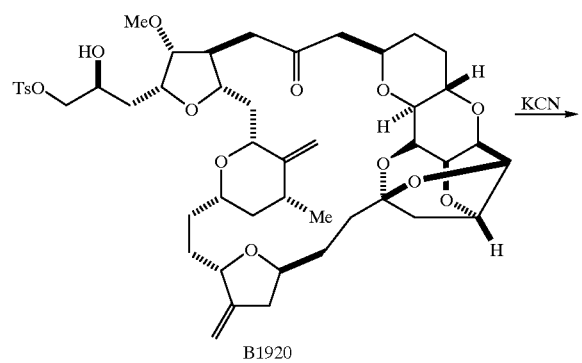

B2013 A solution of B1920 (1.4 mg, 0.0016 mmol), KCN (1 mg, 0.016 mmol) and DMSO (500 μL) was heated at 60° C. for 8 h. After cooling to rt, H$_2$O was added and the mixture was extracted with EtOAc (3×). The combined organic extracts were washed successively with H$_2$O and brine, dried over Na$_2$SO$_4$, concentrated and purified by preparative TLC (80% EtOAc-hexanes) to provide B2013 (0.78 mg, 67%). HRMS (FAB): calcd for C$_{41}$H$_{57}$NO$_{11}$+Na 762.3829. Found: 762.3848.

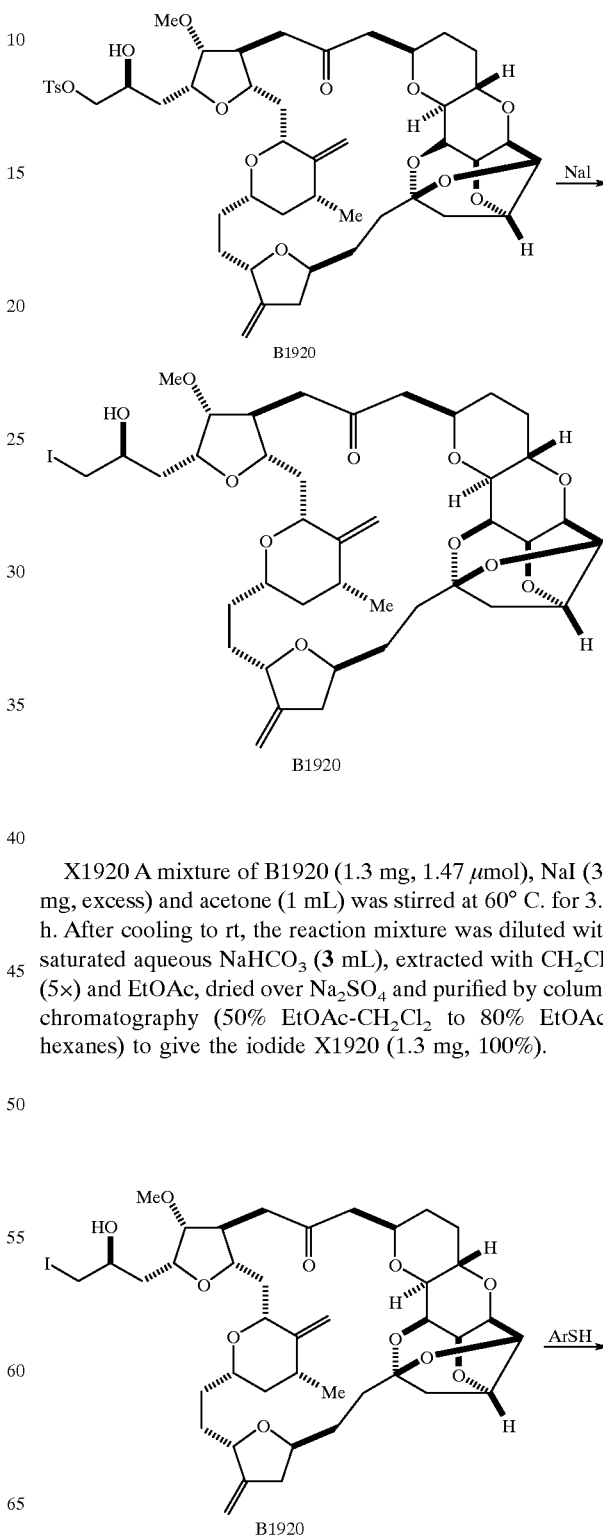

X1920 A mixture of B1920 (1.3 mg, 1.47 μmol), NaI (30 mg, excess) and acetone (1 mL) was stirred at 60° C. for 3.5 h. After cooling to rt, the reaction mixture was diluted with saturated aqueous NaHCO$_3$ (3 mL), extracted with CH$_2$Cl$_2$ (5×) and EtOAc, dried over Na$_2$SO$_4$ and purified by column chromatography (50% EtOAc-CH$_2$Cl$_2$ to 80% EtOAc-hexanes) to give the iodide X1920 (1.3 mg, 100%).

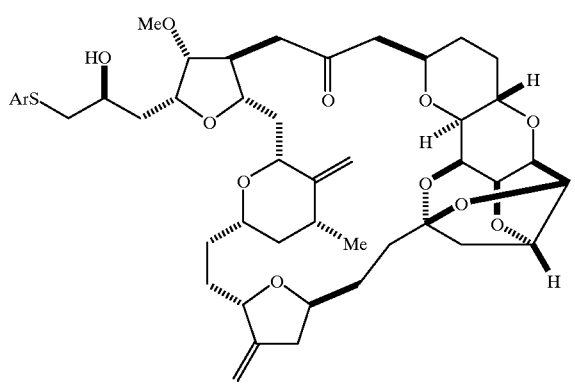

C1998: Ar = p-Cl—Ph
C2010: Ar = p-MeO—Ph
B2019: Ar = 2-imidazole

General A mixture of iodide X1920 (1.0 equiv.), iPr$_2$EtN (11 to 22 equiv.), ArSH (9 to 46 equiv.) and DMF (0.3 mL) was stirred at rt until the reaction was judged to be complete by TLC (typically 24 to 48 h). The reaction mixture was diluted with saturated aqueous NaHCO$_3$ (2 mL), extracted with CH$_2$Cl$_2$ and EtOAc, dried over Na$_2$SO$_4$ and purified by preparative TLC (80% EtOAc-hexanes or 5% MeOH-CH$_2$Cl$_2$) to afford the sulfide products:

B1998 (1.3 mg gave 1.1 mg, 85%) HRMS (FAB): calcd for C$_{46}$H$_{61}$ClO$_{11}$S+Na 897.3521. Found: 897.3533.

B2010 (1.1 mg gave 0.7 mg, 59%). HRMS (FAB): calcd for C$_{47}$H$_{64}$O$_2$S+Na 875.4016. Found: 875.4057.

B2019 (1.1 mg gave 0.7 mg, 61%) MS (FAB): M+Na

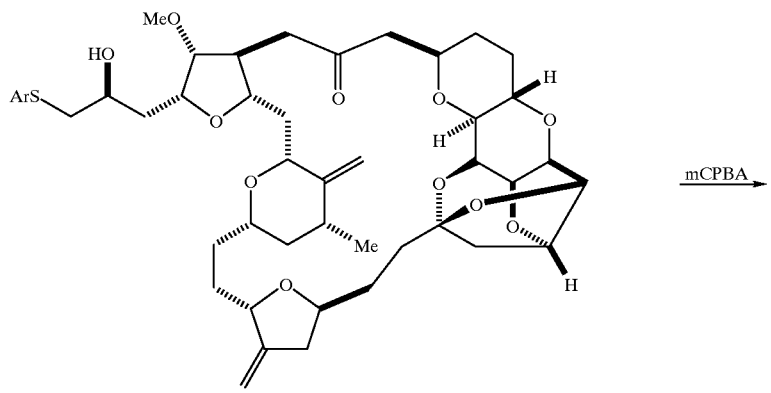

B1998: Ar = p-Cl—Ph
B2010: Ar = p-MeO—Ph

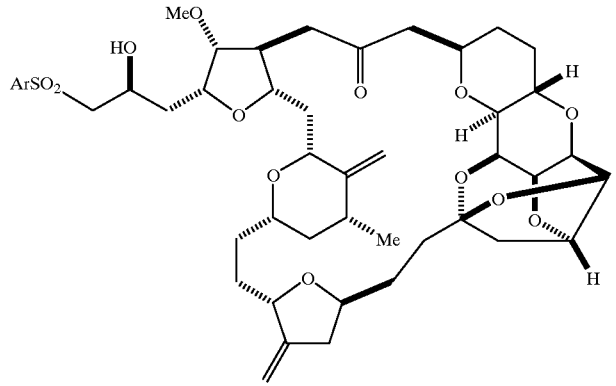

B2016: Ar = p-Cl—Ph
B2030: Ar = p-MeO—Ph

General A 0.01 M solution of mCPBA (1.2 equiv.) in CH$_2$Cl$_2$ was added to a solution of a sulfide (1.0 equiv.) in CH$_2$Cl$_2$ (0.5 mL) at 0° C. for 30 min. The reaction mixture was diluted with saturated NaHCO$_3$ (2 mL), extracted with CH$_2$Cl$_2$ and EtOAc, dried over Na$_2$SO$_4$ and purified by preparative TLC (80% EtOAc-hexanes or EtOAc) to afford the products:

B2016 (0.9 mg gave 0.7 mg, 74%)

B2030 (1.0 mg gave 0.6 mg, 61%) HRMS (FAB): calcd for C$_{47}$H$_{64}$O$_{14}$S+Na 907.3914. Found: 907.3950.

This material was dissolved in CH$_2$Cl$_2$ (0.5 mL) and treated with Dess-Martin periodinane (10 mg, 24 μmol) for 1.5 h at rt, diluted with Et$_2$O and filtered through Celite. The filtrate was concentrated and purified by preparative TLC (50% EtOAc-hexanes) to afford the diketone intermediate (1.0 mg, 77%), which was dissolved in THF (0.5 mL) and treated with 0.02 M TBAF containing 0.01 M imidazole hydrochloride (THF solution, 75 μL, 1.5 μmol) at rt for 15

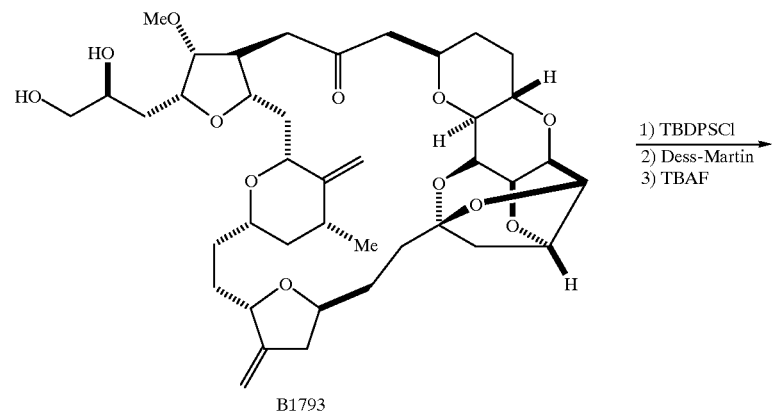

B1793

1) TBDPSCl
2) Dess-Martin
3) TBAF

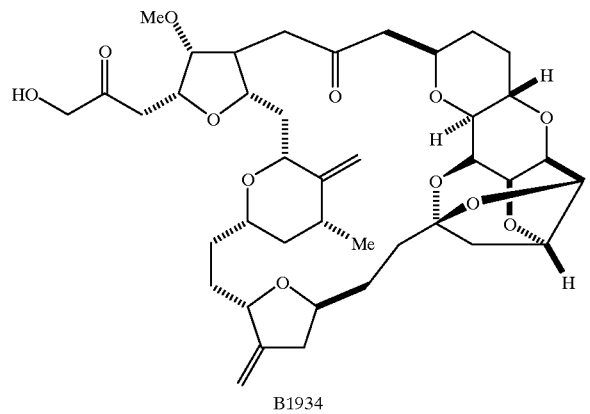

B1934

B1934 TBDPSCI (3.0 μL, 12 μmol) was added to a solution of B1793 (1.3 mg, 1.78 μmol), imidazole (10 mg, 166 μmol) and DMF (0.10 mL) at rt. After stirring for 1 h, the reaction mixture was diluted with saturated aqueous NaHCO$_3$ (2 mL), extracted with CH$_2$Cl$_2$ (3×) and EtOAc (2×), dried over Na$_2$SO$_4$ and purified by preparative TLC (5% MeOH—CH$_2$Cl$_2$) to give the intermediate silyl ether (1.3 mg, 77%).

min. The reaction mixture was eluted through a SiO$_2$ column (50% EtOAc-hexanes to 5% MeOH—CH$_2$Cl$_2$) and the desired product was further purified by preparative TLC (5% MeOH—CH$_2$Cl$_2$) to afford B1934 (0.75 mg, 100%). HRMS (FAB): calcd for C$_{40}$H$_{56}$O$_{12}$+Na 751.3669. Found: 751.3690.

Synthesis of B1939:

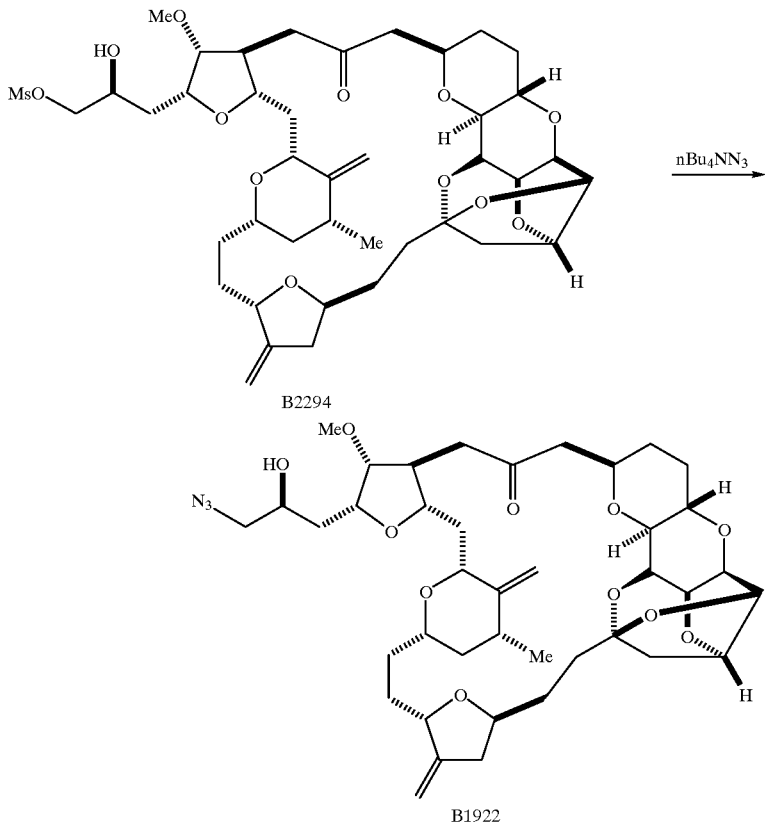

B1922 Tetra-n-butylammonium azide (0.2 M in DMF, 0.5 mL, 0.10 mmol) was added to a solution of mesylate B2294 (21.4 mg, 0.026 mmol) in DMF (2 mL) at rt. After stirring at 83° C. for 3.5 h, the reaction mixture was cooled to rt, diluted with toluene, concentrated and purified by preparative TLC (80% ethyl acetate-hexanes) to furnish B1922 (18 mg, 92%).

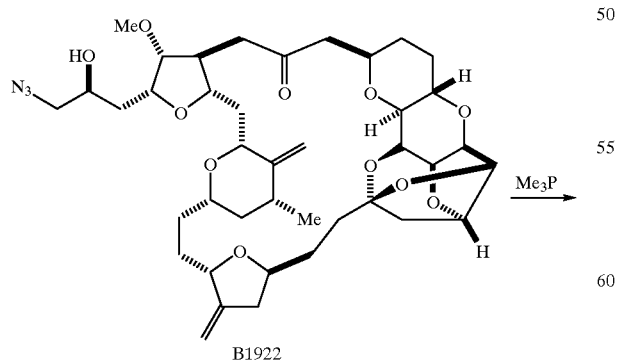

-continued

B1939 Me$_3$P (1 M in THF) and H$_2$O (0.8 mL) were sequentially added to a solution of azide B1922 (24.6 mg, 0.032 mmol) in THF (3.2 mL) at rt. The mixture was stirred for 22 h, diluted with toluene, concentrated and purified by flash chromatography [step gradient, 10% MeOH-EtOAc followed by MeOH-EtOAc-30% aqueous NH$_4$OH (9:86:5)] to provide the desired primary amine (23.3 mg), which by $^1$H-NMR contained ~1% trimethylphosphine oxide. Lyophilization from benzene and standing under high vacuum for 2 d furnished B1939 (20.3 mg, 87%).

Synthesis of Representative B1939 Analogs:
B1930, B1940, B1973, B1987, B1988, B1991, B2003, B2004

EDC (0.06 M in $CH_2Cl_2$, 100 μL, 11 μmol) was added to a solution of the crude amine, benzoylformic acid (0.8 mg, 5.3 μmol) and $CH_2Cl_2$ (200 μL) at rt. After 30 min, the reaction was quenched with a 1:4 mixture of saturated aqueous $NaHCO_3$-brine and extracted with $CH_2Cl_2$ (5×).

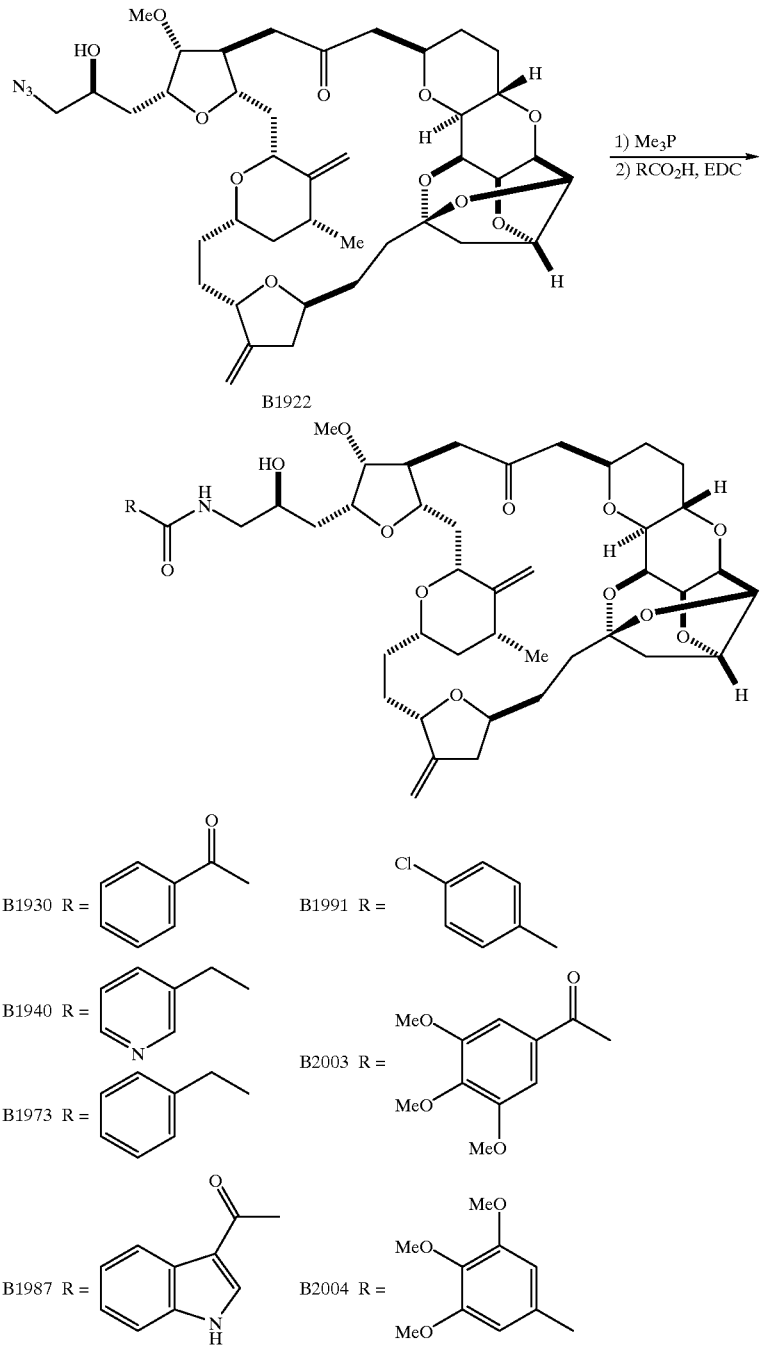

B1930 $Me_3P$ (1 M in THF, 13 μL, 0.013 mmol) was added to a solution of B1922 (1.6 mg, 2.1 μmol), THF (400 μL) and $H_2O$ (100 μL) at rt. The mixture was stirred for 22 h, diluted with toluene, concentrated, and azeotropically dried with toluene (2×) to give the crude amine which was used directly in the next step.

The combined extracts were dried over $Na_2SO_4$ and concentrated and purified by preparative TLC (EtOAc) to afford B1930 (1.5 mg, 83% for two steps). HRMS (FAB): calcd for $C_{48}H_{63}NO_{13}$+Na 884.4197. Found: 884.4166.

B1940 Using the procedure described above for B1930, B1922 was reduced, coupled with 3-pyridylacetic acid hydrochloride and purified by preparative TLC [(MeOH- EtOAc-30% aqueous NH$_4$OH (9:86:5)] to afford B1940 (0.8 mg, 67% for two steps). HRMS (FAB): calcd for C$_{47}$H$_{64}$N$_2$O$_{12}$+Na 871.4357. Found: 871.4362.

B1973 Using the procedure described above, B1922 (0.9 mg, 1.2 μmol) was reduced, coupled with phenylacetic acid and purified by preparative TLC (5% MeOH-EtOAc) to afford B1973 (0.44 mg, 44 % for two steps). HRMS (FAB): calcd for C$_{48}$H$_{65}$NO$_{12}$+Na 870.4404. Found: 870.4447.

B1987 Using the procedure described above, B1922 (0.9 mg, 1.2 μmol) was reduced, coupled with 3-indoleglyoxylic acid and purified by preparative TLC (3% MeOH-EtOAc) to afford B1987 (0.8 mg, 75% for two steps). HRMS (FAB): calcd for C$_{50}$H$_{64}$N$_2$O$_{12}$+Na 923.4306. Found: 923.4338.

B1991 Using the procedure described above, B1922 (1.0 mg, 1.3 μmol) was reduced, coupled with 4-chlorobenzoic acid and purified by preparative TLC (3% MeOH-EtOAc) to afford B1991 (0.8 mg, 70% for two steps). HRMS (FAB): calcd for C$_{47}$H$_{62}$ClNO$_{12}$+Na 890.3858. Found: 890.3843.

B2003 Using the procedure described above, B1922 (1.0 mg, 1.3 μmol) was reduced, coupled with 3,4,5-trimethoxybenzoylformic acid and purified by preparative TLC (EtOAc) to afford B2003 (0.7 mg, 56% for two steps). HRMS (FAB): calcd for C$_{51}$H$_{69}$NO$_{16}$+Na 974.4514. Found: 974.4525.

B2004 Using the procedure described above, B1922 (1.0 mg, 1.3 μmol) was reduced, coupled with 3,4,5-trimethoxybenzoic acid and purified by preparative TLC (5% MeOH-EtOAc) to afford B2004 (0.7 mg, 58% for two steps). HRMS (FAB): calcd for C$_{49}$H$_{65}$NO$_{13}$+Na 946.4565. Found: 946.4599.

B1988 Dess-Martin periodinane (1 mg, 2.3 μmol) was added to a solution of B1930 (0.80 mg, 0.93 μmol) in CH$_2$Cl$_2$ (500 μL) at rt. After 1 h, the reaction was diluted with Et$_2$O and filtered through Celite. The filtrate was washed sequentially with a 1:9 mixture of saturated aqueous NaHCO$_3$—Na$_2$S$_2$O$_3$ and brine, dried over Na$_2$SO$_4$, concentrated and purified by preparative TLC (80% EtOAc-hexanes) to afford B1988 (0.45 mg, 56%). HRMS (FAB): calcd for C$_{48}$H$_{61}$NO$_{13}$+Na 882.4041. Found: 884.4012.

Synthesis of B2090:

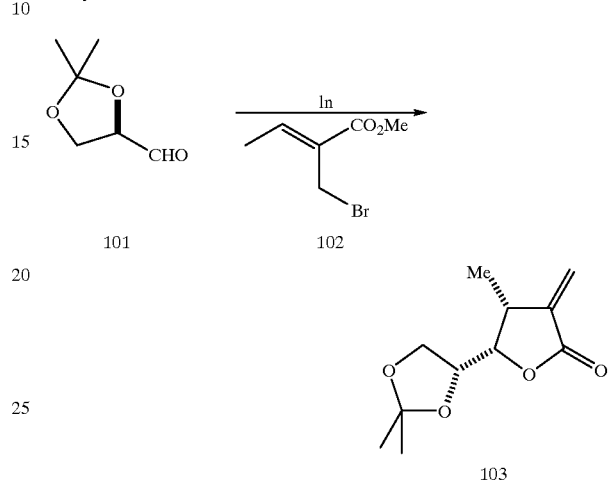

Compound 103 Indium powder (1.35 g, 11.8 mmol) was added to a solution of 102 (3.38 g, 17.6 mmol) in DMF (20

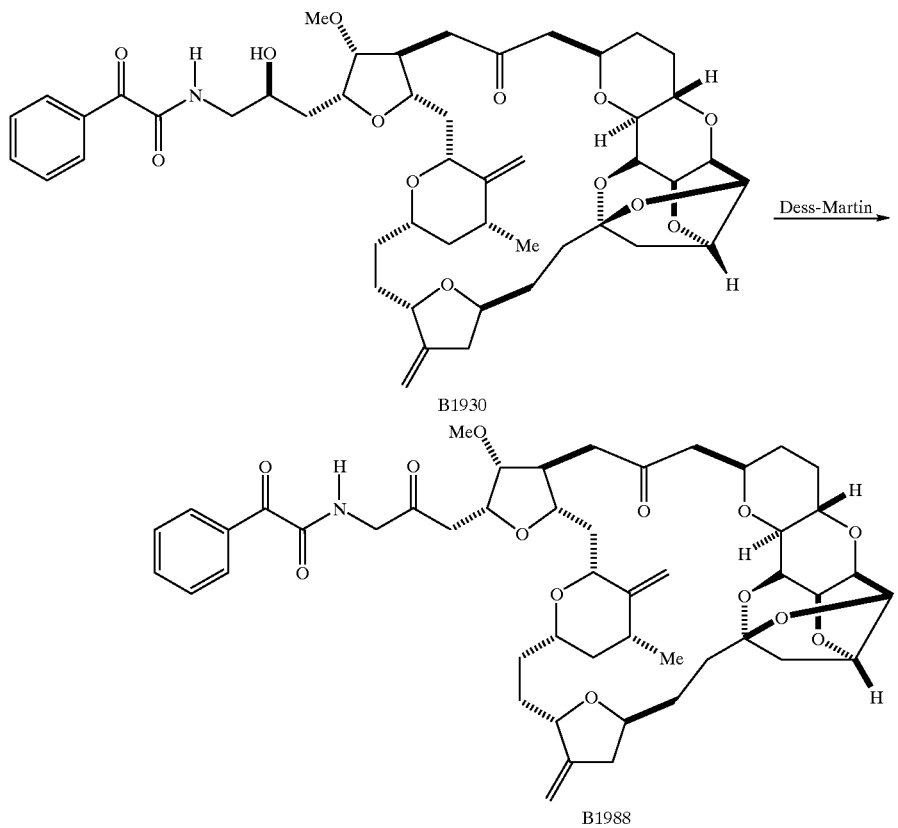

mL) at rt. After stirring for 30 min, the reaction mixture was cooled to 0° C. Neat aldehyde 101 (3.72 g, 28.6 mmol) was then added and the mixture was stirred overnight while allowing the temperature to warm to rt. The reaction mixture was recooled to 0° C. and then quenched carefully with saturated aqueous NH₄Cl (100 mL). After stirring for 30 min, the resulting mixture was extracted with Et₂O (3x), dried over Na₂SO₄, concentrated and purified by column chromatography (10% to 20% EtOAc-hexanes) to give pure crystalline 103 (2.20 g, 59%).

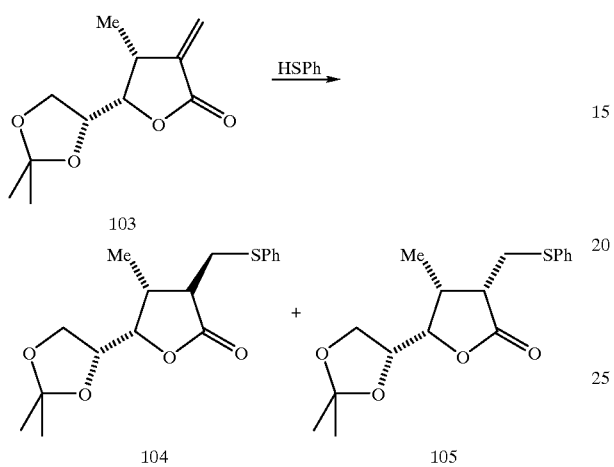

Compound 104 Et₃N (72 µL, 0.51 µmol) was added to a solution of 103 (1.09 g, 5.13 mmol) and thiophenol (0.63 mL, 7.16 mmol) in CH₂Cl₂ and the resulting mixture was stirred at 0° C. for 1 h. Filtration through SiO₂ gave a mixture of 104 and 105, which after MPLC (15% to 20% EtOAc-hexanes) afforded 104 (0.53 g, 32%) and 105 (0.92 g, 56%).

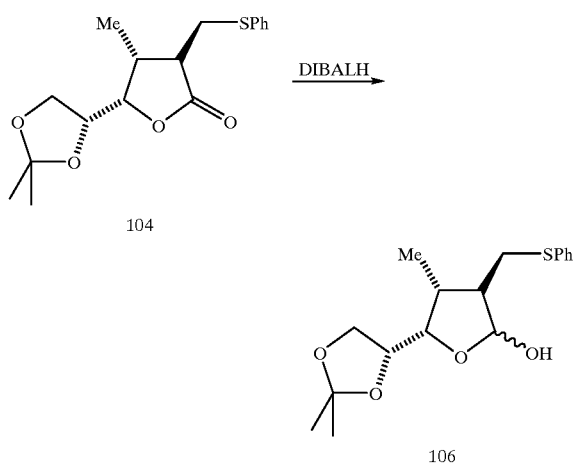

Compound 106 DIBALH (1 M in toluene, 3.28 mL, 3.28 mmol) was added to a solution of 104 (0.53 g, 1.64 mmol) in toluene (10 mL) at −78° C. and the mixture was stirred at −78° C. for 10 min. The reaction was quenched by careful addition of MeOH (0.40 mL, 9.84 mmol) and H₂O (0.17 mL, 9.84 mmol), warmed to rt and stirred for 20 min. The white suspension was filtered through a mixture of Celite and SiO₂ with 1:1 CH₂Cl₂-Et₂O and concentrated to give 106 (0.53 g, 100%) as an oil.

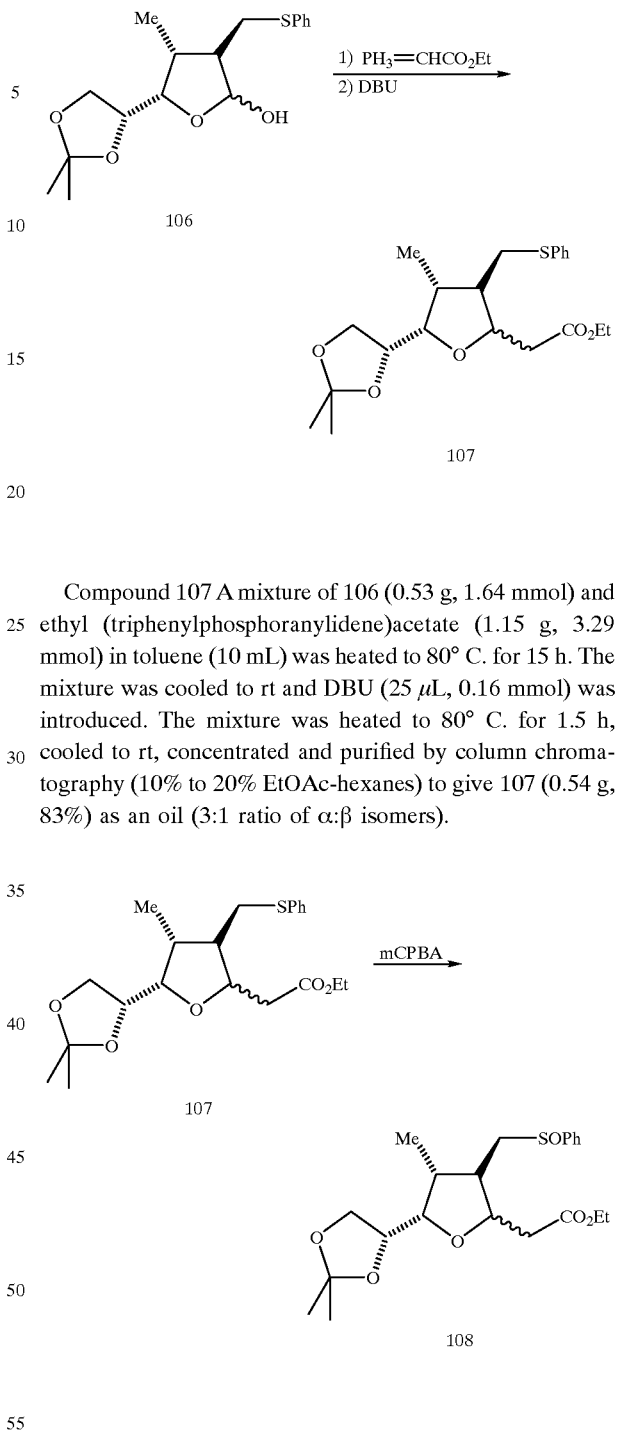

Compound 107 A mixture of 106 (0.53 g, 1.64 mmol) and ethyl (triphenylphosphoranylidene)acetate (1.15 g, 3.29 mmol) in toluene (10 mL) was heated to 80° C. for 15 h. The mixture was cooled to rt and DBU (25 µL, 0.16 mmol) was introduced. The mixture was heated to 80° C. for 1.5 h, cooled to rt, concentrated and purified by column chromatography (10% to 20% EtOAc-hexanes) to give 107 (0.54 g, 83%) as an oil (3:1 ratio of α:β isomers).

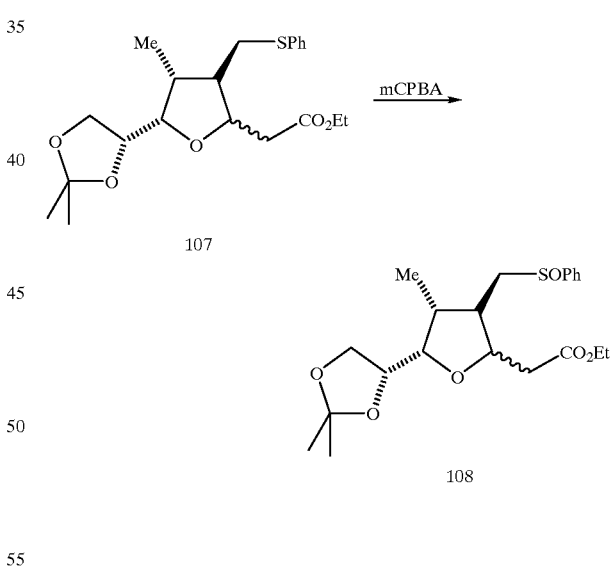

Compound 108 A solution of mCPBA (~51%, 450 mg in 4.5 mL CH₂Cl₂, 1.44 mmol) was added to a solution of 107 (0.54 g, 1.36 mmol) in CH₂Cl₂ (10 mL) at −78° C. The reaction mixture was diluted with saturated aqueous NaHCO₃ (50 mL), H₂O (10 mL), and Et₂O (60 mL) and then warmed to rt. The separated aqueous layer was extracted with EtOAc (4x) and the combined organic phases were dried over Na₂SO₄, concentrated and purified by column chromatography (50% EtOAc-hexanes) to give 108 (0.51 g, 92%) as an oil.

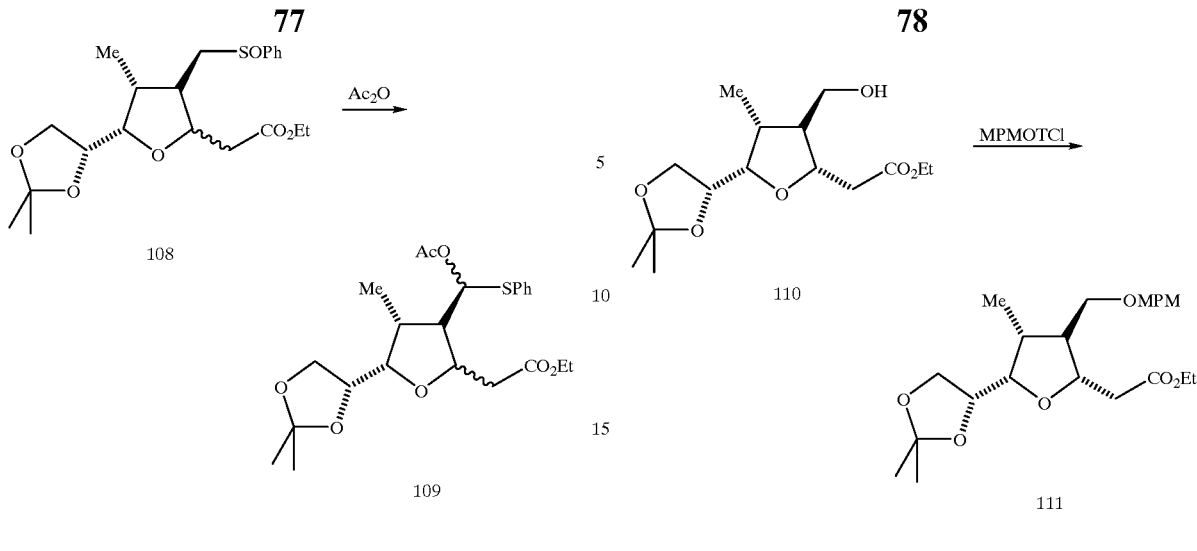

Compound 109 A mixture of 108 (0.51 g, 1.24 mmol) and NaOAc (1.00 g, 12.4 mmol) in Ac₂O (10 mL) was stirred at 140° C. for 12 h, cooled to rt and then concentrated. The residue was partitioned between saturated aqueous NaHCO₃ (20 mL) and Et₂O (30 mL), and stirred vigorously at rt for 30 min. The separated aqueous layer was extracted with Et₂O (2×), and the combined organic phases were dried over Na₂SO₄, concentrated and purified by column chromatography (5% to 15% EtOAc-hexanes) to give 109 (0.41 g, 73%) as an oil.

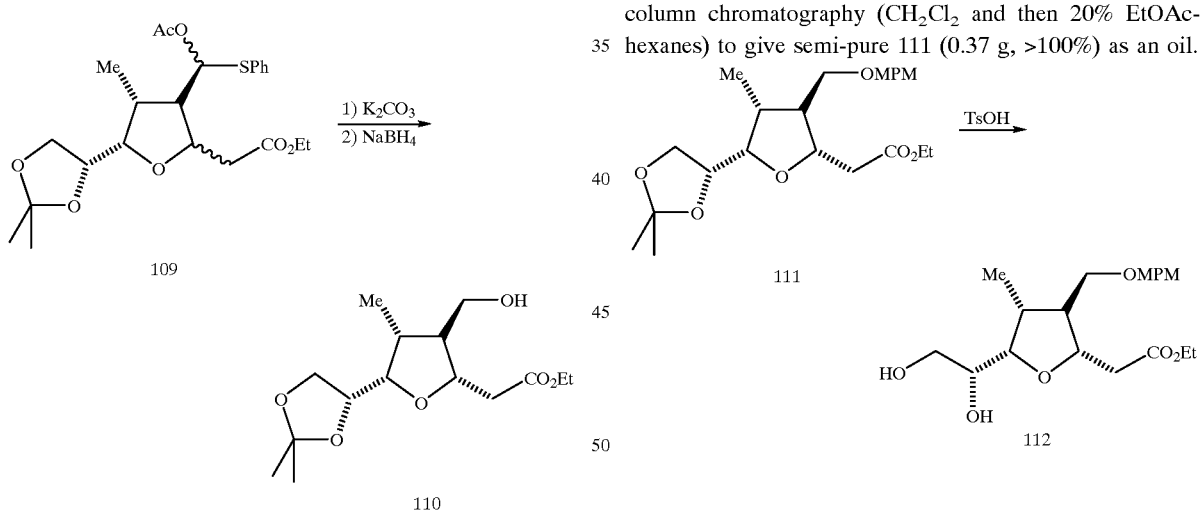

Compound 110 A mixture of 109 (0.41 g, 0.91 mmol) and K₂CO₃ (44.3 mg, 0.32 mmol) in EtOH (5 mL) was heated to 60–70° C. for 1 d. After cooling to rt, the reaction mixture was concentrated and eluted through a SiO₂ column (10% to 20% EtOAc-hexanes) to give the partially purified aldehyde intermediate. This material was dissolved in EtOH (2.5 mL), treated with NaBH₄ (50 mg, 1.32 mmol) and stirred at rt for 30 min. The mixture was concentrated and purified by column chromatography (40% EtOAc-hexanes) to give 110 (181 mg, 66%).

Compound 111 BF₃.OEt₂ (0.05 M in CH₂Cl₂, 175 µL, 8.75 µmol) was added to a solution of 110 (181 mg, 0.60 mmol) and p-methoxybenzyl 2,2,2-trichloroacetimidate (0.50 mL, 1.80 mmol) in CH₂Cl₂ (5 mL) at 0° C. The resulting mixture was stirred for 1.5 h at 0° C. and for 2 h at rt until the reaction was complete. The mixture was quenched with saturated aqueous NaHCO₃ (25 mL) and extracted with Et₂O (5×). The combined organic phases were dried over Na₂SO₄, concentrated and purified by column chromatography (CH₂Cl₂ and then 20% EtOAc-hexanes) to give semi-pure 111 (0.37 g, >100%) as an oil.

Compound 112 A mixture of 111 (0.37 g, max.=0.60 mmol) and TsOH.H₂O (36 mg) in EtOH (5 mL) was stirred initially at rt overnight and then at 60° C. for 1 h. Additional TsOH.H₂O (31 mg) was added at rt and the reaction mixture was stirred for 1 h at rt. The mixture was then concentrated, quenched with saturated aqueous NaHCO₃ and extracted with EtOAc (5×). The combined organic phases were dried over Na₂SO₄, concentrated and purified by column chromatography (20% to 50% EtOAc-hexanes and then 5% MeOH—CH₂Cl₂) to give 112 (121 mg, 53%) as an oil along with recovered 111 (49 mg, 21%).

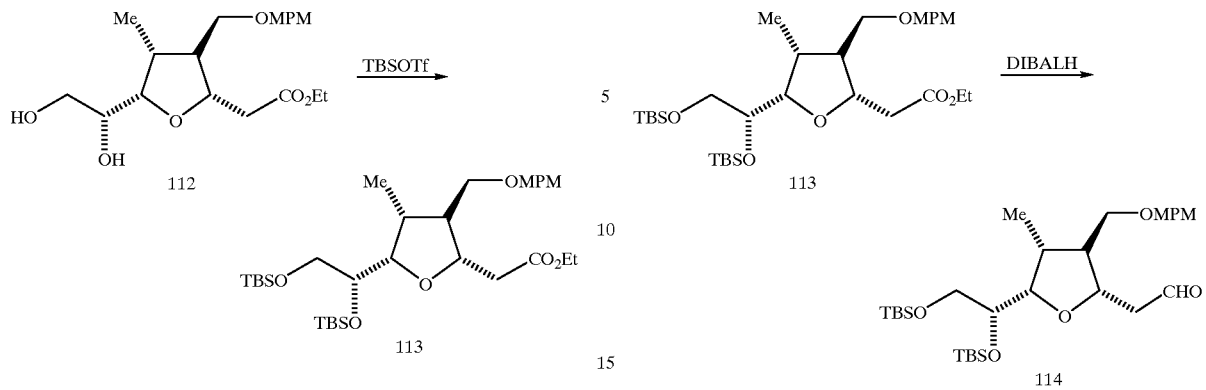

Compound 113 TBSOTf (250 μL, 1.09 mmol) was added to a solution of 112 (121 mg, 0.32 mmol) and Et₃N (176 μL, 1.26 mmol) in CH₂Cl₂ at 0° C. and the resulting mixture was stirred for 25 min. The reaction was quenched with saturated aqueous NaHCO₃ (15 mL) and the separated aqueous layer was extracted with ether (3×). The combined organic phases were dried over Na₂SO₄, concentrated and purified by column chromatography (5% to 10% EtOAc/hexanes) to give 113 (165 mg, 85%) as an oil.

Compound 114 DIBALH (1 M in toluene, 0.54 mL, 0.54 immol) was added to a solution of 113 (165 mg, 0.27 mmol) in toluene (5 mL) at −78° C. and the resulting mixture was stirred at −78° C. for 10 min. The reaction was quenched by careful addition of MeOH (65 μL, 0.81 mmol) and H₂O (29 μL, 0.81 mmol), warmed to rt and stirred for 25 min. The white suspension was filtered through Celite with 1:1 CH₂Cl₂-Et₂O. Concentration and purification by column chromatography (10% to 20% EtOAc-hexanes) gave 114 (153 mg, 100%) as an oil.

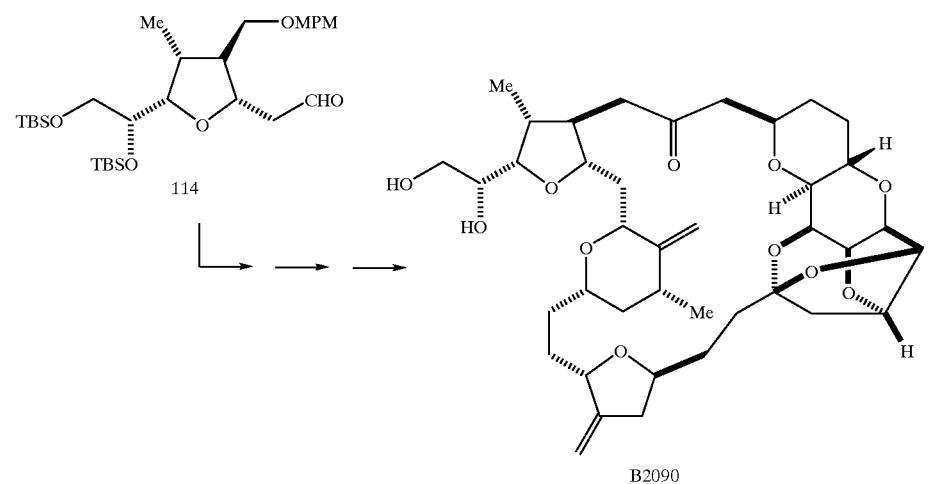

B2090 In a manner similar to that described in Scheme 6 for the synthesis of B1794, intermediate 114 was converted to B2090. HRMS (FAB): calcd for $C_{39}H_{56}O_{11}$+Na 723.3720. Found: 723.3731.

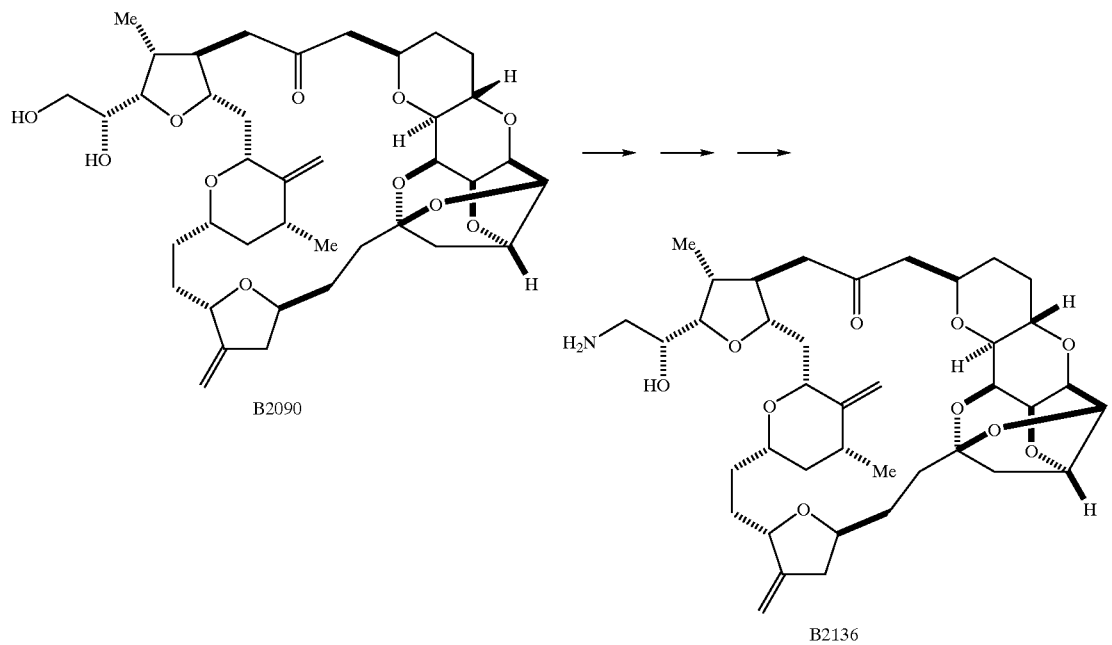

B2136 In a manner analogous to that of B1939, B2090 was converted to B2136. HRMS (FAB): calcd for $C_{39}H_{57}NO_{10}$+Na 722.3880. Found: 722.3907.

Synthesis of B2039/B2043:

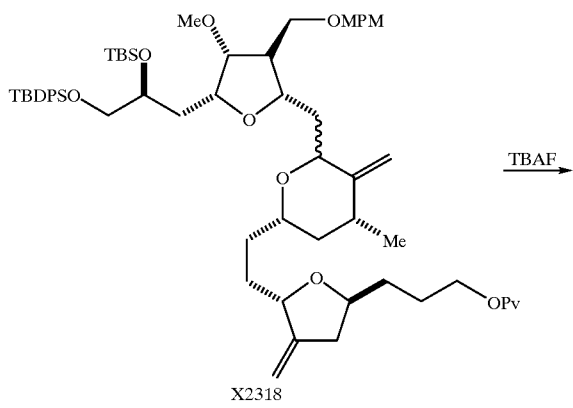

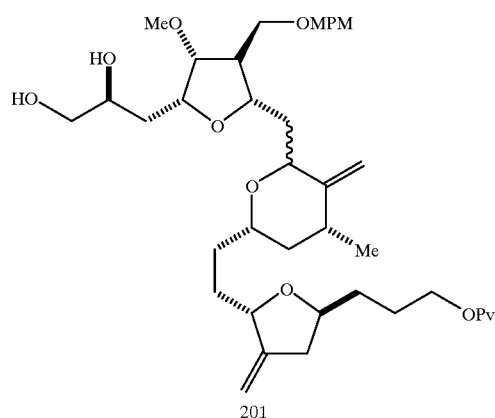

Diol 201 TBAF (1 M in THF, 383 μL, 0.383 mmol) was added to a solution of X2318 (350-LS-218 )(80.8 mg, 0.0765 mmol) in THF (7 mL) and stirred at rt for 16 h. After partial concentration, the residue was loaded directly onto a $SiO_2$ column packed using 30% EtOAc-hexanes. Gradient elution (30% EtOAc-hexanes to EtOAc) furnished diol 201 (49.7 mg, 92%).

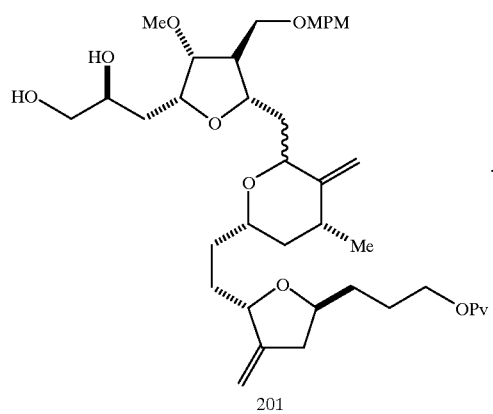

201

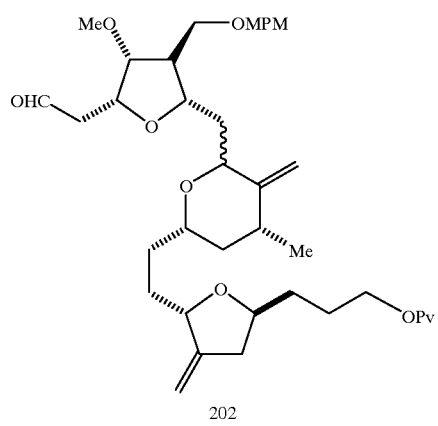

202

Aldehyde 202 A mixture of diol 201 (49.7 mg, 0.0707 mmol), NaIO₄ (100 mg, 0.47 mmol), MeOH (10 mL) and H₂O (2.5 mL) was stirred at rt for 30 min. H₂O was added and the mixture was extracted with CH₂Cl₂ (4×). The combined organic extracts were dried over Na₂SO₄, concentrated and purified by column chromatography (30% EtOAc-hexanes) to provide aldehyde 202 (41.7 mg, 88%).

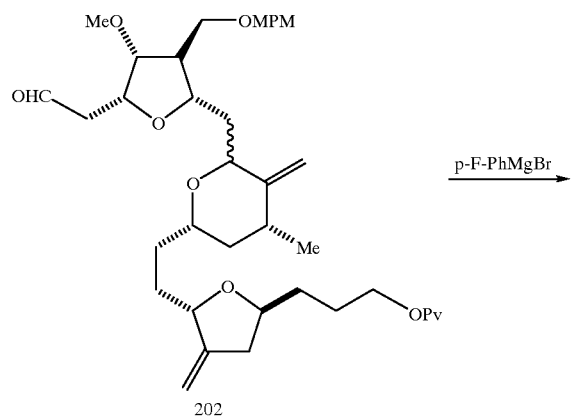

202

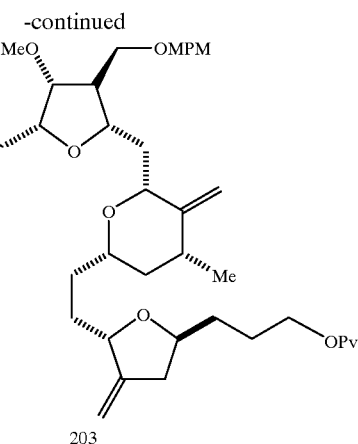

203

Alcohol 203 4-Fluorophenylmagnesium bromide (2 M in Et₂O, 155 μL, 0.31 mmol) was added to a solution of aldehyde 202 (41.7 mg, 0.062 mmol) in THF (6 mL). After 15 min at rt, the reaction was quenched with saturated aqueous NH₄Cl and extracted with CH₂Cl₂ (4×). The combined organic extracts were dried over Na₂SO₄, concentrated and purified by preparative TLC (40% EtOAc-hexanes) to provide alcohol 203 (32.4 mg, 68%) as a 1:1 mixture of C34 isomers. The minor undesired C27 isomer was separated at this stage and was also isolated as a 1:1 mixture of C34 isomers (8.4 mg, 18%).

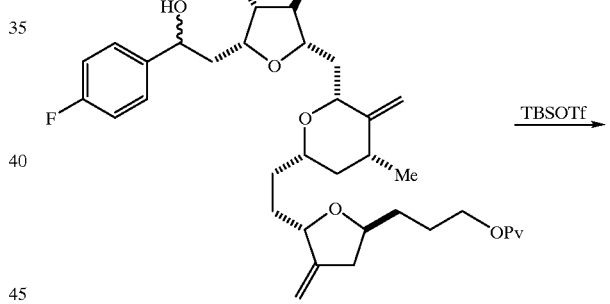

203

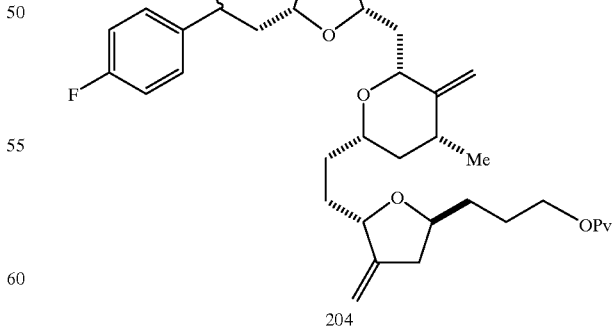

204

Ether 204 Et₃N (18 μL, 0.13 mmol) and TBSOTf (15 μL, 0.063 mmol) were added to a solution of alcohol 203 (32.4 mg, 0.042 mmol) in CH$_2$Cl$_2$ (5 mL) at 0° C. After 20 min the reaction was quenched by the addition of saturated aqueous NH$_4$Cl and extracted with CH$_2$Cl$_2$ (3×). The combined organic extracts were dried over Na$_2$S$_4$, concentrated and purified by column chromatography (20% EtOAc-hexanes) to provide ether 204 (33.1 mg, 89%).

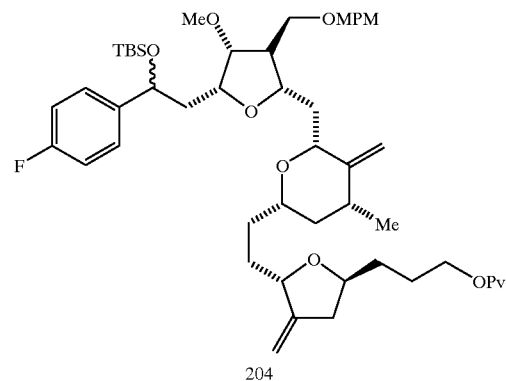

204

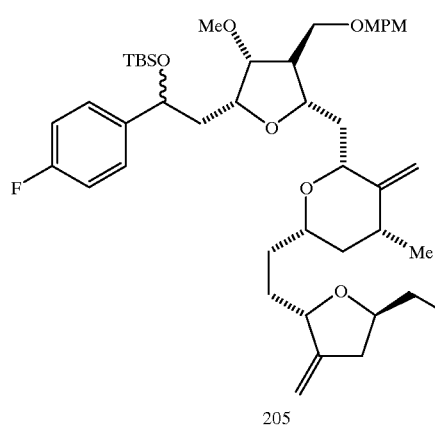

205

Alcohol 205 LAH (1 M in THF, 113 μL, 0.113 mmol) was added dropwise to a solution of ether 204 (33.1 mg, 0.0375 mmol) in Et$_2$O (10 mL) at 0° C. After 20 min, H$_2$O and I M NaOH were added and the mixture was stirred at rt for 10 min. Filtration through Celite, concentration and purification by column chromatography (40% EtOAc-bexanes) furnished alcohol 205 (28.4 mg, 95%).

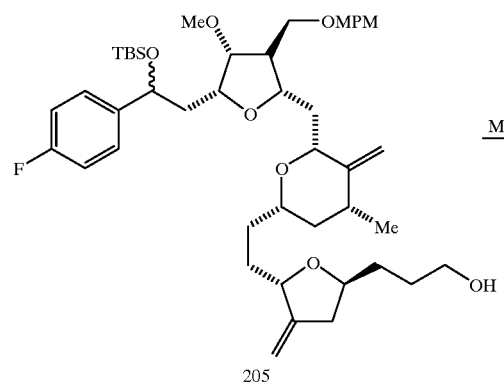

205

Ether 206 Diisopropylethylamine (31 μL, 0.18 mmol) and MMTrCl (22 mg, 0.071 mmol) were added to a solution of alcohol 205 (28.4 mg, 0.0356 mmol) in CH$_2$Cl$_2$ (4 mL) at 0° C. After 15 h at rt, H$_2$O was added and the mixture was extracted with CH$_2$Cl$_2$ (3×). The combined extracts were washed with brine, dried over Na$_2$SO$_4$, concentrated and purified by preparative TLC (40% EtOAc-hexanes) to provide ether 206 as a ~1.5:1 mixture of C34 epimers (45 mg, quant), which contained a small amount of close-running impurities.

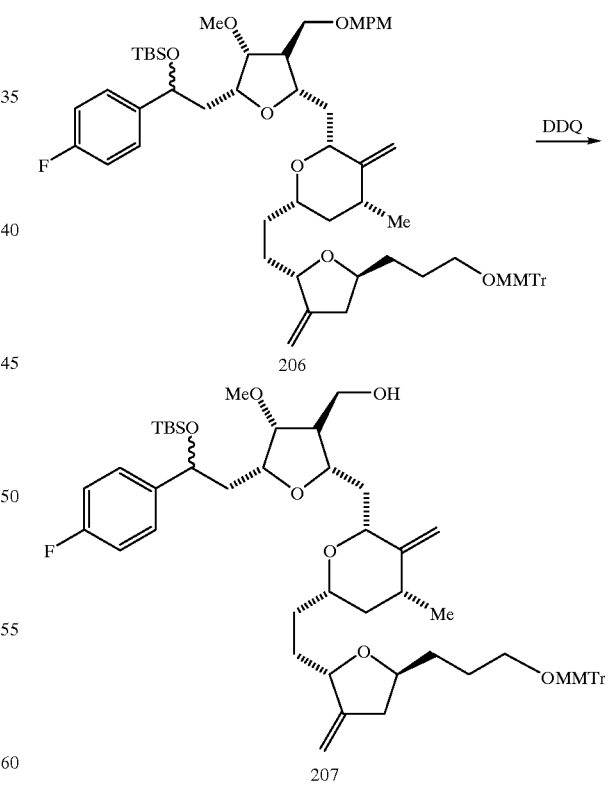

Alcohol 207 DDQ (40 mg, 0.18 mmol) was added to a solution of ether 206 (37 mg, 0.034 mmol) in CH$_2$Cl$_2$ (4 mL) and a 1:10 mixture of tBuOH:pH 7 phosphate buffer (2 mL)

at 0° C. The mixture was stirred vigorously in the dark for 15 min. Three additional portions of DDQ (40 mg, 0.18 mmol) were added at 10 min intervals, then the reaction was diluted with saturated aqueous NaHCO$_3$ and extracted with CH$_2$Cl$_2$ (3×). The combined organic extracts were washed with brine, dried over Na$_2$SO$_4$, concentrated and purified by preparative TLC (30% EtOAc-hexanes) to provide alcohol 207 (19.2 mg, 59%) as well as recovered ether 206 (9.7 mg, 26%).

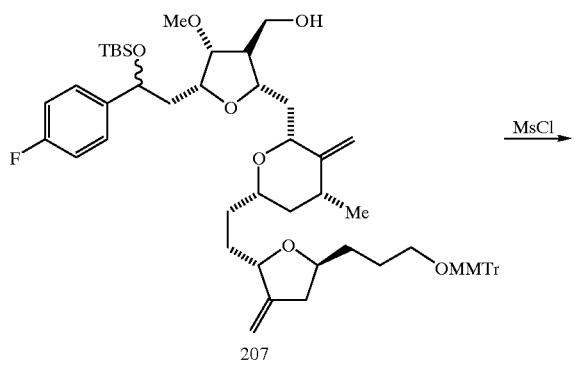

207

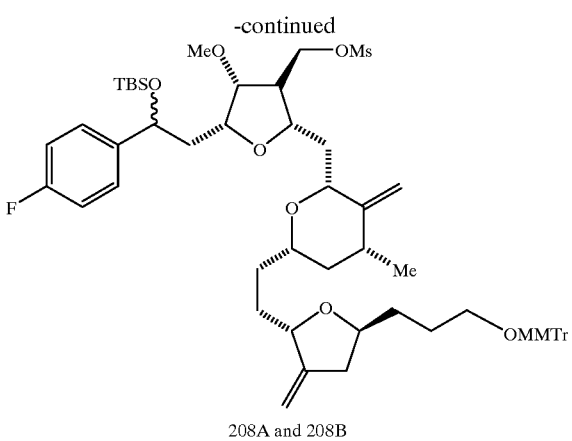

208A and 208B

Mesylates 208A and 208B Et$_3$N (19 μL, 0.13 mmol) and Ms$_2$O (10 mg, 0.056 mmol) were sequentially added to a solution of alcohol 207 (21.3 mg, 0.022 mmol) in CH$_2$Cl$_2$ (6 mL) at 0° C. After 30 min, saturated aqueous NaHCO$_3$ was added and the mixture was extracted with CH$_2$Cl$_2$ (3×). The combined extracts were washed with brine, dried over Na$_2$SO$_4$, concentrated and purified by preparative TLC (30% EtOAc-hexanes) to provide mesylates 208A (11.7 mg, 51%) and 208B (6.5 mg, 28%) as single C34 isomers.

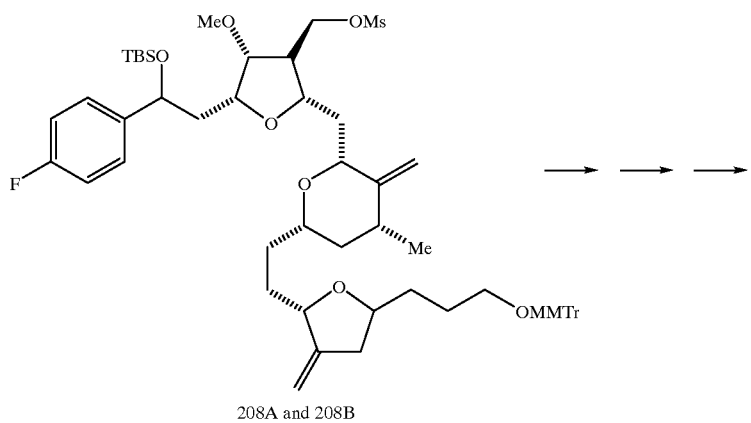

208A and 208B

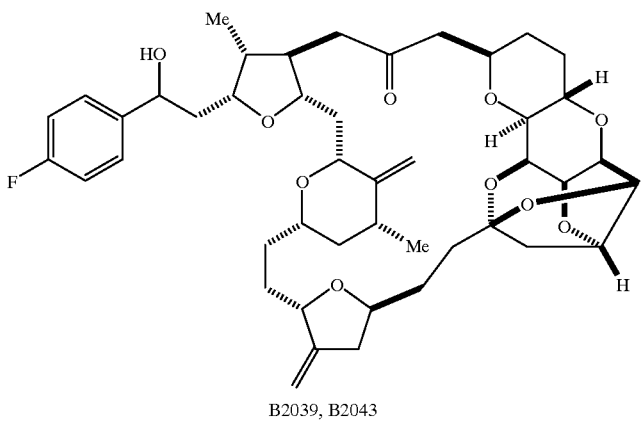

B2039, B2043

Synthesis of B2086, B2088, B2091

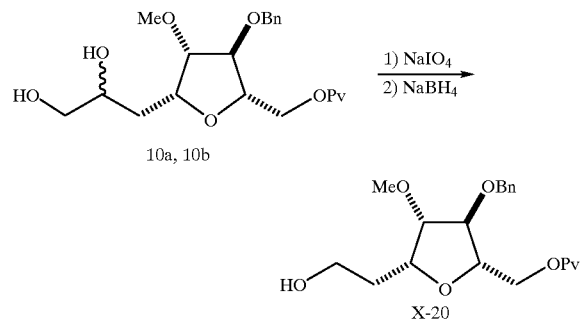

10a, 10b

Alcohol X-20 NaIO$_4$ (1.16 g, 5.4 mmol) was added to a solution of diols 10 a, b (1.19 g, 3.0 mmol) in MeOH-H$_2$O (4:1, 75 mL) at 0° C. The reaction mixture was allowed to warm to rt. After stirring for 40 min, the mixture was diluted with EtOAc, filtered through Celite, concentrated, and partitioned between brine and CH$_2$Cl$_2$. The separated aqueous layer was extracted with CH$_2$Cl$_2$ (2×). The combined organic layers were dried over Na$_2$SO$_4$ and concentrated to furnish the crude aldehyde intermediate.

NaBH$_4$ (228 mg, 6.0 mmol) was added to a solution of the aldehyde in MeOH-Et$_2$O (1:1, 40 mL) at 0° C. The mixture was stirred for 30 min, carefully quenched with saturated aqueous NH$_4$Cl, stirred for 20 min at rt and extracted with CH$_2$Cl$_2$ (3×). The combined extracts were dried over Na$_2$SO$_4$, concentrated and purified by flash chromatography (40% to 50% EtOAc-hexanes) to afford alcohol X-20 (1.02 g, 93% for two steps).

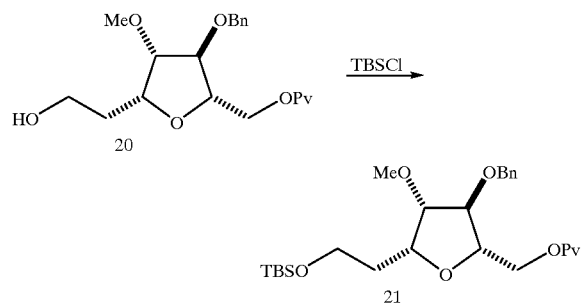

Silyl ether 21 Imidazole (0.94 g, 13.9 mmol) and TBSCl (0.59 g, 3.89 mmol) were added sequentially to a solution of alcohol X-20 (1.02 g, 2.78 mmol) in DMF (10 mL) at rt. After 14 h, the reaction mixture was diluted with saturated aqueous NH$_4$Cl and extracted with EtOAc (3×). The combined organic extracts were washed with H$_2$O, brine, dried over Na$_2$SO$_4$, concentrated and purified by flash chromatography (5% to 15% EtOAc-hexanes) to afford silyl ether 21 (1.3 g, 98%).

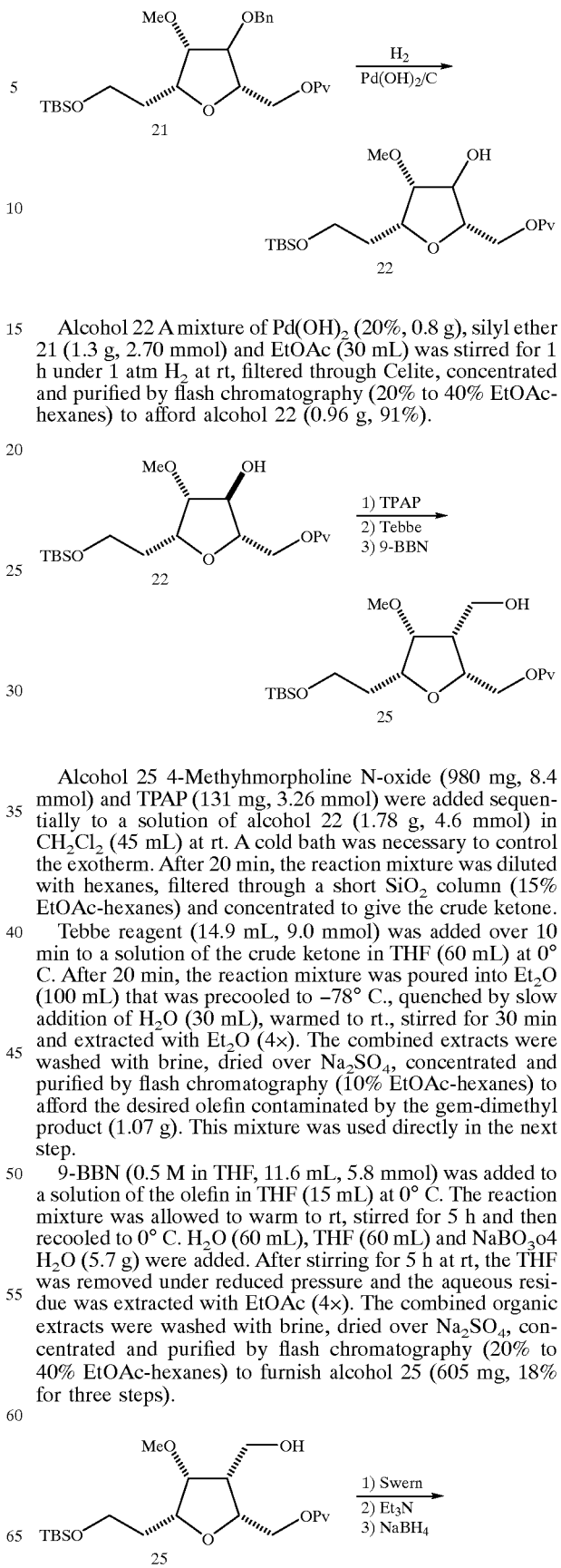

Alcohol 22 A mixture of Pd(OH)$_2$ (20%, 0.8 g), silyl ether 21 (1.3 g, 2.70 mmol) and EtOAc (30 mL) was stirred for 1 h under 1 atm H$_2$ at rt, filtered through Celite, concentrated and purified by flash chromatography (20% to 40% EtOAc-hexanes) to afford alcohol 22 (0.96 g, 91%).

Alcohol 25 4-Methylmorpholine N-oxide (980 mg, 8.4 mmol) and TPAP (131 mg, 3.26 mmol) were added sequentially to a solution of alcohol 22 (1.78 g, 4.6 mmol) in CH$_2$Cl$_2$ (45 mL) at rt. A cold bath was necessary to control the exotherm. After 20 min, the reaction mixture was diluted with hexanes, filtered through a short SiO$_2$ column (15% EtOAc-hexanes) and concentrated to give the crude ketone.

Tebbe reagent (14.9 mL, 9.0 mmol) was added over 10 min to a solution of the crude ketone in THF (60 mL) at 0° C. After 20 min, the reaction mixture was poured into Et$_2$O (100 mL) that was precooled to −78° C., quenched by slow addition of H$_2$O (30 mL), warmed to rt., stirred for 30 min and extracted with Et$_2$O (4×). The combined extracts were washed with brine, dried over Na$_2$SO$_4$, concentrated and purified by flash chromatography (10% EtOAc-hexanes) to afford the desired olefin contaminated by the gem-dimethyl product (1.07 g). This mixture was used directly in the next step.

9-BBN (0.5 M in THF, 11.6 mL, 5.8 mmol) was added to a solution of the olefin in THF (15 mL) at 0° C. The reaction mixture was allowed to warm to rt, stirred for 5 h and then recooled to 0° C. H$_2$O (60 mL), THF (60 mL) and NaBO$_3$o4 H$_2$O (5.7 g) were added. After stirring for 5 h at rt, the THF was removed under reduced pressure and the aqueous residue was extracted with EtOAc (4×). The combined organic extracts were washed with brine, dried over Na$_2$SO$_4$, concentrated and purified by flash chromatography (20% to 40% EtOAc-hexanes) to furnish alcohol 25 (605 mg, 18% for three steps).

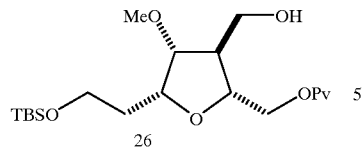
26

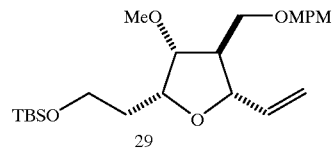
29

Alcohol 26 Using the procedure previously described, alcohol 25 (604 mg, 1.49 mmol) was sequentially oxidized, isomerized, and reduced. Purification by flash chromatography (20% to 40% EtOAc-hexanes) afforded alcohol 26 (550 mg, 91% for three steps).

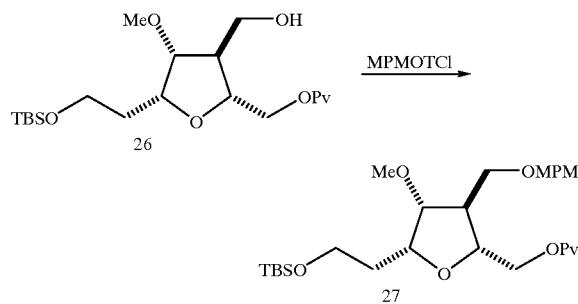

MPM-ether 27 $BF_3 \cdot OEt_2$ (0.05 M in $CH_2Cl_2$, 270 µL, 0.013 mmol) was added to a solution of alcohol 26 (545 mg, 1.35 mmol) and MPM-trichloroimidate (1.14 g, 4.0 mmol) in $CH_2Cl_2$ (40 mL) at 0° C. After 1 h, the reaction was quenched with saturated aqueous $NaHCO_3$, extracted with $CH_2Cl_2$, dried over $Na_2SO_4$, concentrated and purified by flash chromatography (10% to 15% EtOAc-hexanes) to afford MPM-ether 27 (580 mg, 82%).

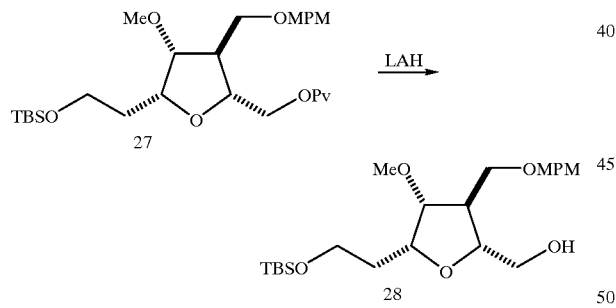

Alcohol 28 LAH (1 M in THF, 1.9 mL, 1.9 mmol) was added to a solution of MPM-ether 27 (580 mg, 1.11 mmol) in $Et_2O$ (100 mL) at 0° C. After 30 min, the reaction was quenched carefully with $H_2O$ (0.5 mL), and 1 N aqueous NaOH (0.5 mL), stirred for 1 h at rt, filtered through Celite, concentrated and purified by flash chromatography (30% to 50% EtOAc-hexanes) to afford alcohol 28 (460 mg, 95%).

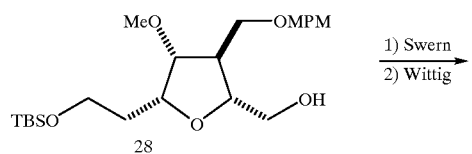

Olefin 29 DMSO (441 µL, 6.23 mmol) was added to a solution of oxalyl chloride (272 µL, 3.12 mmol) in $CH_2Cl_2$ (30 mL) at −78° C. After 15 min, a solution of alcohol 28 (458 mg, 1.04 mmol) in $CH_2Cl_2$ (15 mL) was added to the reaction mixture. After stirring for 1 h at −78° C., $Et_3N$ (1.3 mL, 9.35 mmol) was added. The reaction mixture was warmed to 0° C., stirred for 10 min, diluted with saturated aqueous $NH_4Cl$ and extracted with $CH_2Cl_2$ (3×). The combined organic extracts were dried over $Na_2SO$,, concentrated and filtered through a short $SiO_2$ column (20% to 30% EtOAc-hexanes) to provide the crude aldehyde.

n-BuLi (1.63 M, 1.4 mL, 2.28 mmol) was added dropwise to a solution of $CH_3PPh_3Br$ (815 mg, 2.28 mmol), THF (20 mL) and DMSO (7.5 mL) at 0° C. After 1 h, a solution of the aldehyde in THF (10 mL) was added. The reaction mixture was warmed to rt and stirred for 3 h. Saturated aqueous $NH_4Cl$ was added and the mixture was extracted with EtOAc (4×). The combined organic extracts were washed with $H_2O$, brine, dried over $Na_2SO_4$, concentrated and purified by flash chromatography (10% to 15% EtOAc-hexanes) to afford olefin 29 (380 mg, 95% yield for 2 steps).

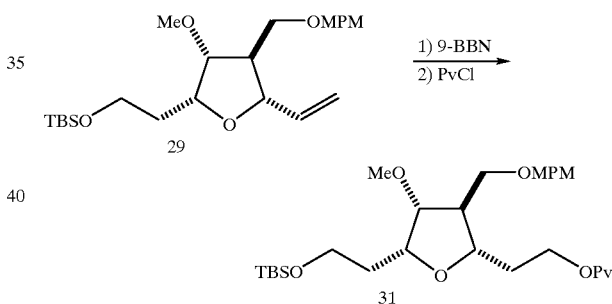

Compound 31 9-BBN (0.5 M in THF, 6 mL, 3 mmol) was added to a solution of olefin 29 (370 mg, 0.85 mmol) in THF (7 mL) at 0° C. The mixture was allowed to warm to rt and stirred for 1 h. After recooling to 0° C., $H_2O$ (30 mL), THF (20 mL), and $NaBO_3 \cdot 4 H_2O$ (2.8 g) were added. After stirring for 3 h at rt, the THF was removed under reduced pressure. The aqueous residue was extracted with EtOAc (4×), dried over $Na_2SO_4$, concentrated and purified by flash chromatography (25% to 50% EtOAc-hexanes) to afford alcohol 30 which was used directly in the next step.

Pivaloyl chloride (157 µL, 1.27 mmol) was added to a solution of alcohol 30 in $CH_2Cl_2$:pyridine (1:1 mixture, 10 mL) at rt. After 18 h, additional pivaloyl chloride (100 µL, 0.81 mmol) was added. After 1 h, the reaction mixture was cooled to 0° C., quenched with MeOH (0.5 mL), concentrated, diluted with brine and extracted with $CH_2Cl_2$ (4×). The combined organic extracts were dried over $Na_2SO_4$, concentrated and purified by flash chromatography (10% to 15% EtOAc-hexanes) to afford compound 31 (410 mg, 90% for two steps).

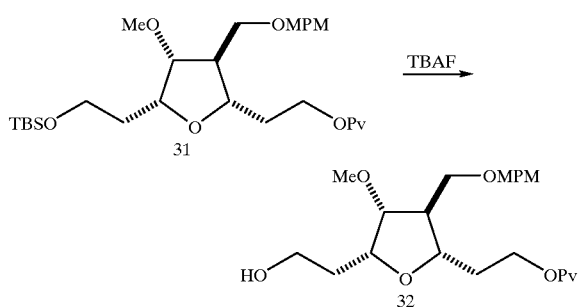

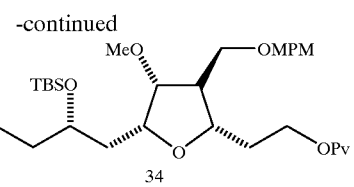

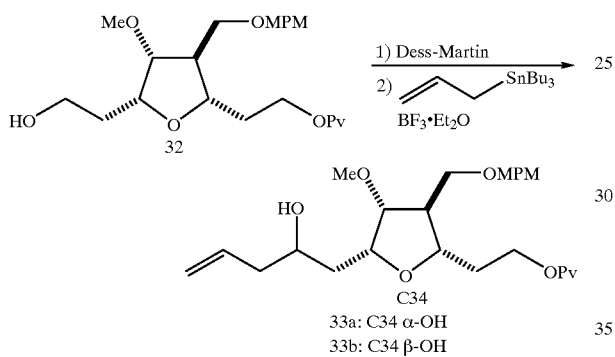

Alcohol 32 TBAF (1 M in THF;, 1.14 mL, 1.14 mmol) was added to a solution of 31 (410 mg, 0.761 mmol) in THF (5 mL) at rt. After 1.5 h, the reaction mixture was concentrated and purified by flash chromatography (40% EtOAc-hexanes to 100% EtOAc) to afford alcohol 32 (320 mg, 100%).

Alcohols 33a and 33b Dess-Martin periodinane (925 mg, 2.18 mmol) was added to a solution of alcohol 32 (309 mg, 0.727 mmol) in $CH_2Cl_2$ (19 mL) at rt. After 1 h, the reaction was diluted with $Et_2O$ and filtered through Celite. The filtrate was washed sequentially with a 1:9 mixture of saturated aqueous $NaHCO_3$—$Na_2S_2O_3$ and brine, dried over $Na_2SO_4$, concentrated and purified by flash chromatography (20% to 30% EtOAc-hexanes) to afford the desired aldehyde, which was taken immediately through the next step.

$BF_3 \cdot OEt_2$ (135 μL, 1.1 mmol) was added to a solution of the crude aldehyde, tri-n-butylallyltin (337 μL, 1.08 mmol) and $CH_2Cl_2$ (16 mL) at −78° C. After 1 h, the reaction was quenched with saturated aqueous $NaHCO_3$ and extracted with $CH_2Cl_2$ (3×). The combined organic extracts were dried over $Na_2SO_4$, concentrated and purified by MPLC (25% to 30% EtOAc-hexanes) to afford the major, more polar alcohol 33a (165 mg, 49% for two steps) and the minor less polar product 33b (90 mg, 27% for two steps).

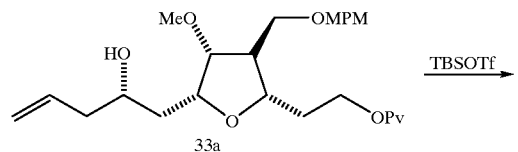

Compound 34 TBSOTf (163 μL, 0.710 mmol) was added to a solution of alcohol 33a (165 mg, 0.355 mmol), $Et_3N$ (247 μL, 1.78 mmol) and $CH_2Cl_2$ (5 mL) at 0° C. After 25 min, the reaction was quenched with saturated aqueous $NaHCO_3$, extracted with $CH_2Cl_2$ (3×), dried over $Na_2SO_4$, concentrated and purified by flash chromatography (15% to 20% EtOAc-hexanes) to afford compound 34 (200 mg, 98%).

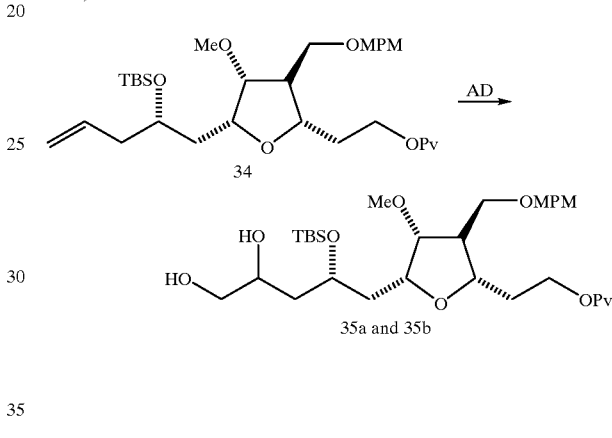

Diols 35a and 35b $OsO_4$ (0.1 M solution in toluene, 32 μL, 3.2 μmol) was added to a solution of $K_2CO_3$ (168 mg, 1.22 mmol), $K_3Fe(CN)_6$ (400 mg, 1.22 mmol), $(DHQ)_2PYR$ (11 mg, 12 μmol), $H_2O$ (3.2 mL) and t-BuOH (2.2 mL) at 0° C. Then a solution of olefin 34 (200 mg, 0.345 mmol) in t-BuOH (1 mL) was added to the reaction mixture. After 5 h at 0° C., $Na_2S_2O_5 \cdot 5 H_2O$ (200 mg) was added. The reaction mixture was warmed to rt, stirred for 30 min and extracted with $CH_2Cl_2$ (5×). The combined organic extracts were washed with brine, dried over $Na_2SO_4$, concentrated and purified by preparative TLC (70% EtOAc- hexanes) to afford the major, less polar diol 35a (118 mg, 56%), and minor, more polar diastereomeric product 35b (74 mg, 35%). The individual diastereomers were each carried forward separately.

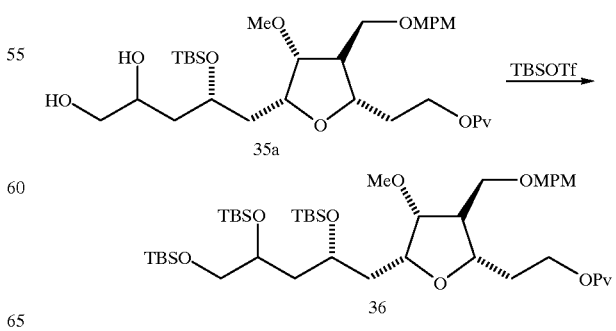

Compound 36 TBSOTf (177 μL, 0.77 mmol) was added to a solution of diol 35a (118 mg, 0.192 mmol), Et₃N (267 μL, 1.92 mmol) and CH₂Cl₂ (5 mL) at 0° C. After 25 min, the reaction was quenched with saturated aqueous NaHCO₃, extracted with CH₂Cl₂ (3×), dried over Na₂SO₄, concentrated and purified by flash chromatography (10% to 15% EtOAc-hexanes) to afford compound 36 (161 mg, 100%).

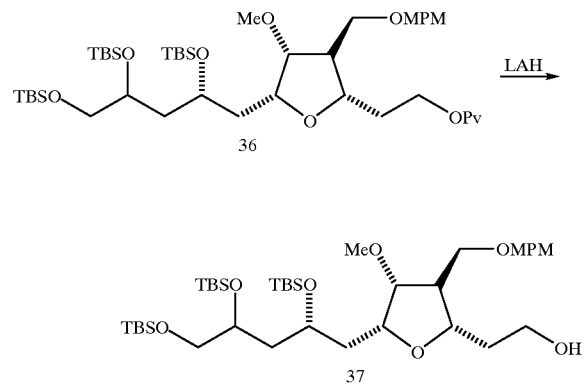

Alcohol 37 Using the procedure described previously for the preparation of alcohol 28, compound 36 (161 mg, 0.192 mmol) afforded alcohol 37 (135 mg, 93%) after purification by flash chromatography (20% to 40% EtOAc-hexanes).

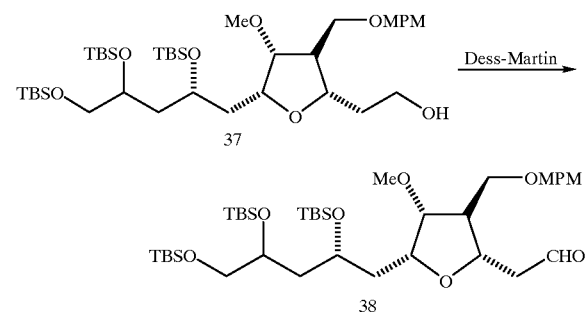

Aldehyde 38 Dess-Martin periodinane (227 mg, 0.535 mmol) was added to a solution of alcohol 37 (135 mg, 0.178 mmol) in CH₂Cl₂ (5 mL) at rt. After 1 h, the reaction mixture was diluted with Et₂O and filtered through Celite. The filtrate was washed sequentially with a 1:9 mixture of saturated aqueous NaHCO₃-Na₂S₂O₃ and brine, dried over Na₂SO₄, concentrated and purified by flash chromatography (10% to 20% EtOAc-hexanes) to afford aldehyde 38 (127 mg, 95%).

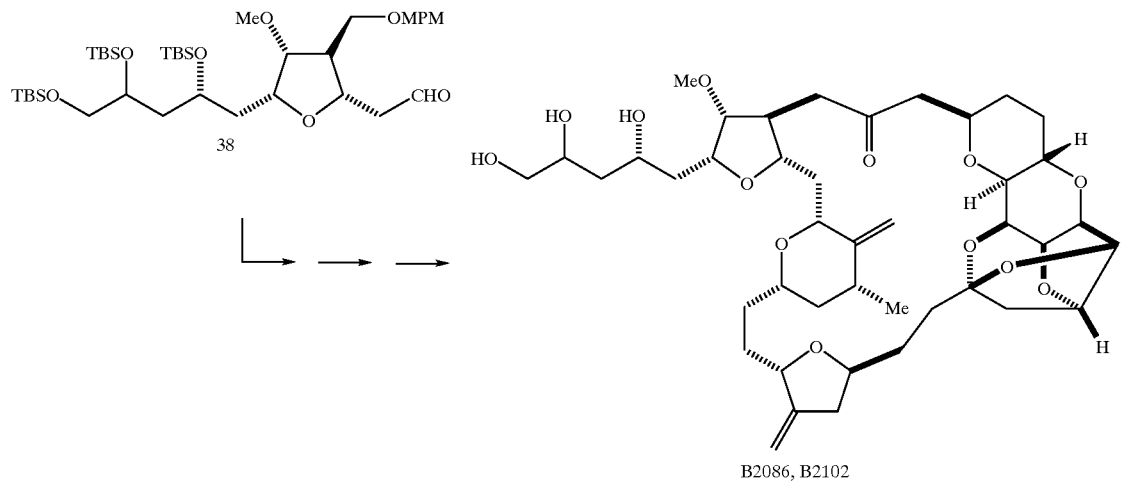

B2086, B2102 Each of the diastereomers obtained above were separately carried to final product in a manner similar to that described in scheme 6 for B1794. Diastereomer 35a afforded B2086. Diastereomer 35b afforded B2102.

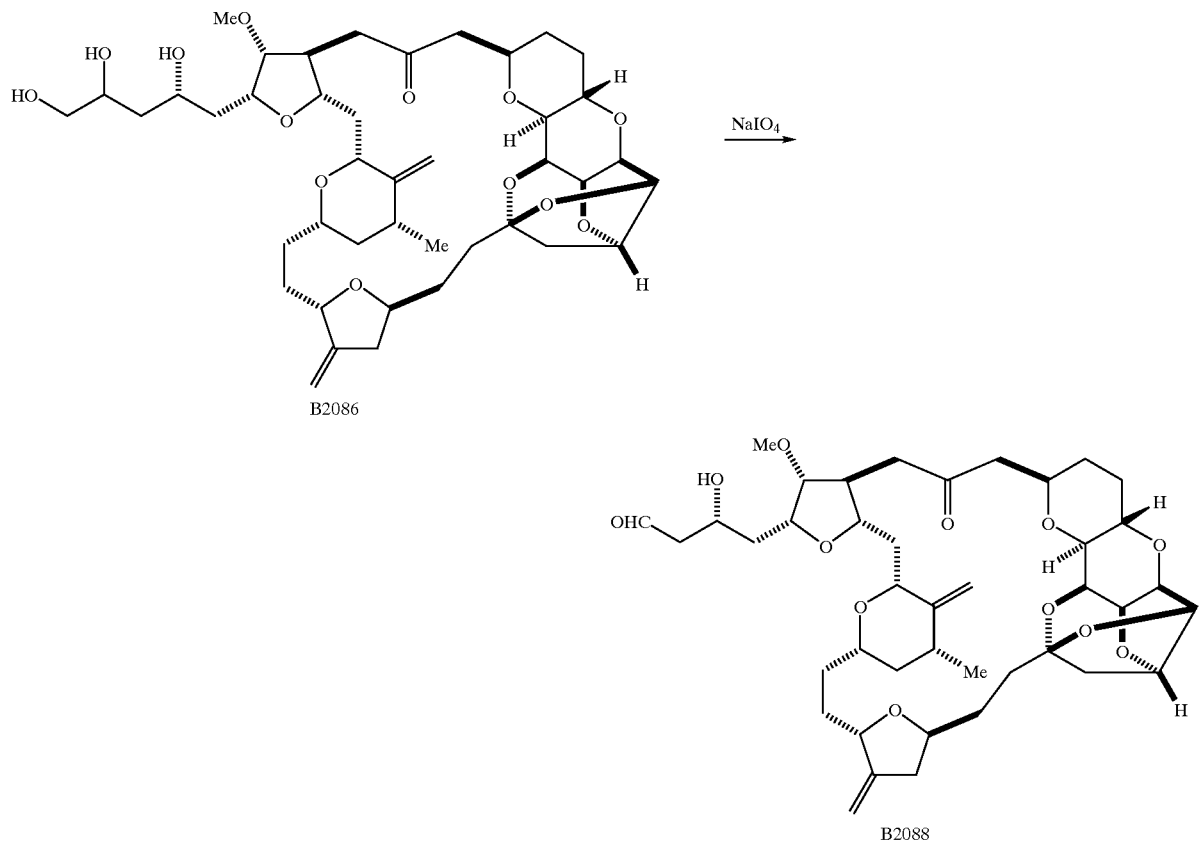
B2088 NaIO$_4$ was added to a solution of B2086 (1 mg, 1.29 μmol) in MeOH-H$_2$O (4:1, 1 mL) at rt. After 30 min, the reaction mixture was diluted with H$_2$O, extracted with CH$_2$Cl$_2$ (6×), dried over Na$_2$SO$_4$, and concentrated to afford B2088 (1.2 mg).
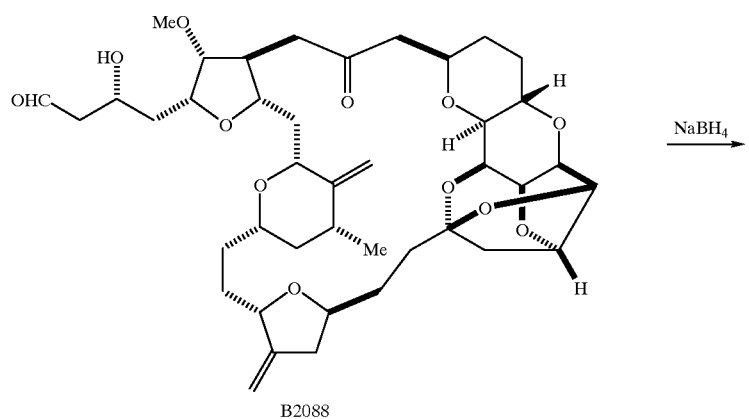

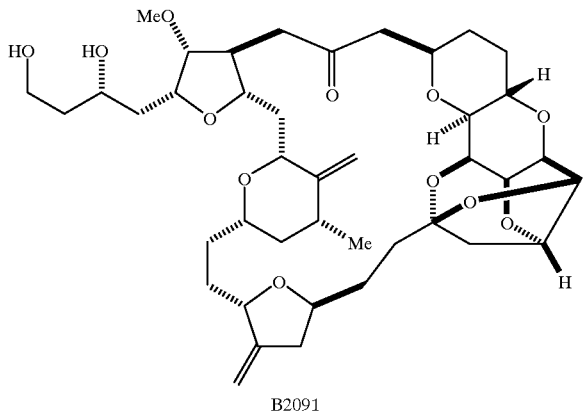

B2091

B2091 NaBH$_4$ (0.013 M in EtOH, 20 μL, 0.27 μmol) was added to a solution of B2088 (1 mg, 1.29 μmol) in MeOH—CH$_2$Cl$_2$ (4:1, 0.5 mL) at −78° C. Additional NABH$_4$ was periodically added with close monitoring of the reaction by TLC (total of 220 μL of the NaBH$_4$ solution was required). The reaction mixture was quenched at 0° C. with saturated aqueous NH$_4$Cl, stirred for 20 min at rt and extracted with CH$_2$Cl$_2$ (6×). The combined extracts were dried over Na$_2$SO$_4$, concentrated and purified by preparative TLC (7% MeOH-EtOAc) to furnish B2091 (0.40 mg, 50%).

Synthesis of B1933:

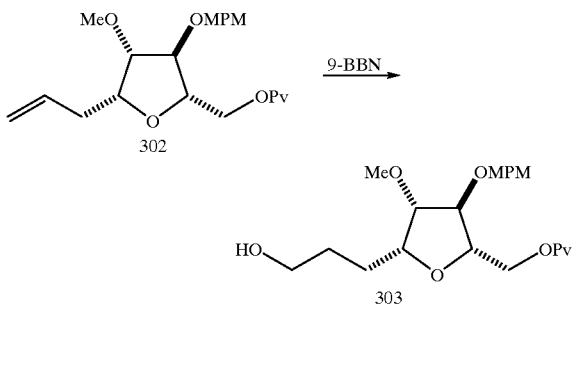

Alcohol 303 9-BBN (0.5 M in THF, 23 mL, 0.012 mmol) was added dropwise over 30 min to a solution of alkene 302 (1.51 g, 0.00386 mol) in THF (40 mL) at 0° C. After stirring at rt for 80 min, the mixture was cooled to 0° C. and H$_2$O (80 mL) was cautiously added followed by NaBO$_3$.4 H$_2$O (4.2 g, 0.027 mol). The mixture was stirred vigorously at rt for 2.3 h, then extracted with EtOAc (3×). The combined organic extracts were washed with brine, dried over Na$_2$SO$_4$, concentrated and purified by column chromatography (50% EtOAc-hexanes) to provide alcohol 303 (1.37 g, 87%).

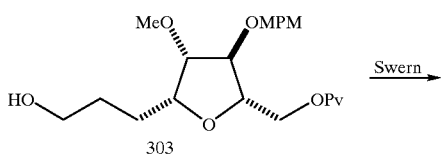

Aldehyde 304 Oxalyl chloride (88 μL, 1.00 mmol) was added dropwise to a solution of DMSO (142 μL, 2.00 mmol) in CH$_2$Cl$_2$ (20 mL) at −78° C. After 30 min, a solution of alcohol 303 (137 mg, 0.335 mmol) in CH$_2$Cl$_2$ (5 mL) was added and stirred at −78° C. for 1 h. Et$_3$N (420 μL, 3.01 mmol) was added and after 10 min the reaction was stirred for 10 min at 0° C. at which point saturated aqueous NH$_4$CL was added and the resulting mixture was extracted with CH$_2$Cl$_2$ (3×). The combined organic extracts were washed with brine, dried over Na$_2$SO$_4$, concentrated and purified by flash chromatography (50% EtOAc-hexanes) to provide intermediate aldehyde 304 (0.114 g, 84%) which was immediately used in the next step.

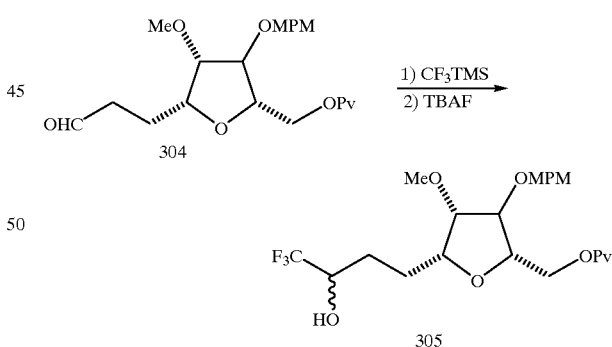

Alcohol 305 TBAF (1 M in THF, 5 μL, 0.005 mmol) was added to a solution of aldehyde 304 (0.114 g, 0.27 mmol) in CF$_3$TMS (0.5 M in THF, 1.1 mL, 0.54 mmol) at 0° C. After 20 min, a second portion of TBAF (1 M in THF, 100 μL, 0.1 μmmol) was added and the mixture was stirred for 10 min at which point excess TBAF (1 M in THE, 270 μL, 0.27 mmol) was added dropwise to cleave the intermediate silyl ether. After 30 min, the mixture was diluted with H$_2$O and extracted with EtOAc (3×). The organic extracts were washed with H$_2$O, brine, dried over Na$_2$SO$_4$, concentrated and purified by column chromatography (50% EtOAc-hexanes) to provide alcohol 305 (123 mg, 95%) as an inseparable 1:1 mixture of isomers.

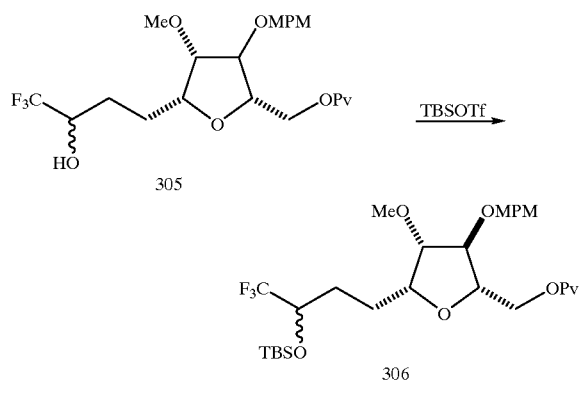

Silyl ether 306 TBSOTf (265 μL, 1.16 mmol) was added to a solution of alcohol 305 (123 mg, 0.257 mmol) and Et$_3$N (430 μL, 3.08 mmol) in CH$_2$Cl$_2$ (8 mL) at 0° C. After stirring at rt for 20 h, saturated aqueous NaHCO$_3$ was added, and the mixture was extracted with CH$_2$Cl$_2$ (3×). The combined organic extracts were washed with brine, dried over Na$_2$SO$_4$, concentrated and purified by column chromatography (20% EtOAc-hexanes) to provide silyl ether 306 (148 mg, 97%).

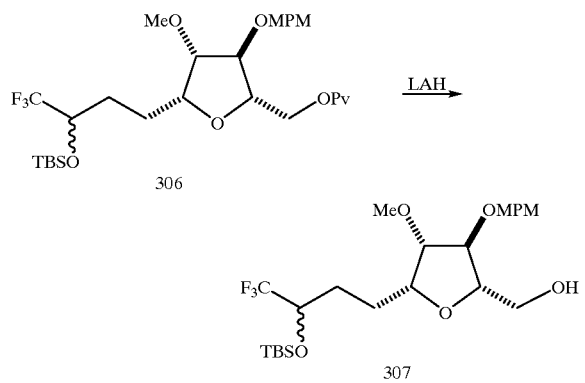

Alcohol 307 LAH (1 M in THF, 220 μL, 0.22 mmol) was added dropwise to a solution of silyl ether 306 (131 mg, 0.22 mmol) in Et$_2$O (5 mL) at 0° C. After 20 min, H$_2$O and 1 M NaOH were cautiously added. The mixture was stirred at rt 30 min, filtered through glass wool, concentrated and purified by column chromatography (50% EtOAc-hexanes) to provide alcohol 307 (112 mg, quant.).

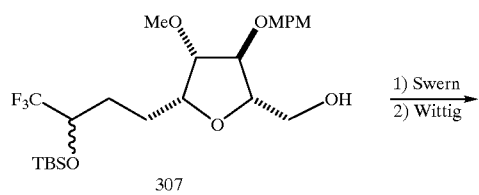

-continued

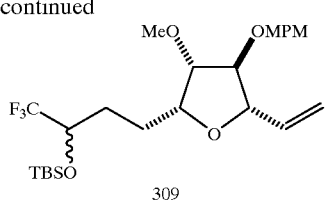

Alkene 309 Oxalyl chloride (58 μL, 0.66 mmol) was added dropwise to a solution of DMSO (94 μL, 1.3 mmol) in CH$_2$Cl$_2$ (10 mL) at −78° C. After 30 min, a solution of alcohol 307 (112 mg, 0.22 mmol) in CH$_2$Cl$_2$ (3 mL) was added. After 1 h, Et$_3$N (276 μL, 1.98 mmol) was added, and after 10 min at −78° C. the reaction was stirred at 0° C. for 10 min. Saturated aqueous NH$_4$Cl was added and the mixture was extracted with CH$_2$Cl$_2$ (3×). The combined organic extracts were washed with brine, dried over Na$_2$SO$_4$, concentrated and purified by flash chromatography (50% EtOAc-hexanes) to provide aldehyde 308 (101 mg, 91%) which was immediately used in the next step.

nBuLi (1.63 M in THF, 200 μL, 0.33 mmol) was added dropwise to a solution of CH$_3$PPh$_3$Br (118 mg, 0.33 mmol) in THF (3 mL) and DMSO (1.2 mL) at 0° C. After 70 min, a solution of aldehyde 308 (101 mg, 0.20 mmol) in THF (3 mL) was added and after 10 min at 0° C., the reaction was stirred at rt for 1 h. Saturated aqueous NH$_4$Cl was added and the mixture was extracted with EtOAc (3×). The combined organic extracts were washed with brine, dried over Na$_2$SO$_4$, concentrated and purified by column chromatography (20% EtOAc-hexanes) to provide alkene 309 (90.9 mg, 90%).

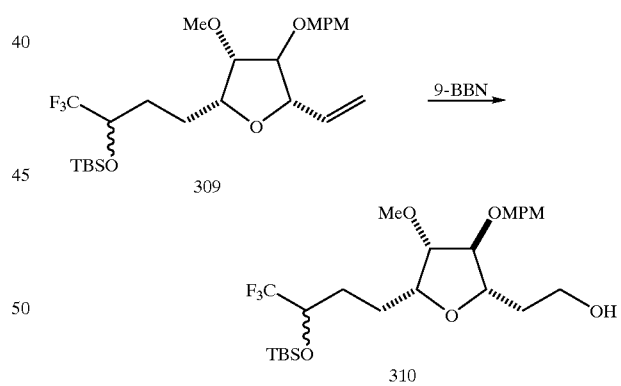

Alcohol 310 9-BBN (0.5 M in THF, 17 mL, 8.45 mmol) was added dropwise to a solution of alkene 309 (1.06 g, 2.11 mmol) in THF (30 mL) at 0° C. After stirring for 2.5 h at rt, the reaction was cooled to 0° C. and H$_2$O (60 mL) followed by NaBO$_3$.4 H$_2$O (3.25 g, 21.1 mmol) were cautiously added. The mixture was stirred vigorously at rt for 2 h, then diluted with H$_2$O and extracted with EtOAc (3×). The combined organic extracts were washed with brine, dried over Na$_2$SO$_4$, concentrated and purified by column chromatography (20% to 30% EtOAc-hexanes) to provide alcohol 310 (0.920 g, 84%).

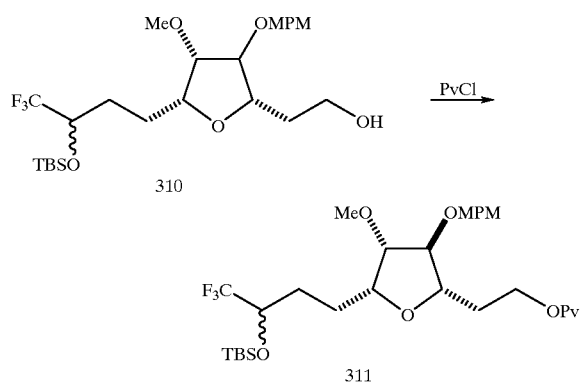

Pivaloate 311 A mixture of alcohol 310 (65.8 mg, 0.0126 mmol), pyridine (61 µL, 0.76 mmol) and PvCl (23 µL, 0.189 mmol) in CH$_2$Cl$_2$ (3 mL) was stirred at rt for 5 h. A second reaction utilizing alcohol 310 (0.92 g, 1.76 mmol) was run under similar conditions and both reactions were combined during the work-up: saturated aqueous NH$_4$Cl was added and the mixture was extracted with CH$_2$Cl$_2$ (3×). The combined organic extracts were washed with brine, dried over Na$_2$SO$_4$, concentrated and purified by column chromatography (20% EtOAc-hexanes) to provide pivaloate 311 (1.08 g, quant).

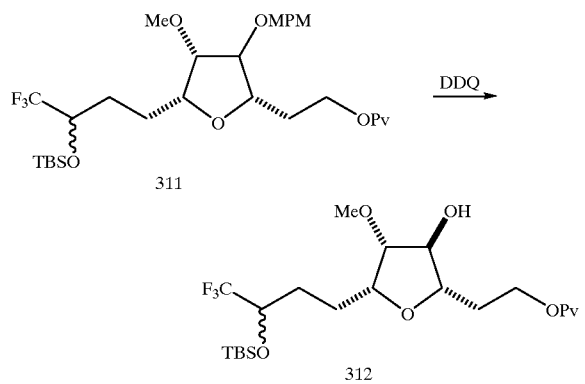

Alcohol 312 A mixture of ether 311 (0.811 g, 1.33 mmol), DDQ (6.1 g, 27 mmol) and 10:1 tBuOH: pH 7 phosphate buffer (42 mL) in CH$_2$Cl$_2$ (84 mL) was stirred vigorously in the dark at rt for 1.5 h, at which point additional DDQ (1.0 g, 4.4 mmol) was added. After 1 h, saturated aqueous NaHCO$_3$ was added and the mixture was extracted with CH$_2$Cl$_2$ (4×). The combined organic extracts were washed successively with saturated aqueous NaHCO$_3$ and brine, dried over Na$_2$SO$_4$, concentrated and purified by column chromatography (20% EtOAc-hexanes) to provide alcohol 312 (0.56 g, 87%) as well as recovered starting material 311 (97 mg, 12%).

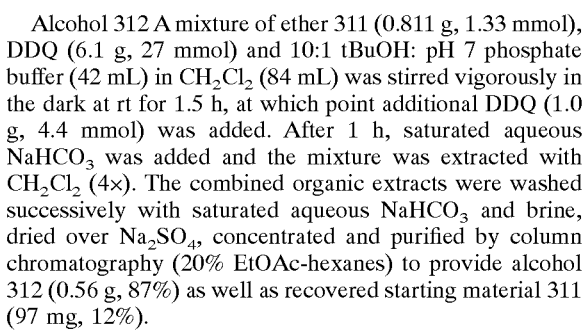

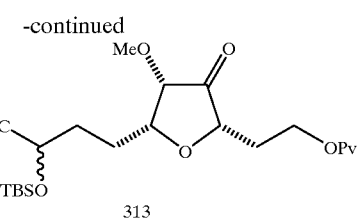

Ketone 313 Oxalyl chloride (21 µL, 0.12 mmol) was added dropwise to a solution of DMSO (34 µL, 0.48 mmol) in CH$_2$Cl$_2$ (3 mL) at −78° C. After 1 h, a solution of alcohol 312 (39.4 mg, 0.081 mmol) in CH$_2$Cl$_2$ (1.5 mL) was added and the mixture was stirred for 1.5 h. Et$_3$N (100 µL, 0.73 mmol) was added, and after 10 min the mixture was warmed to 0° C. Saturated aqueous NH$_4$Cl was added and the mixture was extracted with CH$_2$Cl$_2$ (3×). The combined organic extracts were washed with brine, dried over Na$_2$SO$_4$, concentrated and purified by flash chromatography (30% EtOAc-hexanes) to provide ketone 313 (36.6 mg, 93%) which was used immediately in the next step.

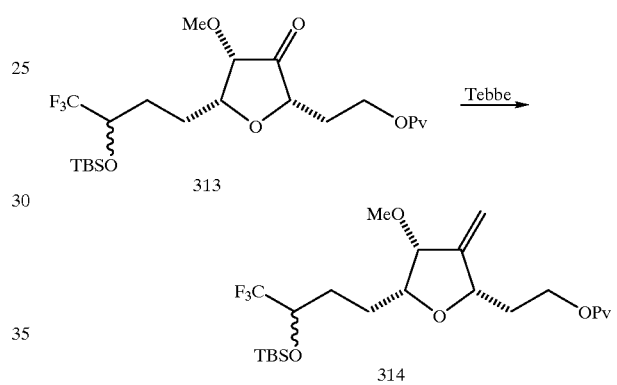

Alkene 314 Tebbe reagent (~0.65 M in toluene, 720 µL, 0.47 mmol) was added dropwise to a solution of ketone 313 (151 mg, 0.31 mmol) in THF (5 mL) at 0° C. After 15 min, H$_2$O was cautiously added and the mixture was extracted with EtOAc (3×). The combined organic extracts were washed with brine, dried over Na$_2$SO$_4$, concentrated and purified by column chromatography (10% EtOAc-hexanes) to provide alkene 314 (139 mg, 93%).

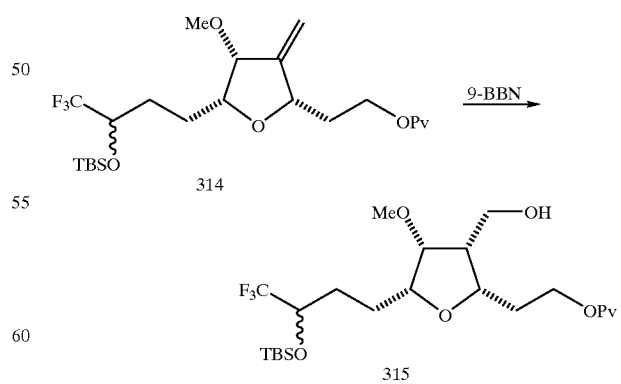

Alcohol 315 9-BBN (0.5 M in THF, 6.0 mL, 2.9 mmol) was added dropwise to a solution of alkene 314 (468 mg, 0.97 mmol) in THF (10 mL) at 0° C. The mixture was stirred at rt for 2 h at which point additional 9-BBN (0.5 M in THF, 500 μL, 0.25 mmol) was added. After 2.5 h, the mixture was cooled to 0° C. and H₂O (10 mL) followed by NaBO₃.4 H₂O (1.5 g, 9.7 mmol) were cautiously added. The mixture was stirred vigorously at rt for 5 h, diluted with H₂O and extracted with EtOAc (3×). The combined organic extracts were washed with brine, dried over Na₂SO₄, concentrated and purified by column chromatography (gradient 20% to 30% EtOAc-hexanes) to provide alcohol 315 (0.47 g, 97%).

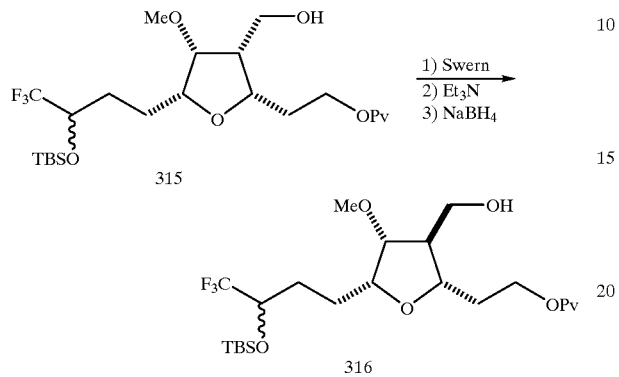

Alcohol 316 Oxalyl chloride (246 μL, 2.82 mmol) was added dropwise to a solution of DMSO (400 μL, 5.64 mmol) in CH₂Cl₂ (40 mL) at −78° C. After 1 h, a solution of alcohol 315 (0.47 g, 0.94 mmol) in CH₂Cl₂ (10 mL) was added and the mixture was stirred for 1 h. Et₃N (1.2 mL, 8.5 mmol) was added, and after 10 min the mixture was warmed to 0° C. and stirred for 10 min. Saturated aqueous NH₄Cl was added and the mixture was extracted with CH₂Cl₂ (3×). The combined organic extracts were washed with brine, dried over Na₂SO₄ and concentrated. The crude aldehyde was stirred in CH₂Cl₂ (20 mL) and Et₃N (2 mL) at rt overnight. Saturated aqueous NH₄CL was added and the mixture was extracted with CH₂Cl₂ (3×). The combined organic extracts were washed with brine, dried over Na₂SO₄, concentrated and purified by flash chromatography (30% EtOAc-hexanes) provided the epimerized aldehyde which was immediately dissolved in 1:1 Et₂O:EtOH (10 mL) and cooled to 0° C. NaBH₄ (35 mg, 0.94 mmol) was added and after 10 min the reaction was quenched with saturated aqueous NH₄Cl. The mixture was extracted with EtOAc (3×) and the combined organic extracts were washed with brine, dried over Na₂SO₄, concentrated and purified by column chromatography (30% EtOAc-hexanes) to provide alcohol 316 (0.410 g, 87% yield for 3 steps).

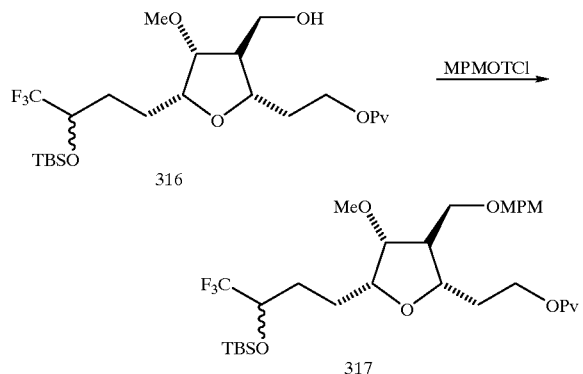

Ether 317 Alcohol 316 (60.7 mg, 0.12 mmol) and MPMOTCI (0.10 g, 0.36 mmol) were combined, azeotroped from toluene (3×) and dried under high vacuum overnight. CH₂Cl₂ (3 mL) was added and the mixture was cooled to 0° C. BF₃-OEt₂ (approx. 1 μL, 0.01 mmol) was added and after stirring for 10 min the reaction was quenched with saturated aqueous NH₄Cl. The mixture was extracted with CH₂Cl₂ (3×) and the combined extracts were washed with brine, dried over Na₂SO₄, concentrated and purified by preparative TLC (30% EtOAc-hexanes) to provide ether 317 (55.4 mg, 74%/o).

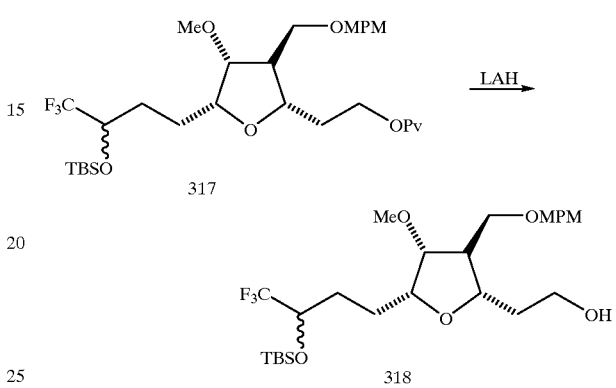

Alcohol 318 LAH (1 M in THF, 104 μL, 0.104 mmol) was added dropwise to a solution of ether 317 (54 mg, 0.087 mmol) in Et₂O(5 mL) at 0° C. After 30 min, H₂O and 1 M NaOH were cautiously added. The mixture was stirred at rt for 10 min, filtered through glass wool, concentrated and purified by column chromatography (30%–50% EtOAc-hexanes) to provide alcohol 318 (45.5 mg, 98%).

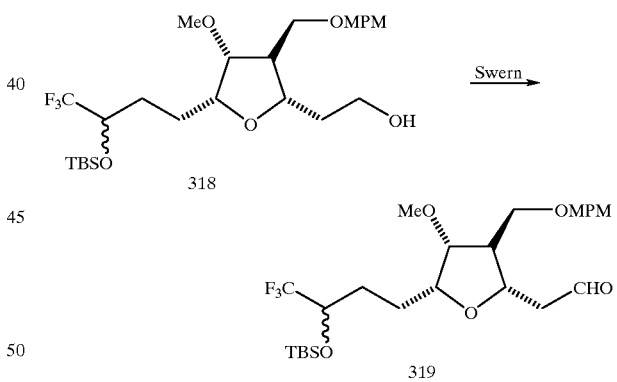

Aldehyde 319 Oxalyl chloride (11 μL, 0.13 mmol) was added dropwise to a solution of DMSO (18 μL, 0.25 mmol) in CH₂Cl₂ (2 mL) at −78° C. After 1.8 h, a solution of alcohol 318 (22.6 mg, 0.042 mmol) in CH₂Cl₂ (1 mL) was added and the mixture was stirred for 1 h. Et₃N (53 μL, 0.38 mmol) was added and after 10 min, the reaction was warmed to 0° C. and stirred 10 min. Saturated aqueous NH₄Cl was added and the mixture was extracted with CH₂Cl₂ (3×). The combined organic extracts were washed with brine, dried over Na₂SO₄, concentrated and purified by flash chromatography (20% EtOAc-hexanes) to provide aldehyde 319 (21.7 mg, 97%).

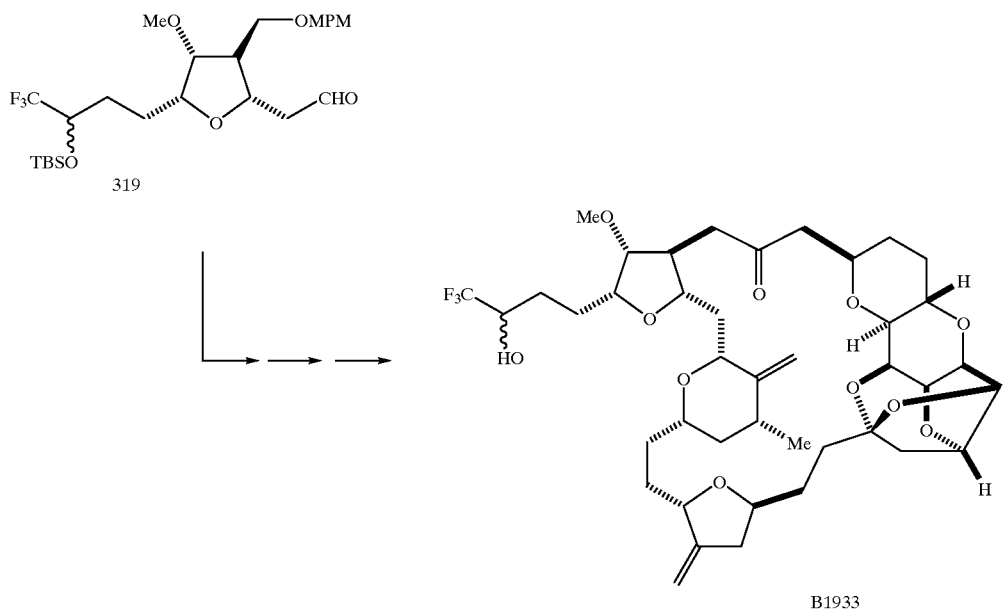

B1933 In a manner similar to that described in Scheme 6 for the synthesis of B1794, intermediate 319 was converted to B1933. HRMS (FAB): calcd for $C_{41}H_{57}F_3O_{11}+H$ 783.3931. Found: 783.3940.

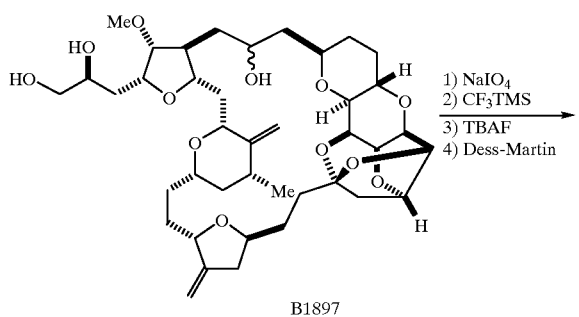

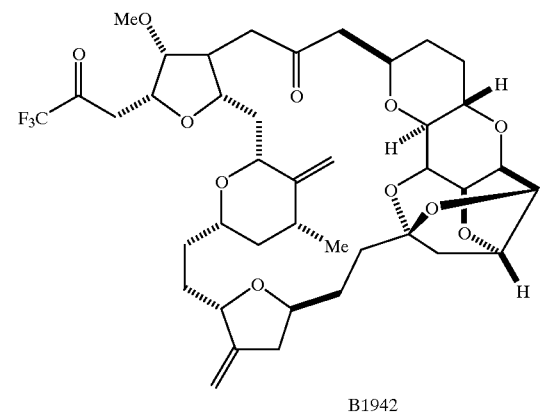

B1942 A mixture of B1897 (2 mg, 2.73 μmol), $NaIO_4$ (35 mg, 0.16 mmol), MeOH (0.8 mL) and $H_2O$ (0.2 mL) was stirred at rt for 30 min. The reaction mixture was then diluted with $H_2O$ (3 mL) and extracted with $CH_2Cl_2$ (6×) and EtOAc (2×). The combined organic phases were dried over $Na_2SO_4$ and purified by column chromatography (5% MeOH—$CH_2Cl_2$) to give the desired aldehyde.

This material was dissolved in THF (0.1 mL), cooled to at 0° C. and treated with 0.5 M $CF_3TMS$ in THF (30 μL, 15 mmol) followed by 0.05 M TBAF in THF (5 mL, 0.025 mmol). After stirring for 30 min, the reaction mixture was diluted with saturated aqueous $NaHCO_3$ (2 mL) and $H_2O$ (1 mL), extracted with EtOAc (6×), dried over $Na_2SO_4$, filtered and concentrated to give the crude bis-TMS ether.

This material was dissolved in THF (0.5 mL) and treated with 1 M TBAF in THF containing 0.5 M imidazole hydrochloride (8 μL, 8 μmol) at rt for 30 min. The reaction mixture was eluted through a $SiO_2$ column (50% EtOAc-hexanes to EtOAc) to afford the diol intermediate.

A mixture of this product and Dess-Martin periodinane (10 mg, 24 mmol) in $CH_2Cl_2$ (0.5 mL) was stirred at rt for 1 h, diluted with $Et_2O$ (5 mL) and filtered through Celite. The filtrate was concentrated and purified by preparative TLC (50% EtOAc-hexanes) to furnish B1942 (1.5 mg, 72% for 5 steps). HRMS (FAB): calcd for $C_{40}H_{55}F_3O_{11}+H$ 767.3516. Found: 767.3542

Synthesis of B2070/B2073:

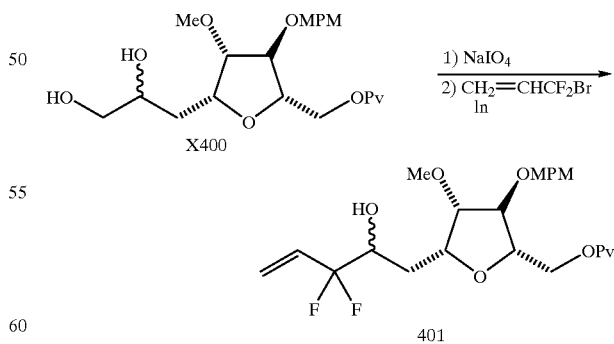

Alcohol 401 A mixture of $NaIO_4$ (375 mg, 1.74 mmol), X400 (674 mg, 1.58 mmol), MeOH (16 mL) and $H_2O$ (4 mL) was stirred at rt for 1 h. After dilution with $H_2O$, the mixture was extracted with $CH_2Cl_2$ (4×) and the combined organic extracts were dried over $Na_2SO_4$, concentrated and purified by flash chromatography (30% EtOAc-hexanes) to provide the intermediate aldehyde (570 mg), which was immediately dissolved in DMF (15 mL). Indium (275 mg, 2.4 mmol) and 3-bromo-3,3-difluoropropene (240 μL, 2.4 mmol) were added and after stirring at rt for 17 h, H$_2$O and 0.1 M HCl were added. The mixture was extracted with EtOAc (3×) and the combined organic extracts were washed successively with H$_2$O and brine, dried over Na$_2$SO$_4$, concentrated and purified by column chromatography (20% to 30% EtOAc-hexanes) to provide alcohol 401 as a 1:1 mixture of C34 isomers (605 mg, 81% for 2 steps).

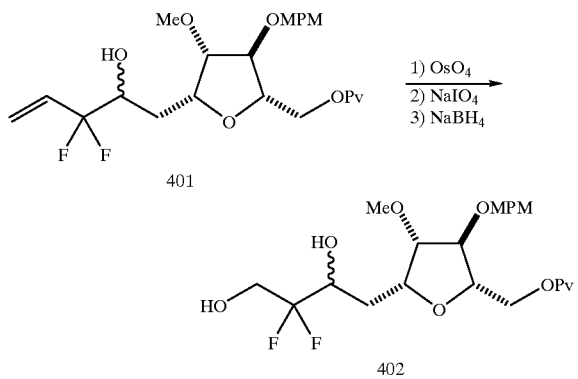

Diol 402 A mixture of OsO$_4$ (1 xstal), alcohol 401 (605 mg, 1.28 mmol), 4-methylmorpholine N-oxide (0.45 g, 3.84 mmol), acetone (30 mL) and H$_2$O (6 mL) was stirred at rt for 29 h. Additional OsO$_4$ (3 xtals) and 4-methylmorpholine N-oxide (0.1 g, 0.8 mmol) were added and after 2 days saturated aqueous Na$_2$S$_2$O$_3$ was added. The mixture was extracted with CH$_2$Cl$_2$ (6×) and the combined organic extracts were dried over Na$_2$SO$_4$ and concentrated. The crude intermediate triol was immediately dissolved in 4:1::MeOH:H$_2$O (25 mL) and NaIO$_4$ (0.41 g, 1.9 mmol) was added. After stirring vigorously at rt for 2 h, the mixture was diluted with H$_2$O, extracted with CH$_2$Cl$_2$ (3×) and the combined organic extracts were dried over Na$_2$SO$_4$ and concentrated to provide the intermediate aldehyde which was immediately dissolved in 1:1 EtOH-Et$_2$O (30 mL) and cooled to 0° C. NaBH$_4$ (48 mg, 1.3 mmol) was added and after 20 min the reaction was quenched with H$_2$O and extracted with CH$_2$Cl$_2$ (4×). The combined organic extracts were dried over Na$_2$SO$_4$, concentrated and purified by column chromatography (50% EtOAc-hexanes) to provide diol 402 (485 mg, 80% for 3 steps).

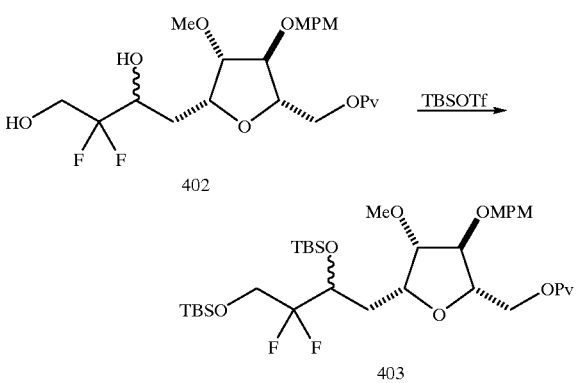

Silyl ether 403 TBSOTf (2.3 mL, 10 mmol) was added dropwise to a mixture of diol 402 (485 mg, 1.0 mmol), Et$_3$N (2.8 mL, 20 mmol) and CH$_2$Cl$_2$ (30 mL) at 0° C. After stirring for 1 h at rt, saturated aqueous NH$_4$Cl was added and the mixture was extracted with CH$_2$Cl$_2$ (3×). The combined organic extracts were washed with brine, dried over Na$_2$SO$_4$, concentrated and purified by column chromatography (20% EtOAc-hexanes) to provide silyl ether 403 (668 mg, 95%).

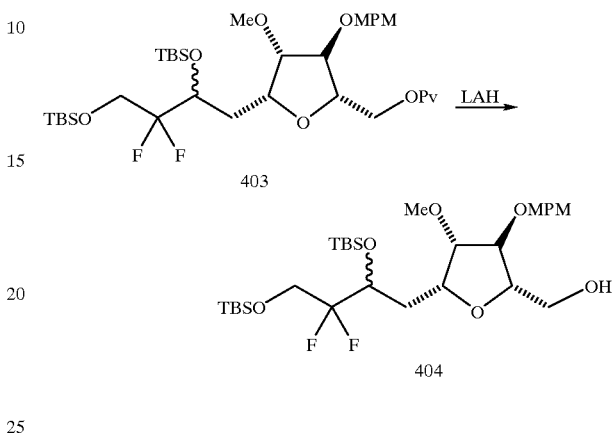

Alcohol 404 LAH (1 M in THF, 2.8 mL, 2.8 mmol) was added dropwise to a solution of silyl ether 403 (668 mg, 0.948 mmol) in Et$_2$O (60 mL) at 0° C. After 15 min, H$_2$O and 1 M NaOH were cautiously added. The mixture was stirred at rt for 20 min, filtered through glass wool, concentrated and purified by column chromatography (30% EtOAc-hexanes) to provide alcohol 404 (500 mg, 85%).

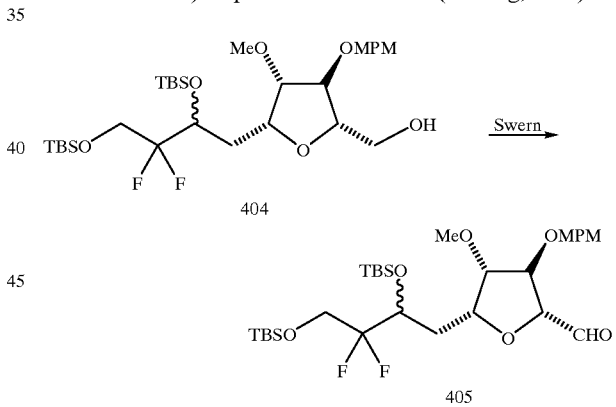

Aldehyde 405 Oxalyl chloride (210 μL, 2.42 mmol) was added dropwise to a solution of DMSO (345 μL, 4.84 mmol) in CH$_2$Cl$_2$ (30 mL) at −78° C. After 1 h, a solution of alcohol 404 (500 mg, 0.806 mmol) in CH$_2$Cl$_2$ (10 mL) was added. After 40 min, Et$_3$N (1.0 mL, 7.2 mmol) was added. After stirring at −78° C. for 10 min, the reaction mixture was warmed to 0° C. and stirred for an additional 10 min. Saturated aqueous NH$_4$Cl was added and the mixture was extracted with CH$_2$Cl$_2$ (3×). The combined organic extracts were washed successively with H$_2$O, brine, dried over Na$_2$SO$_4$ and concentrated. Purification by flash chromatography (30% EtOAc-hexanes) provided aldehyde 405 (486 mg, 98%) which was immediately used in the next step.

111

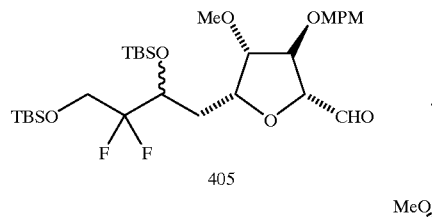

405

Wittig →

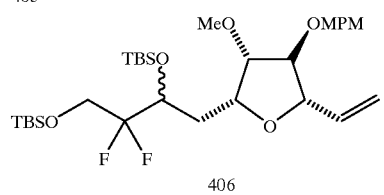

406

Alkene 406 nBuLi (1.63 M, 860 μL, 1.4 mmol) was added dropwise to a solution of CH₃PPh₃Br (500 mg, 1.4 mmol) in THF (15 mL) and DMSO (6 mL) at 0° C. After 1 h, a solution of aldehyde 405 (486 mg) in THF (15 mL) was added. The reaction mixture was warmed to rt and stirred for 30 min. Saturated aqueous NH₄Cl was added, the mixture was extracted with EtOAc (3×) and the combined extracts were washed successively with H₂O and brine, dried over Na₂SO₄, concentrated and purified by column chromatography (20% EtOAc-hexanes) to provide alkene 406 (450 mg, 93%).

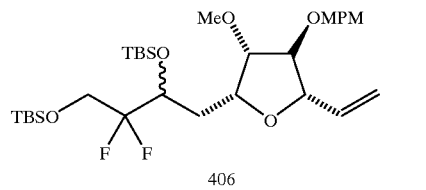

406

1) 9-BBN
2) PvCl →

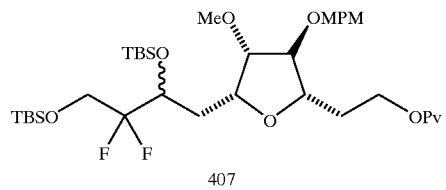

407

Ester 407 9-BBN (0.5 M in THF, 9.0 mL, 4.5 mmol) was added dropwise to a solution of alkene 406 (0.460 g, 0.746 mmol) in THF (10 mL) at 0° C. After warming to rt, the mixture was stirred for 3 h and two additional portions of 9-BBN (0.5 M in THF, 3.0 mL, 1.5 mmol) were added at 30 min intervals. The reaction mixture was recooled to 0° C., whereupon THF (10 mL), H₂O (10 mL) and NaBO₃.4 H₂O (1.72 g, 11.2 mmol) were cautiously added. The mixture was stirred vigorously at rt for 1.5 h, and additional NaBO₃.4 H₂O (1.0 g, 6.5 mmol) was added. After 2 h the mixture was diluted with H₂O and extracted with EtOAc (3×). The combined extracts were washed with brine, dried over Na₂SO₄, concentrated and purified by column chromatography (20% to 30% EtOAc-hexanes) to provide the intermediate alcohol (509 mg) which was immediately dissolved in CH₂Cl₂ (10 mL) and treated with pyridine (600 μL, 7.5 mmol) and PvCl (275 μL, 2.2 mmol). After 6 h, saturated aqueous NH₄Cl was added and the mixture was extracted with CH₂Cl₂ (3×). The combined organic extracts were washed with brine, dried over Na₂SO₄, concentrated and purified by column chromatography (20% to 30% EtOAc-hexanes) to provide ester 407 (423 mg, 79% for 2 steps).

112

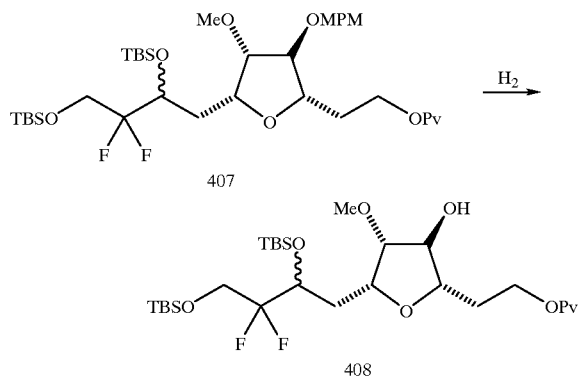

407

H₂ →

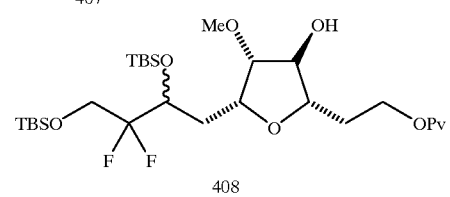

408

Alcohol 408 A mixture of ester 407 (11 mg, 0.015 mmol) and Pd(OH)₂/C (10 mg) in EtOAc (500 μL) was stirred vigorously under a H₂ atmosphere at rt for 6 h. The mixture was filtered through Celite, concentrated and purified by column chromatography (30% EtOAc-hexanes) to provide alcohol 408 (9.4 mg, quant).

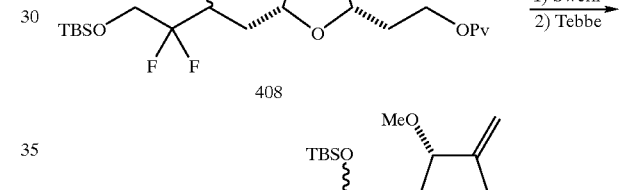

408

1) Swern
2) Tebbe →

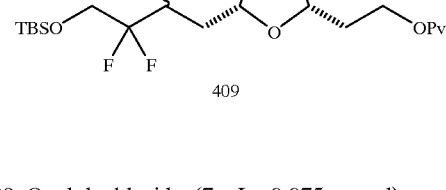

409

Alkene 409 Oxalyl chloride (7 μL, 0.075 mmol) was added dropwise to a solution of DMSO (11 μL, 0.15 mmol) in CH₂Cl₂ (2 mL) at −78° C. under N₂. After 40 min, a solution of alcohol 408 (15.2 mg, 0.025 mmol) in CH₂Cl₂ (1 mL) was added and the reaction was stirred at −78° C. for 1 h. Et₃N (31 μL, 0.22 mmol) was added, and after stirring for 10 min the mixture was warmed to 0° C. After 10 min, the reaction mixture was quenched with saturated aqueous NH₄Cl and extracted with CH₂Cl₂ (3×). The combined extracts were washed successively with H₂O and brine, dried over Na₂SO₄ and concentrated. After flash chromatography (30% EtOAc-hexanes), the intermediate ketone (13 mg) was immediately dissolved in THF (500 μL) and treated with Tebbe reagent (~0.65 M in toluene, 62 μL, 0.040 mmol) at 0° C. After 1.5 h additional Tebbe reagent (~0.65 M in toluene, 62 μL, 0.040 mmol) was added and after 10 min H₂O and then brine were cautiously added. The mixture was extracted with EtOAc (3×) and the combined organic extracts were washed with brine, dried over Na₂SO₄, concentrated and purified by column chromatography (10% EtOAc-hexanes) to provide alkene 409 (11.9 mg, 80% for 2 steps).

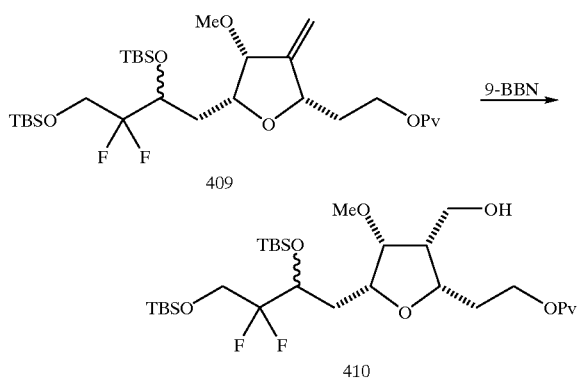

409, 410

Alcohol 410 9-BBN (0.5 M in THF, 1.5 mL, 0.72 mmol) was added dropwise to a solution of alkene 409 (0.144 g, 0.242 mmol) in THF (2 mL) at 0° C. After warming to rt, the mixture was stirred for 3 h. The reaction mixture was recooled to 0° C., whereupon THF (2 mL), H$_2$O (2 mL) and NaBO$_3$.4 H$_2$O (0.38 g, 2.4 mmol) were cautiously added. The mixture was stirred vigorously at rt for 4 h, diluted with H$_2$O and extracted with EtOAc (3×). The combined extracts were washed with brine, dried over Na$_2$SO$_4$, concentrated and purified by column chromatography (20% EtOAc-hexanes) to provide alcohol 410 (0.140 g, 94%).

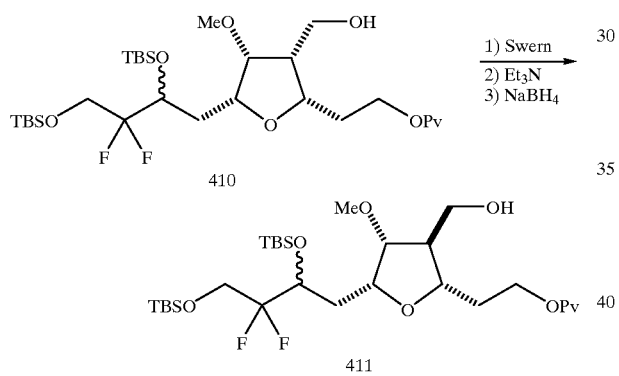

410, 411

Alcohol 411 Oxalyl chloride (26 μL, 0.30 mL) was added dropwise to a solution of DMSO (43 μL, 0.60 mmol) in CH$_2$Cl$_2$ (4 mL) at −78° C. After 1 h, a solution of alcohol 410 (57 mg, 0.093 mmol) in CH$_2$Cl$_2$ (2 mL) was added. After 45 min, Et$_3$N (125 μL, 0.90 mmol) was added. After stirring at −78° C. for 10 min, the reaction mixture was warmed to 0° C. and stirred for an additional 10 min. Saturated aqueous NH$_4$Cl was added and the mixture was extracted with CH$_2$Cl$_2$ (3×). The combined organic extracts were washed with brine, dried over Na$_2$SO$_4$ and concentrated. The crude product was dissolved in CH$_2$Cl$_2$ (4 mL), treated with Et$_3$N (400 μL) and stirred at rt for 15 h. Saturated aqueous NH$_4$Cl was added and the mixture was extracted with CH$_2$Cl$_2$ (3×). The combined organic extracts were washed with brine, dried over Na$_2$SO$_4$, concentrated and purified by flash chromatography (30% EtOAc-hexanes) to provide the intermediate aldehyde (48 mg), which was immediately dissolved in 1:1 Et$_2$O-EtOH (4 mL), cooled to 0° C. and treated with solid NaBH$_4$ (~4 mg, 0.09 mmol). After stirring for 15 min, saturated aqueous NH$_4$Cl was cautiously added and the mixture was extracted with EtOAc (3×). The combined extracts were washed with brine, dried over Na$_2$SO$_4$, concentrated and purified by column chromatography (20% to 30% EtOAc-hexanes) to provide alcohol 411 (45.6 mg, 80% for 3 steps).

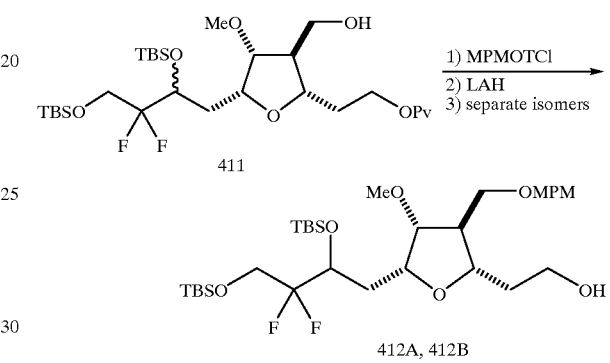

411

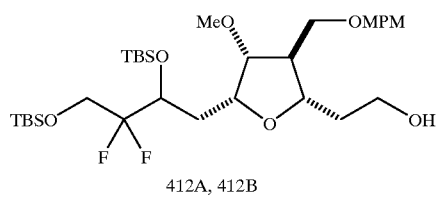

412A, 412B 412A and 412B Alcohol 411 (120 mg, 0.196 mmol) and MPMOTCI (0.17 g, 0.59 mmol) were combined, azeotroped from toluene (3×) and dried under high vacuum for 1 h. CH$_2$Cl$_2$ (9 mL) was added and the mixture was cooled to 0° C. BF$_3$.OEt$_2$ (0.016 M in CH$_2$Cl$_2$, 125 μL, 0.002 mmol) was added dropwise and after stirring for 20 min, the reaction was quenched with saturated aqueous NH$_4$Cl. The mixture was extracted with CH$_2$Cl$_2$ (3×) and the combined extracts were washed with brine, dried over Na$_2$SO$_4$, concentrated and purified by preparative TLC (20% EtOAc-hexanes) to provide the intermediate MPM ether which contained some close-running impurities. This material was immediately dissolved in Et$_2$O (10 mL) and treated with LAH (1M in THF, 300 μL, 0.300 mmol) at 0° C. After 10 min, H$_2$O and 1 M NaOH were added, and after stirring for 10 min at rt, the mixture was filtered through Celite, concentrated and purified by preparative TLC (35% EtOAc-hexanes) to provide 412A (49 mg, 39% for 2 steps) as a single C34 isomer and 412B (46 mg, 36% for 2 steps) as a 9:1 mixture of C34 isomers.

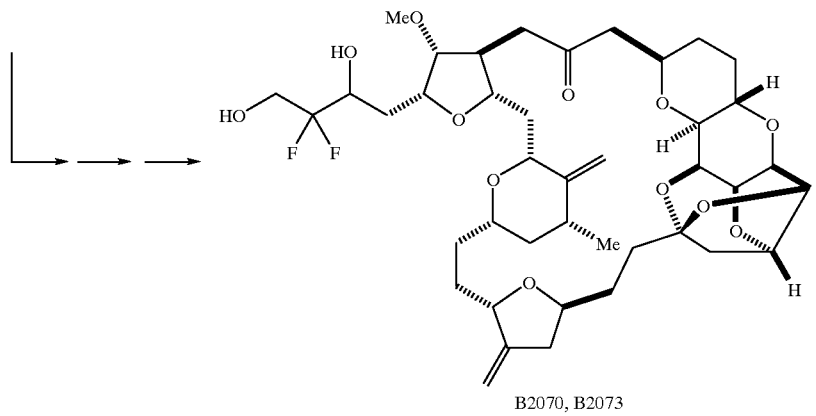

B2070, B2073

B2070 and B2073 In a manner similar to that described in Schemes 4 and 6 for the synthesis of B1794, intermediates 412A and 412B were converted to B2070 and B2073, respectively. For B2070: HRMS (FAB): calcd for $C_{41}H_{58}F_2O_{12}$+Na 803.3794. Found: 803.3801. For B2073: HRMS (FAB): calcd for $C_{41}H_{58}F_2O_{12}$+Na 803.3793. Found: 803.3781

Synthesis of B1963:

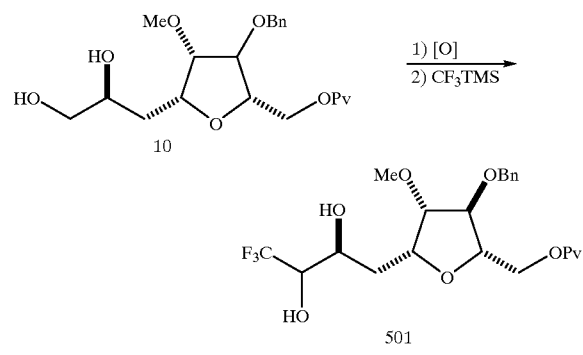

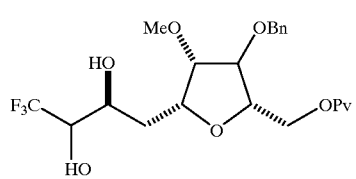

Diol 501 (64) Saturated aqueous $NaHCO_3$ (21 mL) and KBr (89 mg, 0.75 mmol) were added to a solution of diol 10 (1.35 g, 3.4 mmol) in $CH_2Cl_2$ (34 mL). The mixture was cooled to 0° C., and 4-methoxy-2,2,6,6-tetramethyl-1-piperidinyloxy (0.05 M in $CH_2Cl_2$, 7.45 mL, 0.37 mmol) and NaOCl (0.07 M in $H_2O$, 5.6 mL, 0.39 mmol) were sequentially added. After 1 h, the reaction mixture was quenched with saturated aqueous $Na_2S_2O_3$, diluted with saturated aqueous $NaHCO_3$ and extracted with $CH_2Cl_2$ (3×). The combined extracts were dried over $Na_2SO_4$, concentrated and dissolved in THF (21 mL).

After cooling to 0° C., $CF_3TMS$ (1.5 g, 10.5 mmol) and TBAF (0.1 M in THF, 680 µL, 0.068 mmol) were sequentially added. After stirring for 40 min, additional TBAF (1 M in THF, 8.3 mL, 8.3 mmol) was added. After 30 min, the reaction was quenched with $H_2O$ and extracted with EtOAc (3×). The combined organic extracts were washed with brine, dried over $Na_2SO_4$, concentrated and purified by flash chromatography (30%, 40%, 50% EtOAc-hexanes followed by EtOAc) to afford a 2:1 mixture of diols (553 mg, 35%). Separation by MPLC (1.5% MeOH—$CH_2Cl_2$) gave the major, more polar isomer 501 (64) (340 mg, 22%) and the minor, less polar isomer (152 mg, 10%).

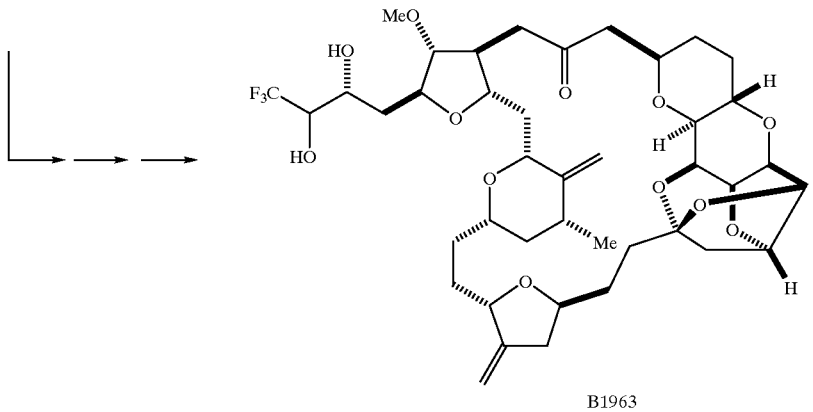

B1963

B1963 In a manner similar to that described in Schemes 4 and 6 for the synthesis of B1794, intermediate 501 was converted to B1963.

Synthesis of B2320 and Related Analogs

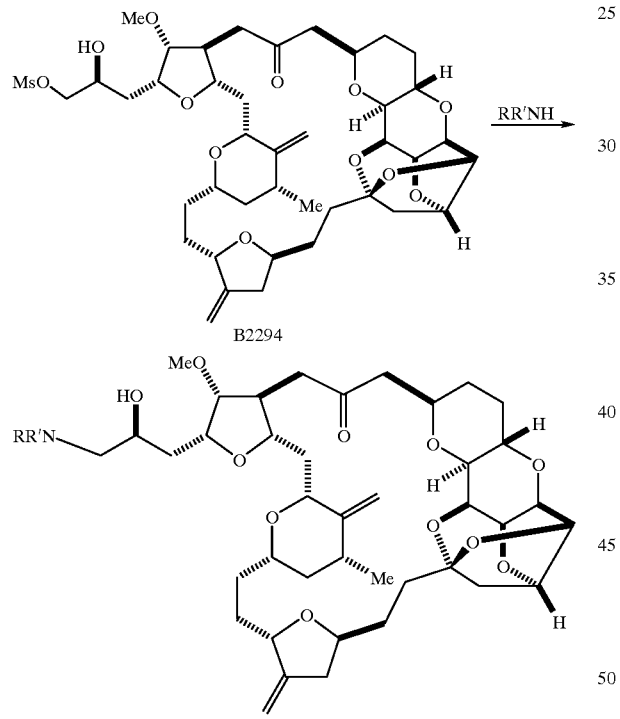

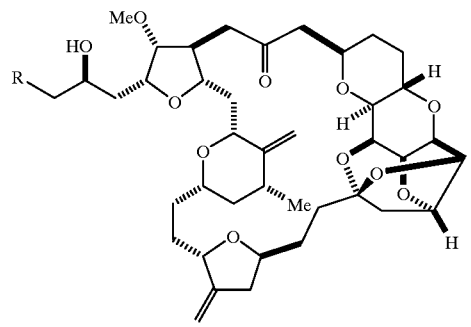

| | |
|---|---|
| B2320 | R = N,N-dimethylamino |
| B2330 | R = N-isopropylamino |
| B2336 | R = N-methylamino |
| B2339 | R = N-t-butylamino |
| B2417 | R = N-2-hydroxyethylamino |
| B2418 | R = N-piperazinyl |
| B2489 | R = N,N-bis-(2-hydroxyethyl)amino |
| B2490 | R = N-1,3-dihydroxy-2-propylamino |
| B2491 | R = N-benzylamino |
| ER803834 | R = N-piperidinyl |
| ER803835 | R = N-pyrrolidinyl |
| ER803836 | R = N-3-(R)-hydroxypyrrolidinyl |
| ER803843 | R = N-homopiperidinyl |
| ER803845 | R = N-para-methoxybenzylamino |
| ER803846 | R = N-phenethylamino |
| ER803851 | R = N-2-(S-hydroxymethyl)pyrrolidinyl |
| ER803852 | R = N-2-(R-hydroxymethyl)pyrrolidinyl |
| ER803868 | R = N-morpholinyl |
| ER803869 | R = N-ethylamino |
| ER803870 | R = N-imidazoyl |
| ER803883 | R = N,N-diethylamino |
| ER803884 | R = N-para-chlorobenzylamino |

These compounds are made by treating B2294 with an appropriate amine in a solvent such as methanol for a period of a few hours to several days. Progress of the reaction may be monitored by thin layer chromatography. A standard work-up procedure, well known to those of skill in the art, provides the desired compounds. The procedure below is to prepare ER803868; however this procedure is general and can be used to prepare any desired analog.

Synthesis of ER803868

To a solution of B2294, 1.2 mg, in methanol, 0.5 mL, was added morpholine, 0.012 mL. The mixture was stirred for 10 days with additional morpholine, 0.012 mL, being added on days 1,2,3, 4 and 8. The mixture was then chromatographed to give 1.4 mg of the desired compound.

D. Pharmacological Activity

Many of the individually disclosed drugs were tested for in vitro and in vivo activity (see Table 1, below). Screening methods included a standard in vitro cell growth inhibition assay using DLD-1 human colon cancer cells (ATCC accession number CCL 221) in a 96-well microtiter plate format (Finlay, G. J. et al Analytical Biochemistry 139:272–277, 1984), a U937 (ATCC accession number CRL 1593) mitotic block reversibility assay (described below), and in some cases, a LOX human melanoma tumor xenograft in vivo growth inhibition assay (see Table 1). Chemical stability to esterase degradation was also examined.

U937 Mitotic Block Reversibility Assay

U937 human histiocytic lymphoma cells were added to 75 cm² tissue culture flasks as $2.5 \times 10^6$ cells in 22.5 mL of RPMI Medium 1640 containing 10% Fetal Bovine Serum. Cells were allowed to adapt to the culture during 36 h of incubation at 37° C. in a humidified atmosphere containing 5% $CO_2$. Each test drug was then added to a flask as 2.5 mL of 10× final concentration. Final concentrations achieved were 0.1–1000 nM, in half log-increments, for a total of 10 concentration steps including a drug-free control flask which recieved 2.5 mL of media. Cells were incubated with drug for 12 h pretreatment period at 37° C. in a humidified atmosphere containing 5% $CO_2$.

The contents were removed from each flask and centrifuged at 300×g for 10 min at room temperature, after which drug-containing media was removed from cell pellet. Cells were resuspended in 25 mL of warm drug-free media and centrifuged at 300×g for 10 min at room temperature. After removing media from cell pellet, cells were resuspended in 35 mL of warm drug-free media, transferred to fresh flasks, and a 10 mL sample of cells immediately removed from each flask, immediately processed as described below and stored for later cell cycle analysis (0 hours of drug washout).

Incubation of the remaining 25 mL of cells continued in drug-free media for another 10 h. A 10 mL sample of cells was removed from each flask, immediately processed and stored for later cell cycle analysis (10 hours of drug washout) and 10 mL fresh replacement media was added to each incubation flask. Incubation of cells in drug-free media continued for 5 days. At day two, 20 mL of media and cells was removed from each flask and replaced with 20 mL fresh media. Viability of cells was quantified after 5 days by trypan blue exclusion techniques using hemacytometer counting.

Cells were processed for cell cycle analysis using modifications of the method published in Becton Dickinson Immunocytometry Systems source book section 1.11 (Preparation of Alcohol-Fixed Whole Cells From Suspensions For DNA Analysis). Briefly, each 10 mL sample of cells removed from the flasks at 0 and 10 hours of drug washout was separately centrifuged at 300×g for 10 min. After removing the media from the cell pellet, cells were resuspended in 3 mL cold saline. Seven milliliters cold 100% ethanol was slowly added with vigorous vortexing. Ethanol treated cell samples from 0 hour and 10 hour periods of compound washout were stored overnight at 4° C. Ethanol treated cells were centrifuged 300×g for 10 min, ethanol removed and cells then washed in 10 mL Phosphate Buffered Saline (PBS). Cells were resuspended in 0.5 mL of 0.2 mg/mL Ribonuclease A (Sigma No. R-5503) in PBS and incubated in 37° C. water bath for 30 min.

Cells were transferred to appropriate flow cytometry tubes and 0.5 mL of 10 mg/mL propidium iodide (PI) (Sigma No. P4170) in PBS was added to each tube. Cells were incubated with PI at room temperature in the dark for at least 15 min prior to analysis with a flow cytometer (Becton Dickinson FACScan flow cytometer or equivalent) Cells should be analyzed within an hour and kept in the dark at 4° C. until ready. Cell cycle analysis was performed on 0 hour and 10 hour cells using flow cytometric measurement of the intensity of cellular fluorescence. The intensity of propidium iodide fluorescence for each cell was measured on a linear amplification scale with doublet events ignored using doublet discrimination. The results obtained from analyzing 15,000 cells were presented as a histogram with increasing fluorescence intensity on the x-axis and the number of cells at a particular intensity level on the y-axis.

Figure 2:
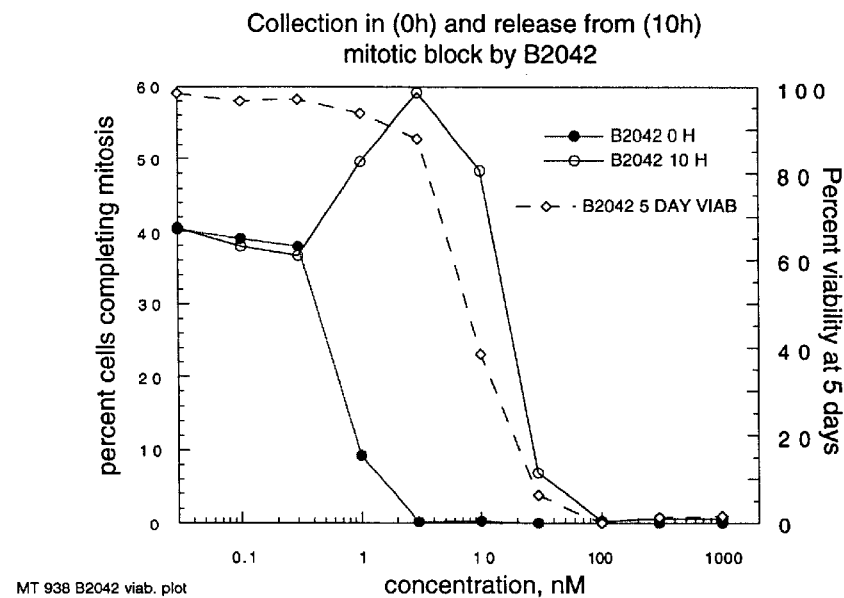
FIG. 2 is a graph showing the percentage of cells which have completed mitosis and returned to $G_1$ phase as a function of the concentration of compound B2042 in a mitotic block reversibility assay. The minimum concentration required for complete mitotic block at 0 hour is 3 nM. The minimum concentration required for complete mitotic block at 10 hour is 100 nM. The reversibility ratio for B2042 is thereof 33. Superimposed on this graph is a curve showing the percentage of viable cells at 5 days as a function of concentration of compound B2042.
Figure 3:
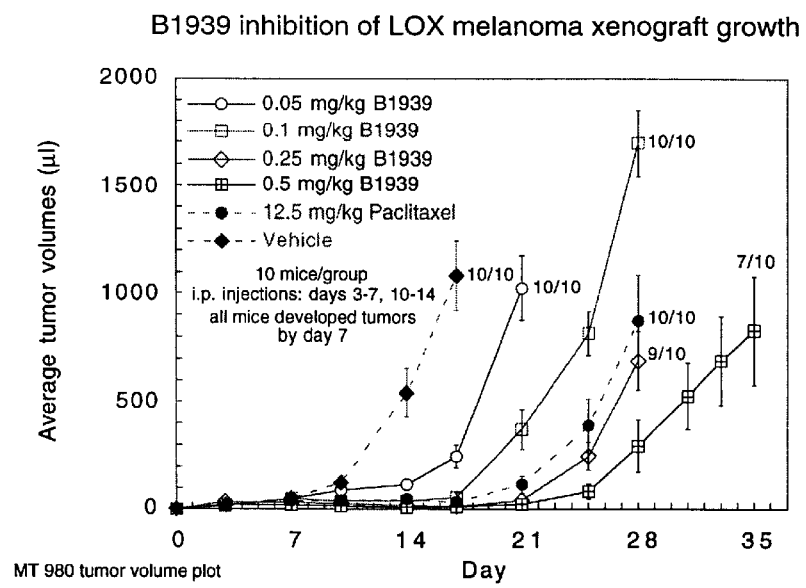
FIG. 3 is a graph showing the average tumor volume in microliters as a function of time (days) in a LOX melanoma xenograft growth inhibition assay. This illustrates the antitumor activity of a compound of formula (I), compound B1939. Paclitaxel and a vehicle control were used.
Figure 4:
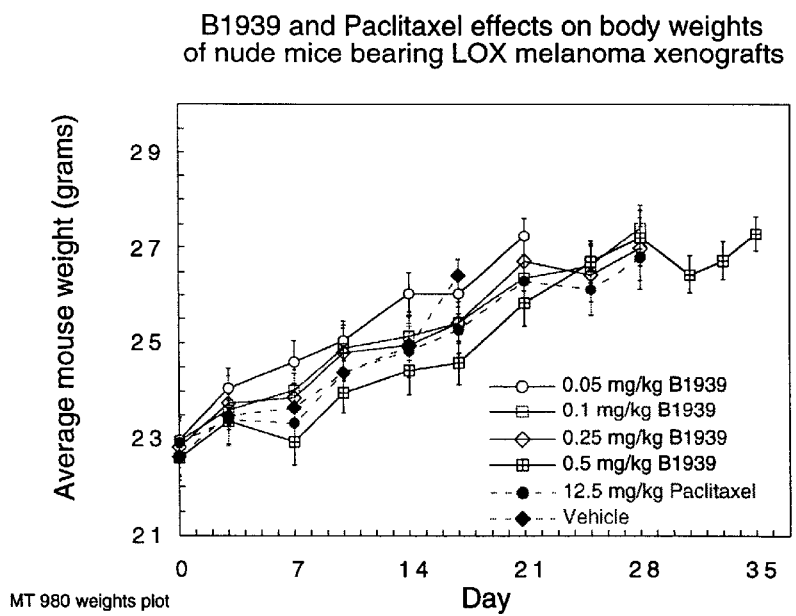
FIG. 4 is a graph showing the average body weight per mouse as a function of time (days) in the assay described in FIG. 3.

The intensity of PI staining is dependent on the amount of DNA in the cell so it is possible to identify cells in various phases of the cell cycle, such as cells that have not yet synthesized DNA since the last mitosis ($G_1$ phase), cells that are in intermediate stages of DNA synthesis (S phase), and cells that have doubled their complement of DNA and are ready to divide ($G_2$ phase). Cells that are blocked in the mitosis phase of the cell cycle also have double the amount of DNA compared to $G_1$ phase cells. If all cells are blocked in mitosis there are no $G_1$ phase cells, but if the block is removed when compound is removed, cells complete mitosis and reappear in the $G_1$ phase. The number of cells so reappearing in the $G_1$ or Sphase is thus a measure of the number of cells which have recently completed mitosis. For each sample at 0 and 10 hours after compound removal, the percentage of cells completing mitosis was quantified (as the number of cells reappearing in the $G_1$ phase) and plotted as a function of the initial concentration of compound used during the 12 hour pretreatment period. The percentage of cells still viable 5 days after drug washout was superimposed on the same graph, see, for example FIG. 1 and FIG. 2. A ratio can be determined between the compound concentration required to completely block all cells in mitosis at 0 hour and the concentration required to maintain the block 10 hours after compound removal. This was taken as a measure of a compound's reversibility, with ratios close to or equal to one indicating likely potent in vivo anti-tumor compounds (see Table 1, columns 4–6, and FIGS. 3 and 4).

TABLE 1

In Vitro Inhibition and Reversibility Data

| Compound | DLD-1* mean IC50, nm | SE | Complete Mitotic Block 0 hour, nM** | Complete Mitotic Block 10 hour, nM‡ | Reversibility Ratio |
|---|---|---|---|---|---|
| B1793 | 0.93 | 0.04 | 3 | 44 | 14.7 |
| B1794 | 12.20 | 0.72 | | | |
| B1918 | 1.27 | 0.12 | | | |
| B1920 | 2.00 | 0.15 | | | |
| B1921 | 24.00 | 1.15 | | | |
| B1922 | 0.53 | 0.01 | 3 | 30 | 10.0 |
| B1930 | 0.87 | 0.03 | | | |
| B1933 | 0.79 | 0.16 | | | |
| B1934 | 1.05 | 0.21 | 3 | 30 | 10.0 |
| B1939 | 19.34 | 2.36 | 12 | 12 | 1.0 |
| B1940 | 5.43 | 0.62 | | | |
| B1942 | 0.60 | 0.03 | 3 | 30 | 10.0 |
| B1963 | 0.56 | 0.04 | 3 | 20 | 6.7 |
| B1973 | 1.15 | 0.24 | | | |
| B1984 | 1.01 | 0.15 | | | |
| B1987 | 1.82 | 0.21 | | | |
| B1988 | 2.67 | 1.02 | | | |
| B1990 | 1.30 | 0.06 | | | |
| B1991 | 0.69 | 0.03 | | | |
| B1992 | 0.86 | 0.07 | | | |
| B1998 | 1.23 | 0.13 | | | |
| B2003 | 1.21 | 0.12 | | | |
| B2004 | 0.63 | 0.04 | | | |
| B2008 | 2.63 | 0.63 | | | |
| B2010 | 0.71 | 0.12 | | | |
| B2011 | 1.81 | 0.52 | | | |
| B2013 | 0.49 | 0.07 | 2 | 30 | 15.0 |
| B2014 | 0.87 | 0.09 | | | |
| B2015 | 2.78 | 0.23 | | | |
| B2016 | 0.66 | 0.06 | | | |
| B2019 | 0.82 | 0.07 | | | |
| B2034 | 0.74 | 0.03 | | | |
| B2035 | 0.76 | 0.09 | | | |
| B2037 | 0.66 | 0.11 | | | |
| B2039 | 0.91 | 0.08 | | | |
| B2042 | 1.93 | 0.11 | 3 | 100 | 33.3 |
| B2043 | 1.70 | 0.06 | | | |

TABLE 1-continued

In Vitro Inhibition and Reversibility Data

| Com-pound | DLD-1* mean IC50, nm | SE | Complete Mitotic Block | | Reversi-bility Ratio |
|---|---|---|---|---|---|
| | | | 0 hour, nM** | 10 hour, nM† | |
| B2070 | 0.64 | 0.09 | 3 | 30 | 10.0 |
| B2073 | 0.89 | 0.15 | | | |
| B2086 | 11.17 | 1.96 | | | |
| B2088 | 1.23 | 0.12 | | | |
| B2090 | 0.52 | 0.04 | 2 | 10 | 5.0 |
| B2091 | 1.36 | 0.07 | 3 | 30 | 10.0 |
| B2102 | 3.47 | 0.22 | | | |
| B2136 | 5.23 | 1.04 | 3 | 3 | 1.0 |
| B2294 | 0.80 | 0.01 | | | |
| B2320 | 1.20 | 0.17 | 1 | 10 | 10.0 |
| B2330 | 4.40 | 0.42 | 7 | 7 | 1.0 |
| B2336 | 3.33 | 0.09 | 10 | 10 | 1.0 |
| B2339 | 4.30 | 0.21 | 3 | 3 | 1.0 |
| B2417 | 12.67 | 0.33 | 10 | 10 | 1.0 |
| B2418 | 3.63 | 0.17 | 10 | 10 | 1.0 |
| B2489 | 14.67 | 2.03 | 10 | 10 | 1.0 |
| B2490 | 35.67 | 3.33 | 100 | 100 | 1.0 |
| B2491 | 0.92 | 0.14 | 2 | 10 | 6.7 |
| ER803834 | 0.47 | 0.08 | 1 | 10 | 10.0 |
| ER803835 | 15.33 | 0.33 | 10 | 10 | 1.0 |
| ER803836 | 1.97 | 0.12 | 3 | 10 | 3.3 |
| ER803843 | 0.49 | 0.05 | 1 | 10 | 10.0 |
| ER803845 | 1.50 | 0.20 | 3 | 10 | 3.3 |
| ER803846 | 1.16 | 0.10 | 1 | 10 | 10.0 |
| ER803851 | 3.33 | 0.26 | 3 | 3 | 1.0 |
| ER803852 | 3.03 | 0.50 | 3 | 10 | 3.3 |
| ER803868 | 0.43 | 0.03 | 3 | 10 | 3.3 |
| ER803869 | 4.13 | 0.64 | 3 | 3 | 1.0 |
| ER803870 | 1.27 | 0.12 | 3 | 30 | 10.0 |
| ER803883 | 1.02 | 0.04 | 1 | 10 | 10.0 |
| ER803884 | 0.59 | 0.03 | 1 | 10 | 10.0 |

*= in vitro cell growth inhibition
**= before washout
†= after washout

The invention also features a method for identifying an agent that induces a sustained mitotic block in a cell after transient exposure of the cell to the agent. The invention features determining the relative reversibility of the test compound by relating the measurement of step (d) and the measurement of step (f), as described below. This determination may be a ratio, or an arithmetic difference, for example. In one aspect, the method includes:

(a) incubating a first cell sample with a predetermined concentration of a test compound for a time interval between that sufficient to empty the $G_1$ population and that equivalent to one cell cycle (e.g., typically, 8–16 hours, or about 12 hours);

(b) substantially separating the test compound from said first cell sample (e.g. by washing or changing media);

(c) incubating said first sample in media free of the test compound for a time interval sufficient to allow at least 80% (e.g., 85%, 90%, and preferably 95%, 98%, or 99%) of the cells released from the mitotic block induced by a highly reversible mitotic inhibitor to complete mitosis and return to the $G_1$ phase (e.g., typically 6–14 hours, or about 10 hours after separation step (b)); and (d) measuring the percentage of transiently-exposed cells from step (c) that have completed mitosis and returned to the $G_1$ phase (e.g., measuring a cell cycle marker, such as DNA-dependent PI fluorescence).

One aspect of this screening method include the further steps of:

(e) incubating a second sample of cells with a concentration of the test compound less than or equal to that used in step (a) for a time interval between that sufficient to empty the $G_1$ population and that equivalent to one cell cycle;

(f) measuring the percentage of cells from step (e) that have completed mitosis and have returned to the $G_1$ phase; and (g) determining a reversibility ratio of the test compound.

In one embodiment of the method, the first and second cell samples are suspension culture cells selected from, for example, human leukemia, human lymphoma, murine leukemia, and murine lymphoma cells. The first and second cell samples may be incubated simultaneously (steps (a) and (e)) or in separate portions. Other embodiments further include before step (a), the step (i) of estimating a desirable time interval for incubating said first cell sample with a reversible mititotic blocking agent (or, alternatively, said test compound) to provide a satisfactory majority of cells collected at mitotic block; and wherein the incubation of step (a) is for the time interval estimated in step (i). Another embodiment of the method further includes before step (c), the step (ii) of estimating a desirable time interval for the test compound-free incubation of step (c), said step (ii) comprising determining the time interval after which at least 80% of the cells pretreated with a highly reversible antimititotic agent complete mitosis and reenter $G_1$ phase; and wherein the incubation of step (c) is for the time interval determined in step (ii). Another embodiment of the method utilizes non-suspension culture cells from, for example, adherent human or murine cancer cells, harvested by any suitable means for detaching them from tissue culture flasks.

One aspect of the method further includes repeating steps (a)–(f) using a range of relative concentrations of test compound to determine what two substantially minimum concentrations of the test compound provide substantially complete mitotic block in step (d) and in step (f), respectively. The ratio of these minimum sufficient concentrations is an index of reversibility (see detailed U937 protocol for preparation of exemplary dose-response curves). These concentrations may be determined by extrapolating curves of the percentage of cells (from steps (d) and (f)) as a function of concentration (e.g., by testing only a few concentrations, such as 3 or fewer), or by empirically testing a full range of concentrations.

The above methods are useful for identifying an agent (test compound) that inhibits mitosis, for identifying a mitotic blocking agent which substantially retained its mitosis blocking effectiveness after its removal, and for predicting, for example, the $IC_{50}$ or the $IC_{95}$ of a mitotic blocking agent. When compared with relatively reversible antimitotic agents, substantially irreversible antimitotic agents, in other words, agents which continue to block mitosis in a cell which has been only transiently exposed to the agent, are likely to be more effective in vivo where natural processes, including multi-drug resistance (MDR) pumps and metabolic or other degradative pathways, prevent prolonged exposure. The effectiveness of relatively reversible antimitotic agents may depend upon a period of sustained exposure.

In view of the cost of developing pharmaceuticals, the economic advantages of determining reversibility ratios, as described above, are considerable. The above methods can be used, for example, to predict whether a test compound with good in vitro activity will be effective in vivo, such as in a clinical trial. Relatively reversible agents would not be expected to perform as well as irreversible agents. This is shown, for example, by contrasting the data for two known compounds, the relatively irreversible antimitotic agent vincristine and the highly reversible antimitotic agent vinblastine.

TABLE 2

Reversibility Characteristics of Vinblastine and Vincristine

| Compound | Drug concentration required for complete mitotic block, nM | | Reversibility ratio | Interpretation |
| --- | --- | --- | --- | --- |
| | 0 hour (before washout) | 10 hour (after washout) | | |
| Vinblastine | 10 | 600 | 60 | Highly Reversible |
| Vincristine | 10 | 10 | 1 | Irreversible |

Analyses of the antimitotic drugs vinblastine and vincristine in the U937 Mitotic Block Reversibility Assay indicate that despite identical potencies to induce initial mitotic blocks (0 hour values), the abilities of the two drugs to induce mitotic blocks which are sustained 10 hour after drug washout (10 hour values) are very different: vincristine induces irreversible mitotic blocks, while those induced by vinblastine are highly reversible.

Figure 5:
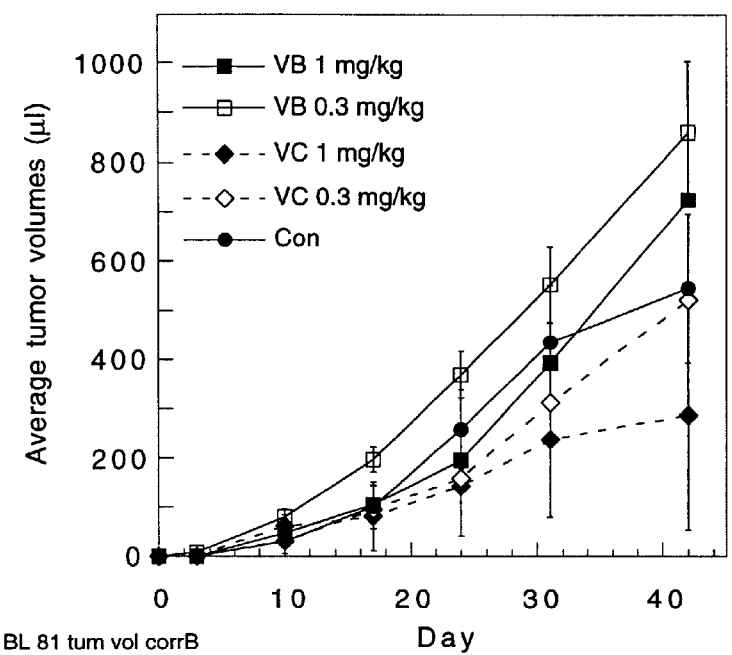
FIG. 5 is a graph showing the average tumor volume in microliters as a function of time (days) in a COLO 205 human colon cancer xenograft growth inhibition assay, showing the antitumor activities of vinblastine and vincristine.

Analyses of in vivo anticancer activities of the antimitotic drugs vinblastine and vincristine against COLO 205 human colon cancer xenografts grown sub-cutaneously in immunocompromised (nude) mice indicate that at equivalent doses of 1 mg/kg, vincristine shows substantial cancer growth inhibitory activity while vinblastine is inactive (FIG. 5). At the lower dose of 0.3 mg/kg, vincristine still produces moderate growth inhibition, while vinblastine is again inactive. The greater in vivo activity of vincristine correlates with its irreversibility relative to vinblastine's high reversibility.

E. Use

The disclosed compounds have pharmacological activity, including anti-tumor and anti-mitotic activity as demonstrated in section D above. Examples of tumors include melanoma, fibrosarcoma, monocytic leukemia, colon carcinoma, ovarian carcinoma, breast carcinoma, osteosarcoma, prostate carcinoma, lung carcinoma and ras-transformed fibroblasts.

The invention features pharmaceutical compositions which include a compound of formula (I) and a pharmaceutically-acceptable carrier. Compositions can also include a combination of disclosed compounds, or a combination of one or more disclosed compounds and other pharmaceutically-active agents, such as an anti-tumor agent, an immune-stimulating agent, an interferon, a cytokine, an anti-MDR agent or an anti-angiogenesis agent. Compositions can be formulated for oral, topical, parenteral, intravenous, or intramuscular administration, or administration by injection or inhalation. Formulations can also be prepared for controlled-release, including transdermal patches.

A method for inhibiting tumor growth in a patient includes the step of administering to the patient an effective, anti-tumor amount of a disclosed compound or composition. The invention also contemplates combination therapies, including methods of co-administering a compound of formula (I) before, during, or after administering another pharmaceutically active agent. The methods of administration may be the same or different. Inhibition of tumor growth includes a growth of the cell or tissue exposed to the test compound that is at least 20% less, and preferably 30%, 50%, or 75% less than the growth of the control (absence of known inhibitor or test compound).

Other Embodiments

The essential features of the invention can be easily discerned from the above description and the claims below. Based on the entire disclosure, variations of the disclosed compounds and methods of the invention described can be designed and adapted without departing from the spirit and scope of the claims and the disclosure. References and publications described herein are hereby incorporated in their entirety.

What is claimed is:

1. A compound having the formula:

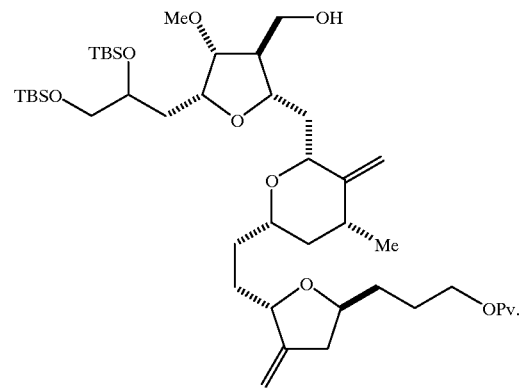

2. A compound having the formula:

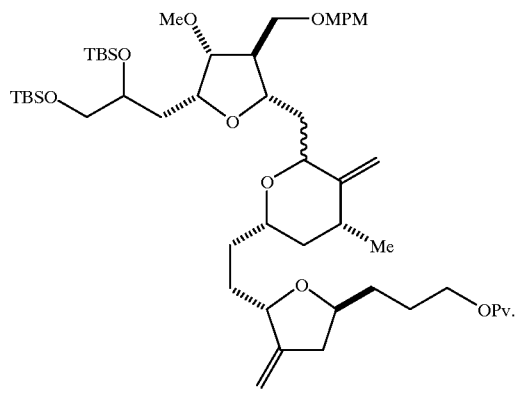

3. A compound having the formula:
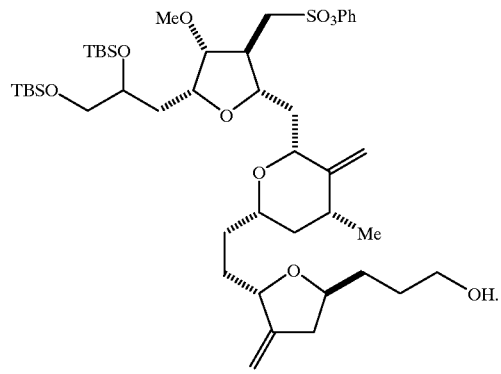
4. A compound having the formula:
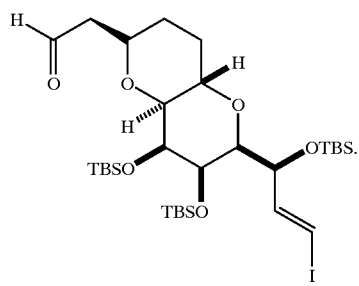
* * * * *